US007998486B2

(12) United States Patent
Mautino et al.

(10) Patent No.: US 7,998,486 B2
(45) Date of Patent: Aug. 16, 2011

(54) ENHANCED IMMUNOGENICITY OF TUMOR ASSOCIATED ANTIGENS BY ADDITION OF ALPHAGAL EPITOPES

(75) Inventors: Mario R. Mautino, Ankeny, IA (US); Nicholas N. Vahanian, Polk City, IA (US); Won-Bin Young, Pittsburgh, PA (US); Gabriela Rossi, Ankeny, IA (US); Charles J. Link, Clive, IA (US); Firoz Jaipuri, Ames, IA (US)

(73) Assignee: NewLink Genetics Corporation, Ames, IA (US)

( * ) Notice: Subject to any disclaimer, the term of this patent is extended or adjusted under 35 U.S.C. 154(b) by 557 days.

(21) Appl. No.: 11/977,203

(22) Filed: Oct. 24, 2007

(65) Prior Publication Data
US 2009/0060930 A1 Mar. 5, 2009

Related U.S. Application Data

(60) Provisional application No. 60/862,840, filed on Oct. 25, 2006.

(51) Int. Cl.
*A61K 38/00* (2006.01)
(52) U.S. Cl. ............. 424/193.1; 514/2; 514/8; 530/300; 530/350; 530/345; 424/278.1; 424/280.1; 424/277.1
(58) Field of Classification Search .................. 530/300, 530/350, 345; 424/184.1, 193.1, 277.1, 278.1, 424/280.1; 514/2, 8
See application file for complete search history.

(56) References Cited

U.S. PATENT DOCUMENTS

| | | | |
|---|---|---|---|
| 5,869,035 | A | 2/1999 | Link et al. |
| 5,879,675 | A | 3/1999 | Galili |
| 6,187,306 | B1 | 2/2001 | Pardoll et al. |
| 6,218,166 | B1 | 4/2001 | Ravindranath et al. |
| 6,333,028 | B1 | 12/2001 | Berd |
| 6,361,775 | B1 | 3/2002 | Galili |
| 6,713,055 | B2 | 3/2004 | Schiff |
| 6,943,239 | B2 * | 9/2005 | Holgersson et al. .......... 530/402 |
| 7,005,126 | B1 | 2/2006 | Link et al. |
| 2004/0191229 | A1 | 9/2004 | Link et al. |
| 2005/0201993 | A1 | 9/2005 | Link et al. |
| 2007/0014774 | A1 | 1/2007 | Link et al. |
| 2007/0014775 | A1 | 1/2007 | Link et al. |

OTHER PUBLICATIONS

Abdel-Motal et al. (J. Virol. Jul. 2006; 80 (14): 6943-6951).*
Naicker et al. (Org. Biomol. Chem. Mar. 7, 2004; 2 (5): 660-664).*
Galili et al. (Cancer Immunol. Immunother. 2004; 53: 935-945).*
Meldal et al. (Current Op. Chem. Biol. 1997; 552-563).*
Brocke et al. (Biorg. Med. Chem. 2002; 10: 3085-3112).*
LaTemple et al. (Cancer Res. 1999; 59: 3417-3423).*
Manches et al. (Haematologica. May 2005; 90 (5): 625-634).*
Macher et al. (Biochim. Biophys. Acta. 2008; 1780 (2): 75-88).*
ATCC Cell Lines and Hybridomas, Eighth Edition, 1994, edited by Robert Hey, PhD, et al., published by American Type Culture Collection, Rockville, Maryland USA (1994), 4 pages.
Chamberlain, et al. (2000) Expert Opinion on Pharmacology, 1(4):603-614.
Galili et al. (2001) "Preparation of Autlogous Leukemia and Lymphoma Vaccines Expressing Alpha-Gal Epitopes," J. Hematotherpay and Stem Cell Research, 10(4):501-511.
LaTemple, et al. (1996) "Synthesis of alpha-Galactosyl Epitopes by Recombinant α1,3Galactosyltransferase for Opinization of Human Tumor Cell Vaccines by Anti-Galactose," Cancer Research, 56:3069-3074.
LaTemple et al. (1999) "Increased Immunogenicity of tumor vaccines complexed with anti-gal: studies in knockout mice for α1, 3galactosyltransferase," Cancer Research, 59(4):3417-3423.
Gorelik, et al. (1995) "Alterations of cell surface carbohydrates and inhibition of metastatic property of murine melanomas by α1,3Galactosyltransferase gene transfection," Cancer Research, 55(18):4166-4173.
Galili et al. (2003) "Expression of α-gal epitopes on ovarian carcinoma membranes to be used as novel autologous tumor vaccine," Gynecologic Oncology, 90(1):100-108.
Yoshimura, et al. (2001) "Expression of xenoantigen transformed human cancer cells to be susceptible to antibiody-mediated cell killing," Cancer Letters, 164(2):155-160.
Larson, et al. (1989) "Isolation of cDNA encoding a murine UDPgalactose:β-D-galactosyl-1,4-N-acetyl-D-glucosaminide α-1,3-galactosyltransferase: Expression cloning by gene transfer," Proc. Natl. Acad. Sci. USA, 86:8227-8231.
Tratschin, et al. (1985) "Adeno-Associated Virus Vector for High-Frequency Integration, Expression, and Rescue Genes in Mammalian Cells," Molecular and Cellular Biology 5(11):3251-3260.
Chapter 4. Reverse Transcriptase and the Generation of Retroviral DNA. Retroviruses, Edited by John M. Coffin, Seteph H. Hughes and Harold E. Varmus, 1997, Cold Spring Harbor Laboratory Press, pp. 121-125.
Miller and Rosman (19989) "Improved retroviral vectors for gene transfer and expression," Biotechniques 7(9):984-6.
Genbank Entry for M28247.1 at the National Center for Biotechnology Information, Submitted Sep. 22, 1989.
Genbank Entru for X05157.1 at the National Center for Biotechnology Information, J. Gen Virol. 68 (PT 3), 683-693, (1987).

(Continued)

*Primary Examiner* — Stephen Rawlings
(74) *Attorney, Agent, or Firm* — Cooley LLP

(57) ABSTRACT

The invention relates to methods and compositions for causing the selective targeting and killing of tumor cells. The present invention describes prophylactic or therapeutic cancer vaccines based on purified TAA proteins or TAA-derived synthetic peptides altered by chemical, enzymatic or chemo-enzymatic methods to introduce αGal epitopes or αGal glycomimetic epitopes, in order to allow for enhanced opsonization of the antigen by natural anti-αGal antibodies to stimulate TAA capture and presentation, thereby inducing a humoral and cellular immune response to the TAA expressed by a tumor. The animal's immune system thus is stimulated to produce tumor specific cytotoxic cells and antibodies which will attack and kill tumor cells present in the animal.

9 Claims, 11 Drawing Sheets

OTHER PUBLICATIONS van Elsas et al. (2001) "Elucidating the Autoimmune and Antitumor Effector Mechanism of a Treatment Based on Cytotoxic T Lymphocyte Antigen-4 Blockade in Combination with B16 Melanoma Vaccine: Comparison of Prophylaxis and Therapy," J. Exp. Med. 194(4):481-489.

Galili, U., et al., Intratumoral Injection of a-gal Glycolipids Induces Xenograft-Like Destruction and Conversion of Lesions into Endogenous Vaccines, J. Immunol., 178(7):4676-4687 (Apr. 2007).

Galili, U., The a-gal epitope and the anti-Gal antibody in xenotransplantation and in cancer immunotherapy, Immunology and Cell Biology, 83:674-686 (2005).

Rossi, et al., Effective treatment of preexisting melanoma with whole cell vaccines expressing alpha(1,3)-galactosyl epitopes, Cancer Res., 65(22):10555-10561 (Nov. 2005).

* cited by examiner

ENHANCED IMMUNOGENICITY OF TUMOR ASSOCIATED ANTIGENS BY ADDITION OF ALPHAGAL EPITOPES

CROSS-REFERENCE TO RELATED APPLICATIONS

This application claims priority under 35 U.S.C. §120 to provisional application Ser. No. 60/862,840 filed Oct. 25, 2006, herein incorporated by reference in its entirety.

FIELD OF THE INVENTION

The present invention relates to methods and compositions for treating cancer by stimulating humoral and cellular immune responses against tumor cells. In particular, this invention is directed to methods and compositions to enhance the humoral and cellular immunogenicity of purified tumor specific antigens.

BACKGROUND OF THE INVENTION

Despite multiple preventive and therapeutic approaches, cancer is one of the major causes of death worldwide. In addition to chemotherapy and radiotherapy, manipulation of the immune system in different types of immunotherapies has shown encouraging results in human clinical trials (Berzofsky et al. 2004; Gattinoni et al. 2006). However, new immunotherapies are greatly needed because currently available treatments are still partially effective in cancer eradication (Rosenberg et al. 2004).

Different modalities of cancer vaccines have shown some degree of clinical efficacy. Whole tumor cell vaccines, administered in presence of adjuvant and genetically engineered tumor cells that express cytokines (i.e., granulocyte macrophage colony-stimulating factor and interleukin 2), are being studied extensively (Dranoff 2002; Rossi et al. 2005a). These vaccines have the advantage of expressing relevant tumor-associated antigens shared by the patient's cancer cells. However, one of the disadvantages of these vaccines is the weak antigen presentation, poor ability to stimulate a potent immune response and the potential to cause autoimmune reaction due to non-tumor specific stimulation of immunity against self antigens co-expressed by normal cells (Chianese-Bullock et al. 2005).

The use of complex mixtures of whole tumor cells or tumor-derived material does not take advantage of the specificity of treatment that immunotherapy can provide over other forms of therapy. Theoretically, an antibody or T-cell mediated immune response can recognize unique epitopes that are differentially expressed by tumor cells and destroy those cells that express that antigen without affecting normal cells and without the risk of triggering an autoimmune response. To take advantage of specificity, large efforts have been invested in the discovery of tumor associated antigens (TAA). Antigen-specific immunotherapy represents an attractive approach for cancer treatment because of the capacity to eradicate systemic tumors at multiple sites in the body while retaining the exquisite specificity to discriminate between neoplastic and non-neoplastic cells.

An extensive list of TAAs is available (Novellino et al. 2005; Renkvist et al. 2001). Depending on the specificity of tissue expression and ubiquitousness, tumor antigens can be classified in several categories: 1) antigens that are expressed only in an individual patient's tumor; 2) antigens that are commonly expressed in a group of tumors of similar histology; 3) tissue-differentiation antigens; and 4) antigens that are ubiquitously expressed by normal and malignant cells but that mutate in tumor cells. Depending on the group of TAA being targeted by immunotherapy, the patient treatment will be individualized (group 1) or generic for different patients.

Discovery of such TAAs has prompted many immunotherapy and vaccination studies in animals and clinical trials (Antonia et al. 2004; Phan et al. 2003; Rosenberg et al. 1998a; Rosenberg et al. 1998b). The first attempts of immunotherapy using purified TAA proteins with or without adjuvant produced disappointing results. For example, immunization of mice with purified protein of a TAA from syngeneic origin (mouse Tyrosinase gp75) does not result in any detectable antibody or T cell response to the TAA, due to a pre-established immune tolerance to the unaltered tumor antigen which is also expressed by normal cells (Naftzger et al. 1996). However, immunization of mice with an altered form of the protein, either by a xenogeneic human gp75 protein or a glycosylated variant of gp75 purified from insect cells was able to break the tolerance and induce an antibody response against gp75, that was correlated with protection against tumors expressing gp75, and also induction of autoimmunity against normal melanocytes that also express gp75 (Naftzger et al. 1996). A wide body of evidence supports the notion that a pre-existing state of tolerance against a self-antigen present in tumor cells can be broken by presentation of mutated antigens, antigens in different conformations or with different post-translational modifications.

Peptide vaccines composed of short peptides are easier to manufacture in large scale than purified protein subunits. Peptide vaccines have been developed by mapping the epitopes from a TAA that bind to the MHC molecule and that are recognized by the T cell receptor complex. These epitopes are 7-13 amino acid sequences derived from the TAA by proteolytic degradation of the TAA in the 26S proteasome. Different antigenic peptides derived from the same TAA can bind to different haplotypes and classes of MHC molecules with different affinities, thereby providing an additional level in the control of specificity of the immune response. This means that individual 7-13 amino acid peptides might be useful only in patients with appropriate HLA molecules capable of presenting that peptide. Several strategies have been developed to improve immunogenicity of peptides. Modification of the amino acid sequence of epitopes can improve the efficacy of vaccines by: 1) increasing affinity of peptide for MHC molecules (Berzofsky 1993; Berzofsky et al. 2001; Rosenberg et al. 1998a); 2) increasing binding to the TCR (Fong et al. 2001; Rivoltini et al. 1999; Zaremba et al. 1997); or 3) inhibiting proteolysis of the peptide by serum peptidases (Berzofsky et al. 2001; Parmiani et al. 2002). Epitope enhancement has shown greater efficacy in clinical trials (Rosenberg et al. 1998a). However, epitope enhancement is a laborious process that is specific for each epitope/MHC pair that is being evaluated. Results indicate that vaccination with TAA-derived peptides can elicit tumor-specific immunity and establish long-term memory without autoimmunity (Scanlan et al. 2002; Soares et al. 2001). For example, for breast cancer, vaccines composed of epitopes that are derived from melanoma-associated antigen 3 (MAGE3) or other members of the MAGE gene family, HER2/NEU (Disis et al. 2002), carcinoembryonic antigen (CEA) (Cole et al. 1996; Schlom et al. 1996) or mucin 1 have been extensively studied and shown to be immunogenic without causing autoimmunity. Similarly, for melanoma, many studies have been undertaken in animal models and in clinical trials (Phan et al. 2003). As these antigens are commonly expressed by tumors in different patients, large scale production of vaccines can be developed for use in a large number of patients.

Despite the advantages of peptide vaccines and some encouraging preliminary data in animal models and clinical trials, tumor vaccines based on individual peptides derived from TAAs have not produced the results that were initially hoped, and often require combinations with potent adjuvants and stimulating cytokines. One of the possible causes of the poor immunogenic effect of isolated peptides are poor uptake by APCs, poor activation of APCs by the vaccinating peptides, poor loading into the MHC-I and/or MHC-II molecules, poor affinity for certain combinations of peptide/MHC-specific alleles, pre-existing immune tolerance to self-antigens or a combination thereof.

An alternative way to enhance presentation of antigenic epitopes is by use of in vitro loaded dendritic cells. Mature dendritic cells are the most efficient antigen presenting cells and are the preferred cellular target to mediate the elicitation of a potent immune response. For that reason they have been tested in clinical settings as vaccination vectors (Morisaki et al. 2003). Dendritic cell vaccines are obtained by in vitro differentiation of autologous patient-derived CD34+ bone marrow cells with IL-3, IL-6, SCF, GM-CSF, IL-4 or from circulating monocytes by incubation with GM-CSF, IL-4. Immature DCs can be matured in vitro with CD40L, TNFα or LPS. In vitro differentiated DCs are pulsed with tumor antigen peptides, proteins or tumor cell lysates. Some immunological and clinical responses have been reported for melanoma, follicular B cell lymphoma, multiple myeloma and pancreatic cancer, but results have not been completely satisfactory, possibly due to inconsistencies in DCs preparation and pulsing (Berzofsky et al. 2004). Therefore, there is still much room for improvement. The main disadvantage of this approach is that it constitutes a personalized therapy specific for each patient, which limits the scalability of the procedure. DCs need to be collected from each patient, cultured and differentiated in vitro, which is a costly and labor intensive procedure. The inconsistencies in the DCs methods of collection, differentiation, maturation and pulsing can be potentially overcome by vaccination methods that induce migration and maturation of immature DCs in vivo. Vaccination with purified antigens in the form of soluble peptides or proteins results in uptake of these antigens by pinocytosis, endocytocis or phagocytosis through the endosomal-lysosomal pathway, which ultimately delivers peptide onto surface MHC class II but not to MHC class I complexes. Thereby, vaccination with soluble proteins or peptides in their native form does result mainly in a CD4+ mediated immune response but not in a potent stimulation of CD8+ T cells, which is believed to be the main T cell type needed for an efficient immune response against tumors. It has been demonstrated that uptake of antigen-antibody immunocomplexes by the FcγRI and FcγRIII receptors in DCs mediates activation and maturation of DCs and promotes cross-presentation of antigen in the context of both MHC class I and class II complexes, thereby stimulating both CD4+ and CD8+ cells (Ackerman et al. 2005; Heath et al. 2004; Heath and Carbone 2001; Palliser et al. 2005; Rafiq et al. 2002; Schnurr et al. 2005). Consistently with this, vaccination of mice with DCs loaded with immunocomplexes elicits a protective antitumor response against tumors bearing the antigen present in the immunocomplex (Rafiq et al. 2002). It is important to highlight, however, that in this study the animals did not have a pre-existing state of immunotolerance against the vaccinating antigen.

An efficient way to promote the formation of immunocomplexes in vivo is by modifying the antigen to contain epitopes or mimotopes against which the recipient host has naturally occurring pre-existing antibodies. This can be accomplished by several means such as by introducing A or B blood antigen groups and administering the modified antigen to an O-type blood recipient. Alternatively, a preferred method is to modify the antigen to contain αGal epitopes (Galα1-3)Galβ (1,4)GlcNAc-R) that would be recognized by natural anti-αGal antibodies existing in humans. The formation of immunocomplexes by anti-αGal antibodies and αGal epitopes was first observed during organ xenotransplantation. When transplanting an organ from a non-primate mammal into an Old World primate, the organ is destroyed by a hyperacute reaction within minutes of transplantation (Joziasse and Oriol 1999; Maruyama et al. 1999). The hyperacute rejection of xenotransplants to higher primates is mediated by the binding of anti-αGal antibodies from the recipient to αGal epitopes expressed on the xenograft and complement activation through the classic pathway (Joziasse and Oriol 1999). In addition, noncomplement fixing natural anti-αGal antibody induces antibody dependent cell-mediated cytotoxicity (ADCC) that initiates tissue damage in xenotransplants mediated by natural killer cells (Baumann et al. 2004; Schaapherder et al. 1994; Watier et al. 1996a; Watier et al. 1996b). The gene encoding for α(1,3)-galactosyltransferase (αGT), which catalyzes the synthesis of αGal epitopes on glycoproteins and glycolipids, is inactive in humans and Old World primates but is functional in other mammals (Larsen et al. 1990). The human immune system is continuously stimulated by intestinal and pulmonary bacterial flora to produce natural antibodies that recognize αGal epitopes. Anti-αGal constitutes approximately 1% of circulating IgG (Galili et al. 1984; Galili et al. 1988) and is also found in the form of IgA and IgM (Davin et al. 1987; Sandrin et al. 1993). It is produced by 1% of circulating B lymphocytes (Galili et al. 1993).

It has been demonstrated that immunogenicity of viral or xenogeneic proteins, against which there is no pre-established tolerance, is enhanced by introduction of αGal epitopes. For example, immunization of αGT knockout mice with BSA conjugated with αGal led to significant production of anti-BSA IgG antibodies without the need for adjuvant. The presence of αGal also led to an increase in the T cell response to BSA (Benatuil et al. 2005). Additionally, it has been shown that the presence of anti-αGal antibodies enhanced the cytotoxic T cell response against a viral antigen following vaccination with MoMLV transformed cell lines that express αGal on their surface (Benatuil et al. 2005). Similarly, enzymatic modification of influenza hemagglutinin with recombinant αGT results in addition of αGT epitopes to HA. It has been shown that αGal$^{(+)}$ HA present in whole virions increases the uptake and T cell stimulating capacity of antigen presenting cells, which is reflected by increased proliferation of a HA-specific T cell clone (Galili et al. 1996). Finally, it was recently shown that αGT KO mice (that were pre-induced to have anti-αGal antibodies) vaccinated with enzymatically modified $\alpha Gal^{(+)}$ HIV-1 gp120 envelope protein induces at least 100-fold higher titer of anti-gp120 antibodies than mice vaccinated with the same dose of an unmodified $\alpha Gal^{(-)}$ gp120 (Abdel-Motal et al. 2006). In addition, mice vaccinated with $\alpha Gal^{(+)}$ gp120 had higher titer of HIV-1 neutralizing antibodies and larger number (~10-fold) of T cells reactive to $\alpha Gal^{(-)}$ gp120. This indicates that the presence of αGal epitopes in conjunction with anti-αGal antibodies can provide an adjuvant effect that allows for efficient T cell and B cell priming to native protein antigens that do not bear αGal epitopes. In these previous experiments, the αGT KO hosts did not have a pre-existing state of immune tolerance against the $\alpha Gal^{(+)}$ antigens. It is not known whether a pre-existing state of tolerance to self antigens or TAA can be broken by vaccination with immunocomplexes composed of αGal$^{(+)}$ TAA protein or peptides.

We and others have suggested that the hyperacute rejection of whole cell cancer vaccines expressing αGal epitopes could be exploited as new therapeutic approach to treat human malignancies (Galili 2004; Galili and LaTemple 1997; LaTemple and Galili 1999; Link et al. 1998). The hypothesis that humoral immunity to αGal epitopes may induce anticancer immunity and bypass or break a pre-existing state of tolerance towards self-antigens shared by normal and tumor cells was tested using the α(1,3)-galactosyltranferase knockout (aGT KO) mouse model (Thall et al. 1995). We and others have shown that mice with anti-αGal antibodies are protected when challenged with αGal-expressing cancer cells, whereas no protection was observed in mice without anti-αGal antibodies (Posekany et al. 2004; Unfer et al. 2003). Moreover, the rejection of melanoma cells expressing αGal epitopes conferred protection against melanoma cells lacking the expression of αGal epitopes. Mice that rejected the first challenge with live αGal$^{(+)}$ B16 cells were protected from a second rechallenge with αGal$^{(-)}$ B16 (Rossi et al. 2005a; Rossi et al. 2005b). Moreover, strong CTLs were induced in melanoma protected mice recognizing αGal$^{(-)}$ B16. In addition, vaccination with B16 melanoma cells expressing αGal epitopes prevented tumor development (LaTemple et al. 1999). This data supports the hypothesis that cancer vaccines expressing TAAs against which the animal is naturally tolerized can bypass or break that tolerance towards tumor antigens and induce a potent cellular immune response to those TAAs when modified to express αGal epitopes, and administered to an animal with high titers of anti-αGal antibodies.

Natural anti-αGal antibodies are of polyclonal nature and synthesized by 1% of circulating B cells. They are present in serum and human secretions and represented by IgM, IgG and IgA classes. The main epitope recognized by these antibodies is the αGal epitope (Galα1-3Galβ1-4NAcGlc-R) but they can also recognize other carbohydrates of similar structures such as Galα1-3Galβ1-4Glc-R, Galα1-3Galβ1-4NAcGlcβ1-3Galβ1-4Glcβ-R, Galα1-3Glc (melibiose), α-methyl galactoside, Galα1-6Galα1-6Glcβ(1-2)Fru (stachyose), Galα1-3 (Fucα1-2)Gal-R (Blood B type epitope), Galα1-3Gal and Galα1-3Gal-R (Galili et al. 1987; Galili et al. 1985; Galili et al. 1984). Similarly, non-natural synthetic analogs of the αGal epitope have been described to bind anti-αGal antibodies and their use has been proposed to deplete natural anti-αGal antibodies from human sera in order to prevent rejection of xenogeneic transplants (Janczuk et al. 2002; Wang et al. 1999). Therefore, glycomimetic analogs of the αGal epitope could also be used to promote the in vivo formation of immunocomplexes for vaccination purposes.

The above mentioned data suggests that in vivo formation of immunocomplexes between TAA purified proteins or TAA-derived peptides modified to express αGal or αGal glycomimetic epitopes is a viable alternative for antitumor immunotherapy. The use of purified TAA proteins or moreover, the use of immunogenic synthetic peptides derived from the sequence of TAA modified by chemical, chemoenzymatic or enzymatic addition of αGal epitopes has not been proposed before as a therapeutic alternative. This novel form of tumor vaccination would fill a need in the field of tumor immunotherapy providing new therapeutic methods and compositions that would be highly scalable, reproducible, specific and with enhanced immunogenicity.

SUMMARY OF THE INVENTION

The present invention provides vaccines, compositions and a method of vaccination with purified TAA proteins or peptides modified by addition of αGal epitopes to trigger the in vivo formation of immunocomplexes between αGal$^{(+)}$-TAA and natural anti-αGal antibodies. Modification of TAA epitopes with αGal increases their immunogenicity by a mechanism that relies in enhanced FcγR-mediated capture of TAA-anti-αGal immunocomplexes by APCs, activation and maturation of DCs, and antigen presentation in the context of both MHC-I and MHC-II molecules, thereby eliciting a humoral and cellular immune response against the unmodified αGal$^{(-)}$ TAA present in tumor cells.

In one embodiment of the invention, TAA proteins are modified by addition of αGal epitopes either by expression of the TAA gene in a cell that naturally expresses an active copy of the αGT gene or by expression of the TAA in a cell that has been genetically engineered to express αGT.

In one embodiment, the gene sequence encoding the protein of a TAA that does not normally traffick through the Golgi is modified to include an N-terminal ER/Golgi, secretory or plasma membrane localization signal.

In another embodiment, the gene sequence encoding the TAA protein that is expressed in an αGal$^{(+)}$ cell is modified to encode an amino acid sequence tag fused to the TAA amino acid sequence in order to facilitate its subsequent purification by affinity chromatography or immunoprecipitation.

In a preferred embodiment, the purification of αGal$^{(+)}$ TAA also includes a second affinity purification step by affinity chromatography or immunoprecipitation with anti-αGal antibodies or IB4 lectin from *Griffonia simplicifolia*.

In an alternative strategy, addition of αGal epitopes to purified TAA proteins is performed in vitro by enzymatic, chemo-enzymatic or chemical methods. In another embodiment, αGal epitopes are chemically added in vitro to TAA-derived synthetic peptides comprising the following structural elements: 1) a sequence of 1-20 amino acids at its amino terminus that contains the acceptor amino acids for the αGal epitopes, 2) a central 7-15 amino acid sequence of a TAA epitope known to elicit an immunogenic CD4+ or CD8+ T cell response, and 3) an optional sequence of 1-20 amino acids at the C-terminus that contains acceptor amino acids for addition of αGal epitopes.

In all previous embodiments, αGal epitopes can also be substituted by glycomimetic epitopes of different chemical structure than αGal that also bind to natural anti-αGal antibodies.

In the present invention, the purpose of modification of peptides or proteins with αGal epitopes is to mediate the in vivo formation of immunocomplexes with natural anti-αGal antibodies. There is no conceptual limitation in the identity of the TAA and therefore, these vaccines can be designed using any TAA protein or peptide sequence, as long as the TAA protein or peptides are expressed by the target tumor and presented in the context of HLA class I molecules.

In summary, it is an object of this invention to develop a therapeutic cancer vaccine by modification of purified TAA proteins or TAA-derived synthetic peptides by chemical, enzymatic or chemo-enzymatic modification to introduce αGal epitopes or αGal glycomimetic epitopes, in order to allow for enhanced antigen opsonization by natural anti-αGal antibodies to stimulate TAA capture and presentation, thereby inducing a humoral and cellular immune response to the TAA expressed by a tumor.

It is a further object of this invention to provide therapeutic pharmaceutical compositions comprising αGal-modified TAA proteins or αGal-modified TAA synthetic peptides.

It is a further object of the invention to provide vaccines, compositions and methods for treatment of tumors, neoplastic cells or other cells, which grow and evade the cellular and humoral immune response.

Other objects of the invention will become apparent from the description of the invention which follows.

DEFINITIONS

Various terms relating to the vaccines, compositions and methods of the present invention are used herein above and also throughout the specification and claims.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

The term "α-(1,3) Galactosyl Transferase encoding sequence", or "αGT encoding sequence" or "functional α(1,3)galactosyl transferase" refers to any polynucleotide sequence which encodes a protein that forms α-galactosyl (αGal) epitopes by the following reaction:

Galβ(1,4)GlcNAc-R+UDP-Gal→Galα(1-3)Galβ(1,4)GlcNAc-R+UDP

This can include variants, modifications, truncations and the like as well as enzymes from different animal species known to those of skill in the art and available in Genbank, other publications or databases which retain the enzymatic function of the aforementioned reaction.

The term "αGal epitope" refers to any glycosydic structure composed of at least two monosaccharydes units, the first one being a galactosyl or substituted galactosyl residue covalently bond in an α(1-3) bond conformation to a second galactosyl or substituted galactosyl residue, wherein that epitope is recognized by anti-αGal antibodies, including αGal glycomimetic epitopes.

For glycosidic structures, the terms "αGal glycomimetic variant" or "αGal glycomimetic analogs" or "αGal mimotopes" are defined as any glycosidic structure, disaccharide, trisaccharide, tetrasaccharide, pentasaccharide or higher order saccharide structure, branched or linear, substituted or unsubstituted by other chemical groups, that is recognized in an ELISA by anti-αGal antibodies. For the purpose of this definition, the scope of the specificity of anti-αGal antibodies encompasses all antibodies that can be purified by affinity in a column comprising HSA-αGal or BSA-αGal, wherein the αGal epitope bound to HSA or BSA is the Galα1-3Galα1-4Glc-R trisaccharide plus any linker.

The term "alkyl" as used herein, means a straight or branched chain hydrocarbon containing from 1 to 30 carbon atoms. As used herein, a substituted alkyl refers to molecules in which carbon atoms in the alkyl chain have been replaced by O, N or S and one or more hydrogen groups have been replaced by hydroxyl, alkyl, amino, carbonyl or sulphydryil. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "animal" as used herein should be construed to include all anti-αGal synthesizing animals including those which are not yet known to synthesize anti-αGal. For example, some animals such as those of the avian species, are known not to synthesize αGal epitopes. Due to the unique reciprocal relationship among animals which synthesize either anti-αGal or αGal epitopes, it is believed that many animals heretofore untested in which αGal epitopes are absent may prove to be anti-αGal synthesizing animals. The invention also encompasses these animals.

The term "antibody" includes reference to antigen binding forms of antibodies (e.g., Fab, F(ab)2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "anti-αGal" includes any type or subtype of immunoglobulin recognizing an αGal epitope and/or their glycomimetic variants, of any subtype such as IgG, IgA, IgE or IgM anti-αGal antibody. For the purpose of this definition, the scope of the specificity of anti-αGal antibodies encompasses all antibodies that can be purified by affinity in a chromatography column comprising HSA-αGal or BSA-αGal, wherein the αGal epitope bound to HSA or BSA is the Galα1-3Galβ1-4Glc-R trisaccharide.

As used herein, the term "antigen" is meant any biological molecule (proteins, peptides, lipoproteins, glycans, glycoproteins) that is capable of eliciting an immune response against itself or portions thereof, including but not limited to, tumor associated antigens and viral, bacterial, parasitic and fungal antigens.

As used herein, the term "antigen presentation" refers to the biological mechanism by which macrophages, dendritic cells, B cells and other types of antigen presenting cells process internal or external antigens into subfragments of those molecules and present them complexed with class I or class II major histocompatibility complex or CD1 molecules on the surface of the cell. This process leads to growth stimulation of other types of cells of the immune system (such as CD4+, CD8+, B and NK cells), which are able to specifically recognize those complexes and mediate an immune response against those antigens or cells displaying those antigens.

The term "chemical" with reference to the addition of an αGal epitope shall mean that addition of an αGal epitope by means other than the use of the enzyme αGT.

A "clone" is a population of cells derived from a single cell or common ancestor by mitosis. A "cell line" is a clone of a primary cell that is capable of stable growth in vitro for many generations.

A "coding sequence" or "coding region" refers to a nucleic acid molecule having sequence information necessary to produce a gene product, when the sequence is expressed.

The term "conservatively modified variants" applies to both amino acid and nucleic acid sequences and is intended to be included whenever a reference to a specific sequence is made. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

We define the "percentage of sequence identity" of two amino acid sequences as the number of identical amino acids shared by these two amino acid sequences after a pairwise alignment divided by the total length of the shortest sequence of the pair.

We define the "percentage of sequence similarity" of two amino acid sequences as the number of identical amino acids plus conservative amino acid substitutions shared by these two sequences after a pairwise alignment, divided by the total length of the shortest sequence of the pair.

By "encoding", "encodes" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

The terms "MHC" (Major Histocompatibility Complex) or "HLA" (Human Leukocyte Antigen) refer to the histocompatibility antigens of mouse and human, respectively. Herein, MHC of HLA are used indistinctly to refer to the histocompatibility antigens, without a species restriction, and teachings referring to MHC also apply to HLA and viceversa.

When the nucleic acid is prepared or altered synthetically, advantage can be taken of known codon preferences of the intended host where the nucleic acid is to be expressed.

By "host cell" is meant a cell which contains a vector and supports the replication and/or expression of the vector. Host cells may be prokaryotic cells such as *E. coli*, or eukaryotic cells such as yeast, insect, amphibian, or mammalian cells.

With respect to proteins or peptides, the term "isolated protein (or peptide)" or "isolated and purified protein (or peptide)" or isolated TAA protein" is sometimes used herein. This term may refer to a protein that has been sufficiently separated from other proteins with which it would naturally be associated, so as to exist in "substantially pure" form. Alternatively, this term may refer to a protein produced by expression of an isolated nucleic acid molecule.

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eukaryote. An "isolated nucleic acid molecule" may also comprise a cDNA molecule. With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). Transfection is usually referred to introduction of DNA by physico-chemical means. Transduction is usually referred to introduction of DNA into a cell mediated by a viral or phage vector.

As used herein, "mimotope" refers to molecular variants of certain epitopes that can mimic the immunologic properties of said epitopes in terms of its binding to the same antibodies or being recognized by the same MHC molecules or T cell receptors.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA". Such a nucleic acid construct may contain a coding sequence for a gene product of interest, along with a selectable marker gene and/or a reporter gene.

The term "opsonization" of an antigen or a tumor cell is meant binding of the anti-αGal epitopes present in the antigen or on the surface of a tumor cell by anti-αGal antibodies thereby enhancing phagocytosis of the opsonized antigen or tumor cell by macrophages, dendritic cells, B cells or other types of antigen presenting cells through binding of the Fc portion of the antibodies to the FcγR receptors present on the surface of antigen presenting cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement other transcription control elements (e.g. enhancers) in an expression vector.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

As used herein, "polynucleotide" makes reference to a deoxyribo-polynucleotide

The term "peptide" refers to a polymer of 2-50 amino acids. Peptides can be derived from proteolytic cleavage of a larger precursor protein by proteases, or can be chemically synthesized using methods of solid phase synthesis. Synthetic peptides can comprise non-natural amino acids, such as homoserine or homocysteine to serve as substrates to introduce further chemical modifications such as chemical linkers or sugar moieties. In addition, synthetic peptides can include derivatized glyco-aminoacids to serve as precursors of glycopeptides containing the αGal epitope or its glycomimetic variants.

The terms "protein" or "polypeptide" are used interchangeably herein to refer to a polymer of amino acid residues larger than 50 amino acids. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids. The terms "polypeptide" and "protein" are also inclusive of modifications including, but not limited to, phosphorylation, glycosylation, lipid attachment, sulfation, gamma-carboxylation of glutamic acid residues, hydroxylation and ADP-ribosylation.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectable marker gene" refers to a gene encoding a product that, when expressed, confers a selectable phenotype such as antibiotic resistance on a transformed cell.

A "signal peptide" is a peptide chain (approximately 3-60 amino acids long that directs the post-translational transport of a protein. Signal peptides may also be called "targeting signals", "signal sequences", "transit peptides", or "localization signals". The amino acid sequences of signal peptides direct proteins (which are synthesized in the cytosol) to different subcellular localizations such as the nucleus, mitochondrial matrix, endoplasmic reticulum (ER) and peroxisome. Some signal peptides are cleaved from the protein by signal peptidase after the proteins are transported. Proteins that contain an ER/Golgi localization signal traverse through the ER and they can be retained at the ER, at the Golgi, at the plasma membrane or secreted, depending on additional localization/retention amino acid sequence signals.

The term "therapeutically effective amount" is meant an amount of treatment composition sufficient to elicit a measurable decrease in the number, quality or replication rate of previously existing tumor cells as measurable by techniques including but not limited to those described herein.

The term "tumor cell" refers to a cell which is a component of a tumor in an animal, or a cell which is determined to be destined to become a component of a tumor, i.e., a cell which is a component of a precancerous lesion in an animal, or a cell line established in vitro from a primary tumor. Included within this definition are malignant cells of the hematopoietic system which do not form solid tumors such as leukemias, lymphomas and myelomas.

The term "tumor" is defined as one or more tumor cells capable of forming an invasive mass that can progressively displace or destroy normal tissues.

The term "malignant tumor" refers to those tumors formed by tumor cells that can develop the property of dissemination beyond their original site of occurrence.

The term "Tumor Associated Antigens" or "TAA" refers to any protein or peptide expressed by tumor cells that is able to elicit an immune response in a subject, either spontaneously or after vaccination. TAAs comprise several classes of antigens: 1) Class I HLA restricted cancer testis antigens which are expressed normally in the testis or in some tumors but not in normal tissues, including but not limited to antigens from the MAGE, BAGE, GAGE, NY-ESO and BORIS families; 2) Class I HLA restricted differentiation antigens, including but not limited to melanocyte differentiation antigens such as MART-1, gp100, PSA, Tyrosinase, TRP-1 and TRP-2; 3) Class I HLA restricted widely expressed antigens, which are antigens expressed both in normal and tumor tissue though at different levels or altered translation products, including but not limited to CEA, HER2/neu, hTERT, MUC1, MUC2 and WT1; 4) Class I HLA restricted tumor specific antigens which are unique antigens that arise from mutations of normal genes including but not limited to β-catenin, α-fetoprotein, MUM, RAGE, SART, etc; 5) Class II HLA restricted antigens, which are antigens from the previous classes that are able to stimulate CD4+ T cell responses, including but not limited to member of the families of melanocyte differentiation antigens such as gp100, MAGE, MART, MUC, NY-ESO, PSA, Tyrosinase; and 6) Fusion proteins, which are proteins created by chromosomal rearrangements such as deletions, translocations, inversions or duplications that result in a new protein expressed exclusively by the tumor cells, such as Bcr-Abl.

The term "TAA-derived peptides" refer to amino acid sequences of 5, 6, 7, 8, 9, 10, 11, 12, 13, 14, 15, 16, 17, 18, 19 or 20 amino acids that bind to MHC (or HLA) class I or class II molecules, and that have at least 70% amino acid identity sequence with an amino acid sequence contained within the corresponding TAA. Peptide sequences which have been optimized for enhanced binding to certain allelic variants of MHC class I or class II are also included within this class of peptides. In one embodiment, the TAA peptides further comprise at least one or more αGal acceptor amino acids and/or an affinity purification tag. In another embodiment, αGal acceptor amino acids flank the TAA peptide.

Transcriptional and translational control sequences are DNA regulatory sequences, such as promoters, enhancers, polyadenylation signals, terminators, and the like, that provide for the expression of a coding sequence in a host cell.

A cell has been "transformed", "transfected" or "transduced" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

As used herein, "vaccine" refers to any antigenic composition used to elicit an immune response. The antigenic composition can be unmodified peptides, glycosylated peptides, purified or recombinant proteins or whole cells or cell fractions. A vaccine can be used therapeutically to ameliorate the symptoms of a disease, or prophylactically, to prevent the onset of a disease.

The term "treat" or "treating" with respect to tumor cells refers to stopping the progression of said cells, slowing down growth, inducing regression, or amelioration of symptoms associated with the presence of said cells.

A "vector" is a replicon, such as plasmid, phage, cosmid, or virus to which another nucleic acid segment may be operably inserted so as to bring about the replication or expression of the segment.

The term "xenogeneic" refers to a cell or protein that derives from a different animal species than the animal species that becomes the recipient animal host in a transplantation or vaccination procedure.

The term "allogeneic" refers to a cell or protein that is of the same animal species but genetically different in one or more genetic loci as the animal that becomes the "recipient host". This usually applies to cells transplanted from one animal to another non-identical animal of the same species, or to vaccination of an animal with a protein or antigen from a different strain which may contain differences in the amino acid sequence or post-translational modifications.

The term "syngeneic" refers to a cell or protein which is of the same animal species and has the same genetic or amino acid sequence composition for most genotypic and phenotypic markers as the animal who becomes the recipient host of that cell line in a transplantation or vaccination procedure. This usually applies to cells transplanted from identical twins or may be applied to cells transplanted between highly inbred animals.

DETAILED DESCRIPTION OF THE INVENTION

Figures 1A, 1B:
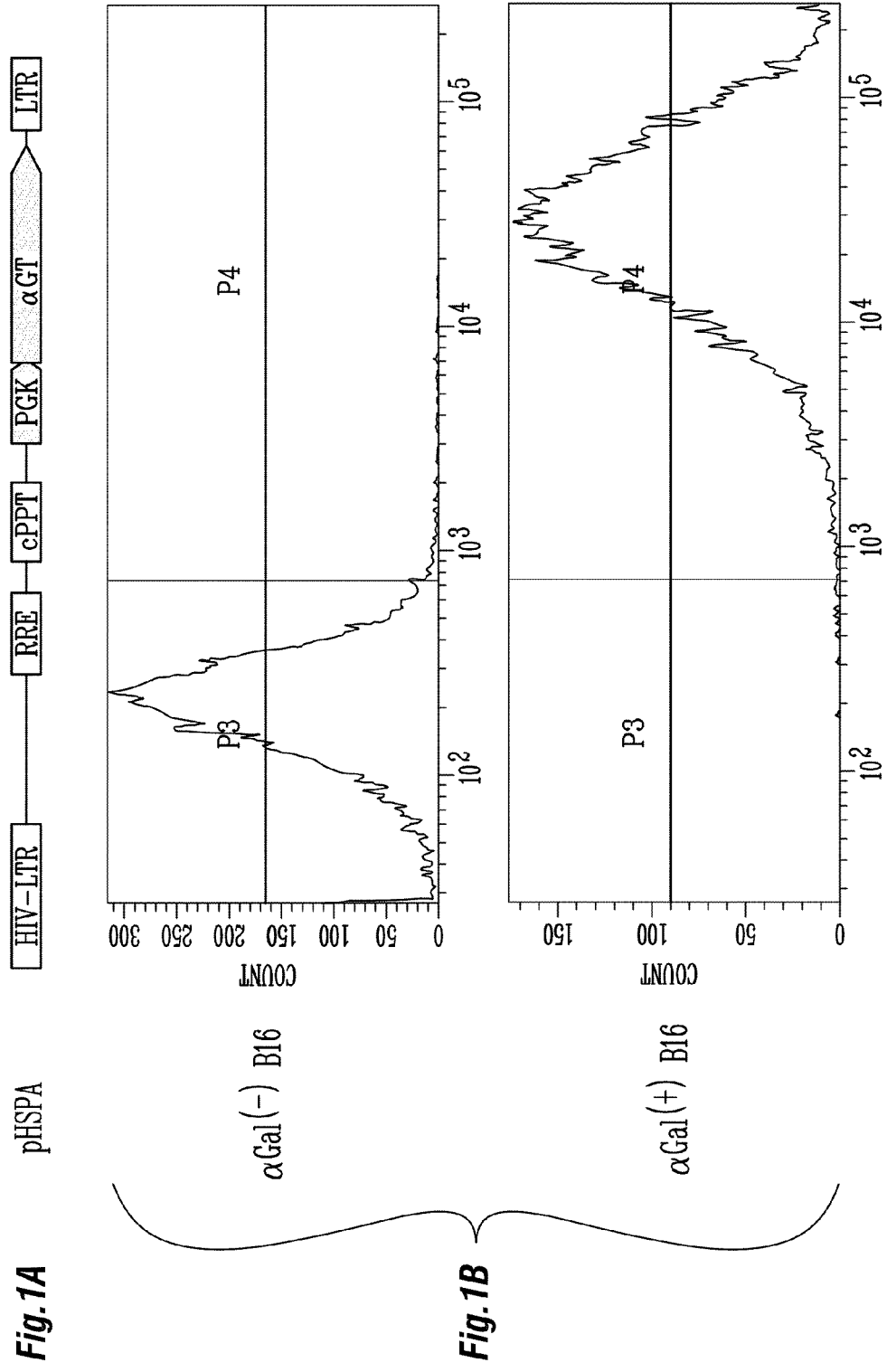
FIG. 1A is a schematic of the structure of lentiviral vector pHSPA, driving the expression of murine αGT under the control of the human PGK promoter.
FIG. 1B shows the generation of αGal$^{(+)}$ B16 cells. αGal$^{(-)}$ B16 cells were transduced with vector HSPA, stained with IB4 lectin and sorted by FACS. FACS histograms show the staining of αGal$^{(-)}$ B16 (top panel) and sorted αGal$^{(+)}$ B16 (lower panel) stained with FITC-labeled IB4 lectin.

Tumor cells express antigens that can be recognized by the host's immune system. Endogenous TAA are degraded in the proteasome into 8-11 amino acid peptides which bind to the MHC class I. Each allelic MCH variant binds only a subset of peptides that share conserved amino acid residues at each position. The peptide-MHC complex is recognized by the T cell receptor (TCR) on the surface of T lymphocytes. Therefore, an exquisite level of specificity is achieved by presentation of certain peptides in the context of specific MHC classes and allelic variants that are recognized only by certain TCR molecules.

The basic rationale for immune therapy against tumors is the induction of an effective and specific immune response against tumor-associated antigens (TAA), which in turn results in immune-mediated destruction of proliferating tumor cells expressing these antigens.

Effective prophylactic or therapeutic vaccines based on TAA proteins or peptides have several requirements. First, the epitopes present in the vaccine have to be present in TAAs expressed by the tumor. Second, the epitopes have to be effectively presented in the context of the right MHC alleles of the patient. Third, the vaccinating antigens must be properly captured, processed and presented by antigen presenting cells (APC) such as macrophages, dendritic cells and B cells. Within APCs, TAAs are degraded in the lysosomal compartment and the resulting peptides are expressed on the surface of the APC membrane mostly in association with MHC Class II molecules and also in association with MHC class I molecules if the antigen traversed the cross-presentation pathway. This expression mediates recognition by specific CD4+ helper T cells or CD8+ effector T cells and subsequent activation of these cells to effect the immune response (Lanzavecchia 1993; Pardoll 1993).

Great challenges have to be overcome to achieve an effective immunization using TAA proteins or peptides. Most tumor cells have unique expression profiles of TAA, and in many cases the immunogenic peptides include a mutated amino acid sequence that confers immunogenicity through the exposure of an altered nonself epitope. These epitopes are usually very immunogenic. However, many tumors escape immune surveillance either 1) by not-generating these epitopes during proteasome processing, or 2) by down regulating the expression of MHC components such as β-microglobulin, or 3) because the immune system does not recognize these TAA as foreign antigens because either they are not presented in the context of a cellular "danger" signal, or 4) because the immune system has been tolerized to those antigens and recognizes them as "self" antigens. Immunotherapeutic approaches based on T-cell recognition of TAA-derived peptides are not expected to work using any vaccination approach for the two first cases (i.e. when the tumor does not present the antigenic TAA), but are well suited for the last two cases (i.e. when the immune system does not recognize the TAA as immunogenic).

One of the reasons for the lack of a sufficient immune response to control cancer growth in vivo is due to the poor immunogenicity of natural epitopes expressed by tumor cells. With the exception of the immunodominant melanoma Melan-A/MART1$_{27-35}$ and gp100 peptides, which readily activate specific T cells in vitro (Rivoltini et al. 1995) and in vivo (Cormier et al. 1997), most T-cell responses require repeated in vitro stimulation with TAA epitopes and show limited immunogenicity when used as vaccines for cancer patients (Marchand et al. 1999; Weber et al. 1999). New strategies for increasing in vivo immunogenicity consist of modifying the peptide sequence at amino acid residues to: 1) improve the interaction with the HLA or with the specific TCR, 2) inhibit dimerization, 3) reduce or inhibit proteolytic degradation (Brinckerhoff et al. 1999; Chen et al. 2000; Parkhurst et al. 1996; Tourdot et al. 2000). In addition, caution should be taken when designing vaccines based on peptide immunization as under certain circumstances, vaccination with peptides may induce epitope specific T-cell tolerization rather than activation, depending on the adjuvant used and route of immunization.

One possible explanation for the limited therapeutic efficacy of TAA peptide vaccination lies in the fact that activation of peptide-specific CTL responses requires the delivery of inflammatory signals from monocytes, lymphocytes, or granulocytes recruited at the site of vaccination. Those signals may or may not be provided by standard adjuvants like incomplete Freund's adjuvant. An efficient activation signal, however, may be provided by natural adjuvants that trigger a "danger" signal such as bacterial DNA or synthetic oligodeoxynucleotides (ODN) containing unmethylated CpG dinucleotides (CpG-ODN). Such signals can stimulate B cells, natural killer (NK) cells, T cells, monocytes, and antigen-presenting cells; more importantly, such signals can promote maturation of DCs, a step that will result in the activation of the antibody and cell-mediated immune responses (Brunner et al. 2000; Sparwasser et al. 1998). More recently, CpG-ODN have been shown to improve the antitumor activity of antigen-presenting cells loaded with TAA peptides and promote a 10-fold to 100-fold increase in the induction of CTL responses to peptide immunization (Brunner et al. 2000).

Another possible reason of poor results obtained through peptide vaccination is the exclusive focusing on peptide epitopes that bind to MHC class I molecules to trigger CTL immune response. Peptide epitopes that trigger a CD4+ T cell response also result in stimulation and activation of B cells, leading to a humoral response against TAA.

There are several theoretical reasons that justify why a strong humoral immune response should produce a more effective anti-tumor response. In fact, passive administration of antibodies against gp75 prevents development of melanoma metastases in a mouse model (Clynes et al. 1998). The binding of antibodies to TAA promotes the formation of immunocomplexes, which bind to the FcγR receptors on APCs. Fc receptor targeting accomplishes several important functions for effective vaccine performance including promoting the efficient uptake of antigen for both MHC Class I and II antigenic presentation; promoting APC activation and maturation of dendritic cells. APCs that ingest a tumor cell must be activated before they can effectively present antigen. Otherwise, presenting antigens to immature APCs, without the required activation signals, can suppress the immune response. Second, the uptake of opsonized TAA, or TAA-expressing cells by antigen presenting cells via FcγR receptor mediated endocytosis may be critical to generating an effective anti-tumor CTL response since it promotes the activation of MHC class I restricted responses by CD8+ T-cells through a cross-presentation pathway. Third, vaccines that cannot stimulate a humoral immune response are limited in their ability to induce cellular immunity by HLA restriction. CTLs are HLA restricted and will only destroy the tumor cells that present TAAs on self-class I MHC molecules. On the contrary NK cells will destroy the tumor vaccine cells if they are opsonized by antibodies by antibody-dependent cell cytotoxicity (ADCC).

The present invention provides methods and composition for peptide vaccines that contemplate the aspects mentioned above and overcomes some of the current limitations associated with the development of TAA protein or peptide vaccines. In the present invention, TAA proteins or TAA-derived peptides are modified by functionalization with a αGal epitope which promotes the in vivo formation of immunocomplexes with natural anti-αGal antibodies. This provides several immunologic advantages over the use of other vaccines composed of TAA proteins or peptides (with or without adjuvant), which do not promote the in vivo formation of immunocomplexes.

First, the binding of natural anti-αGal IgG or IgM to αGal epitopes present in the immunizing TAA molecule facilitates the formation of immunocomplexes, which triggers complement activation and opsonization of the immunocomplex by C3b and C3d molecules, which can target the immunocomplex to follicular dendritic cells and B cells via CD21 and CD35, thereby augmenting the immune response. Also, FcγR receptor mediated phagocytosis of IgG immunocomplexes by DCs is a very efficient mechanism of antigen uptake and processing. Second, complement-activation at the site of vaccination generates a "danger signal" which has numerous implications for the kind of immune response that will be generated (Matzinger 2002; Perez-Diez et al. 2002). Danger signals are recognized as crucial components for APC activation and differentiation to mature DCs. Additionally, complement activation has chemo-attractant properties that, similarly to GM-CSF, result in inflammation and recruitment of APCs.

Different antigen uptake and processing pathways control the presentation of antigenic peptides by either MHC class I molecules to CD8+ T cells (endogenous pathway) or MHC class II molecules to CD4+ T cells (exogenous pathway). Vaccines that are composed of exogenous antigens use mainly the exogenous pathway for the delivery of antigen to APCs. This, in turn, favors the stimulation of CD4+ T cells and the production of antibodies. To deliver exogenous antigens to the endogenous pathway in order to elicit a cellular mediated response, the engagement of the FcγR receptor to mediate antigen uptake of immunocomplexes is very important as it stimulates the cross-presentation pathway (Heath and Carbone 2001). Studies indicate that, in addition to classical CD4+ priming, antigen acquired through endocytosis by DC through FcγR results in the induction of T cell effector immunity resulting in $T_H1$ and class I restricted CD8+ T cell priming. Furthermore, engagement of FcγR also induces DC activation and maturation. Thus, the existing evidence indicates that antigenic targeting to FcγR on DC accomplishes several important aspects of T cell priming important for induction of an immune response: facilitated uptake of antigen, class I and class II antigen presentation and induction of DC activation and maturation.

In the specific case of αGal$^{(+)}$ TAA vaccines of the present invention, three mechanisms of antigen uptake are expected to take place. First, the exogenous pathway involving phagocytosis/pinocytosis that sends the antigens through the endosomal/lysosomal pathway which results in presentation of the processed antigen in the context of MHC class II surface molecules that activate the proliferation of CD4+ helper T cells. Second, FcγR-mediated antigen uptake of immunocomplexes involving anti-αGal antibodies will favor the cross-presentation pathway, resulting in antigen presentation in the context of MHC class I molecules, which will preferentially activate CD8+ cytotoxic T cells. Third, binding of tumor specific antigen molecules to membrane IgM present in naïve B-cells will result in B-cell activation and differentiation, and also in MHC class II antigen presentation that further stimulates proliferation of memory CD4+ T-cells that recognize those antigens. After activation and stimulation B-cells proliferate, differentiate and produce antibodies which bind to surface TAA molecules present on the target tumor cells, facilitating killing of the cell by complement-mediated cell lysis, antibody dependent cell cytotoxicity and FcγR-dependent phagocytosis. Also, target cell destruction is mainly achieved by cytotoxic CD8+ T cells previously activated by differentiated dendritic cells and helper CD4+ T cells. In summary, a main advantage of the αGal$^{(+)}$ TAA vaccines of the present invention over previous TAA protein or peptide vaccines is that it achieves the in vivo formation of immunocomplexes in the absence of adjuvant. This leads to recruitment of antigen presenting cells, increased FcγR-mediated phagocytosis and antigen uptake that result in activation of both cellular and humoral branches of the immune response. The stronger initial immune reaction is expected to induce both a more effective immunity and the generation of a larger pool of memory cells. Therefore, taking advantage of the strong innate immune response to α-galactosylated proteins establishes a firm basis for novel antitumor and antiviral immunotherapies.

Theoretically, there is no limitation in the identity or properties of the TAA used for vaccination. A vast list of TAA has been compiled by Renkvist et al. (Novellino et al. 2005; Renkvist et al. 2001). All the TAA antigens cited in these publications are suitable for the method and compositions of the present invention and are incorporated herein by reference. Similarly, portions of the full length TAA amino acid sequences or their isoforms are well suited for the purposes of antitumor vaccination described in this invention.

Tumors which may be treated in accordance with the present invention include malignant and non-malignant tumors. Malignant (including primary and metastatic) tumors which may be treated include, but are not limited to, those occurring in the adrenal glands; bladder; bone; breast; cervix; endocrine glands (including thyroid glands, the pituitary gland, and the pancreas); colon; rectum; heart; hematopoietic tissue; kidney; liver; lung; muscle; nervous system; brain; eye; oral cavity; pharynx; larynx; ovaries; penis; prostate; skin (including melanoma); testicles; thymus; and uterus. Examples of such tumors include apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, Merkel cell, mucinous, non-small cell lung, oat cell, papillary, scirrhous, bronchiolar, bronchogenic, squamous cell, and transitional cell), plasmacytoma, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's experimental, Kaposi's, and mast-cell), neoplasms and for other such cells.

In one embodiment of the invention, TAA proteins are modified by addition of αGal epitopes by expression in cultured cells. This can be accomplished by several means. In a preferred embodiment, recombinant TAA proteins are expressed in eukaryotic cells that naturally express an active copy of the gene encoding for αGT. These cell lines can be derived from any mammalian species except the catharrine primates such as apes, humans or Old World monkeys that do not express αGT. Expression of αGT and presence of αGal epitopes can be confirmed by staining cells with *Griffonia simplicifolia* IB4 lectin or with purified anti-αGal antibodies and subsequent analysis by FACS. There are numerous examples in the literature of vector systems for the expression of recombinant proteins in mammalian cells (Schmidt 2004).

In an alternative embodiment, recombinant TAA proteins are expressed in a eukaryotic cell line that has been genetically modified to express the gene encoding a functional αGT enzyme. αGT has been cloned from several mammalian species such as mouse, bovine, sheep, porcine, cat, dog and marmoset (Henion et al. 1994; Joziasse et al. 1989; Joziasse et al. 1992; Koike et al. 2002; Strahan et al. 1995a; Strahan et al. 1995b; Taylor et al. 2003). Stable transfectants of mammalian cells can be obtained by stable transfection with plasmid DNA or by stable transduction with viral vectors encoding αGT under the control of a constitutive or inducible promoter. Viral vectors suitable for this transfection comprise the use of retroviral vectors such as Moloney murine retrovirus or human, simian, feline or equine lentiviral vectors by methods well described in the art (Phillips 2002).

In an alternative embodiment, the TAA protein can be expressed in a genetically engineered yeast cells such as *Saccharomyces cerevisiae* or *Pichia pastoris*, modified to express a recombinant αGT, such as the one described by Shao et al. (Shao et al. 2003).

Addition of αGal epitopes to recombinant TAA protein expressed in a eukaryotic cell that also expresses a functional copy of αGT requires that the TAA protein trafficks through the Golgi via the excretory/secretory pathway in order to become glycosylated with αGal epitopes. αGT localizes to the Golgi and catalyzes the transfer of UDP-Gal to a lactosaminyl or N-acetylylactosaminyl acceptor that is part of N-linked or O-linked oligosaccharide structures. N-Linked glycans are linked to the protein backbone via an amide bond to asparagine residues in an Asn-X-Ser/Thr motif, where X can be any amino acid, except Pro. O-Linked glycans are linked to the hydroxyl group of serine or threonine. Therefore, in order to effect the in vivo addition of αGal epitopes to a recombinant TAA protein, this protein has to satisfy the following requirements: 1) possess an N-terminal ER/Golgi localization, Golgi trafficking, secretory or plasma membrane localization signal, 2) possess a consensus for N-glycosylation or exposed Ser/Thr amino acids in hydrophilic loops of the protein for O-glycosylation.

In a preferred embodiment, the recombinant TAA encoding gene is modified to allow its encoded protein to be glycosylated and secreted through the secretory pathway, into the cell culture medium, thereby facilitating extraction and purification of the αGal-modified TAA from the growth medium. In the case of TAA derived from membrane glycoproteins, expression of the soluble extracellular glycoprotein domain by truncation of the membrane anchoring domain(s) and inclusion of secretory signals would allow to recover the αGal⁽⁺⁾ TAA soluble domain in the cell culture medium. This embodiment would facilitate continuous culture and production of αGal⁽⁺⁾ TAA protein. Alternatively, the αGal⁽⁺⁾ TAA recombinant protein can be purified from lysed cells following protein purification protocols suitable for each specific protein.

A few examples of ER/Golgi-localization or secretory signals include the following amino acid sequences and conservative variants thereof:

| | | |
|---|---|---|
| 1] | MRVLVLALAVALAVGDQSNLG [U.S. Pat. No. 6,733,997] | (SEQ ID NO: 15) |
| 2] | MKWVTFLLLLFISGSAFSR [Preproalbumin] | (SEQ ID NO: 16) |
| 3] | MDMRAPAQIFGFLLLLFPGTRCD [Pre-IgG light chain] | (SEQ ID NO: 17) |
| 4] | MRSLLILVLCFLPLAALGK [Prelysozyme] | (SEQ ID NO: 18) |
| 5] | MMSFVSLLLVGILFWATDADNLTKCDVFN | (SEQ ID NO: 19) |
| 6] | MDLLLLLLLGLRLQLSLGRIP [αGT] | (SEQ ID NO: 12) |

A few examples of Golgi localization sequence signals include the following amino acid sequences and conservative variants thereof:

1] Arg-based signals with the consensus Z/Z/R-R-X-R (SEQ ID NO:82), in which Z denotes an aromatic or bulky hydrophobic residue and X represents any amino acid. More than two arginine residues gives rise to particularly strong sorting motifs, whereas the residue that precedes RXR and the identity of X itself can modulate the signal to an intermediate efficacy that results in significant steady state Golgi localization 2] C-terminal -K(X) KXX (SEQ ID NO:83) ER-localization signals, exposed at the distal terminus of a membrane protein.

Several methods can be used to purify the αGal⁽⁺⁾ TAA recombinant protein from cell lysates or from the cell culture medium. A common approach is to modify the sequence of the gene encoding the TAA to include an affinity tag fused to the TAA protein. Examples of affinity purification tags are well known in the art and include: 1) polyhistidine tags to facilitate protein purification in a Ni$^{+2}$ column; 2) glutathion S-transferase; 3) maltose binding protein [New England Biolabs]; 4) chitin binding protein [New England Biolabs]; 5) amino acid sequence tags recognized by immobilized monoclonal antibodies, such as the V5, HA, FLAG sequences. In a preferred embodiment, such tags are included at the C-terminus of the recombinant TAA to avoid interference with the secretory sequence signals. In an alternative embodiment, the affinity purification tag is fused to the TAA recombinant protein via a protease sensitive sequence to allow separation of the sequence tag from the TAA protein.

As a single step of protein affinity purification from a complex protein mixture generally does not yield a pure protein preparation, a preferred embodiment for protein purification of αGal⁽⁺⁾ TAA is to include a second purification step based on affinity to the αGal epitope. Natural human anti-αGal antibodies or the IB4 lectin from *Griffonia simplicifolia* recognize αGal epitopes on glycoproteins. An affinity matrix column containing covalently linked anti-αGal antibodies or IB4 lectin can be used to purify the αGal⁽⁺⁾ TAA and yield a more pure TAA protein preparation.

An alternative approach to addition of αGal epitopes to TAA proteins by expression in αGal⁽⁺⁾ cells is to perform the addition of αGal epitopes in vitro. In vitro approaches use purified TAA protein or protein fragments/domains obtained from any cell expression system (bacteria, yeast, mammalian, insect cells), regardless of whether these cells express αGT or not. Subsequent addition of αGal epitopes can be performed by: 1) enzymatic methods, 2) chemo-enzymatic methods or 3) chemical modification. The preferred method of addition of αGal epitopes will be chosen depending on the cell expression system used as the source of recombinant TAA protein.

Enzymatic addition of αGal epitopes to whole cells, membrane fractions or recombinant proteins purified from mammalian cells has been described extensively by Galili et al. and those methods are incorporated herein by reference (Abdel-Motal et al. 2006; Chen et al. 2001; Galili et al. 2001; Henion et al. 1997; LaTemple et al. 1996). Briefly, when TAA glycoproteins are purified from αGal$^{(-)}$ mammalian cells, two enzymatic steps have to be performed to mediate addition of αGal epitopes. The first step is the removal of the terminal sialic acid residues from the glycosyl structures by incubation with the enzyme neuraminidase. The second step is the incubation of such protein with recombinant purified αGT and UDP-Gal to mediate the addition of Galactose in an α(1-3) configuration to N-acetyl-lactosaminyl (Galβ1-4GlcNAc-R) or lactosaminiyl (Galβ1-4Glc-R) acceptor residues. The incubation with neuraminidase can be obviated though the efficiency of incorporation of αGal epitopes increases ~5-fold after addition of this enzymatic step (Chen et al. 2001). Also, removal of sialic acid residues with neuraminidase can be performed as a first step or sequentially with αGT incubation. The αGal$^{(+)}$ TAA has to be purified from this mixture, by any of the means described above.

For instances in which the TAA protein is purified from cell expression systems based on insect or yeast cells, the glycosylation pattern will differ from the glycosylation pattern observed in TAA purified from mammalian cells. Insect cells will provide a less complex and more immature high-manose core that can be used as an acceptor to perform sequential enzymatic addition of 1) UDP-GlcNAc by N-acetyl glucosaminyl transferase I, 2) UDP-Gal by a β(1-4) galactosyl transferase and 3) UDP-Gal by αGT.

If the TAA protein or protein domain is purified from bacterial expression systems, it will not have an appropriate lactosaminyl acceptor for UDP-Gal and αGT will not be able to catalyze addition of αGal epitopes in vitro. Therefore, the chemical addition of activated αGal epitopes is the method of choice in this case.

Several methods have been described for the purely chemical, purely enzymatic or a combination of chemo-enzymatic synthesis of αGal or αGal-derivative epitopes with the purpose to inhibit binding of anti-αGal antibodies to cells expressing αGal epitopes. For example, the synthesis of the following αGal epitopes has been previously described and their methods of synthesis are incorporated by reference herein:

| 1] | Galα1-3Gal-R—NH$_2$ | (Wang et al. 1999) |
| 2] | Galα1-3Galβ1-4Glc-R—NH$_2$ | (Wang et al. 1999) |
| 3] | Galα1-3Galβ1-4Glc-N$_3$ | (Fang et al. 1998) |
| 4] | Galα1-3Galβ1-4GlcNAcβ1-3Galβ1-4Glcβ-N$_3$ | (Fang et al. 1998) |
| 5] | Galα1-3Gal-O—(CH$_2$)$_6$—NH$_2$ | (Hanessian et al. 2001b) |
| 6] | Galα1-3Galβ1-4GlcNAc—O—(CH$_2$)$_3$—NH$_2$ | (Hanessian et al. 2001b) |
| 7] | Galα1-3Galβ1-4GlcNAcβ-OBn | (Reddy et al. 1994) |
| 8] | Galα1-3Galβ1-4GlcNAcβ1-6GalNAc-α-OBn | (Reddy et al. 1994) |
| 9] | Galα1-3Galβ1-4Glc-O—(CH$_2$)$_3$—NH$_2$ | (Hanessian et al. 2001a) |
| 10] | Galα1-3Galβ1-4-R—NH$_2$ | (Hanessian et al. 2001a) |
| 11] | A trimeric cluster of Comp #10 on penta-erythritol scaffold containing a free terminal NH$_2$ group | (Hanessian et al. 2001a) |
| 12] | Galα1-3Galβ1-4Glc-O—(CH$_2$)$_2$—O—(CH$_2$)$_2$—NH$_2$ | (Naicker et al. 2004) |
| 13] | Galα1-3Galβ1-4Glc | (Shao et al. 2003) |
| 14] | Galα1-3Galβ1-4Glc-NAc—(CH$_2$)$_3$—S—(CH$_2$)$_2$—NH$_2$ | |
| 15] | Galα1-3Galβ1-4GlcNAc-SEt | |

αGal epitope compounds #1, 2, 5, 6, 9, 10, 11 and 12 have a free primary NH$_2$ group. αGal epitope compounds #3 and 4 have an azide group that can be easily converted to a primary amino group by reduction in H$_2$/Pd—C. Compound #13 is easily produced in large amount from an inexpensive source of sucrose and lactose by a genetically engineered *Pichia Pastoris* cell line (Shao et al. 2003). This trisaccharide can be functionalized with allylamine and cysteamine hydrochloride at the 1β-anomeric position by a method similar to the one described by Ramos et al. (Ramos et al. 2001) to yield compound #14 which has a primary amino group.

The primary amino group can be coupled to a bifunctional N-hydroxy-succinimide-L1-Maleimide cross-linker (NHS-R-Mal, where L1 is any type of linear linker such as but not limited to: alkyl, ether, polyether or polyamide) to yield a reactive αGal epitope. This Maleimide activated αGal molecules can be reacted to Cysteine residues in the purified TAA protein, thereby yielding a αGal$^{(+)}$ TAA protein.

Alternatively, αGal epitopes having a primary amino group can be enzymatically coupled to the γ-carboxamide residue of glutamine by bacterial glutaminyl-peptide γ-glutamyl transferase (Transglutaminase) (Ramos et al. 2001). Synthesis of compound #15 by the sequential enzymatic activity of β-galactosidase (from *Bullera singularis* or *Bacillus circulans*) and α-galactosidase (from *Aspergillus oryzae* or green coffee beans) from 1-βD-thioethylglucosamine, O-p-nitrophenyl α-D-galactopyranoside and O-p-nitrophenyl β-D-galactopyranoside has been previously described (Nilsson 1997; Vic et al. 1997). Reduction of thioethyl group to sulphydryl group leaves a free —SH group that is reactive with Maleimide-R2-NHS linkers. This activated αGal epitope can be coupled to proteins or peptides bearing primary amino groups either at the N-terminus or at lysine residues. Similarly, bifunctional NHS-R1-NHS linkers could be coupled to the free NH$_2$ group of αGal molecules (such 1, 2, 5, 6, 9, 10, 11 and 12) and then coupled to the ε-NH$_2$ group of lysines present in the TAA protein or peptides.

In a preferred embodiment, the αGal epitopes with the generic structure

αGal-L$_1$-R$_2$ are synthesized by the methods of the present invention. L$_1$ is a linker with the preferred structure —N(CH$_3$)—O—R$_1$—COO—, wherein R$_1$ is any linear or branched alkyl group of 1 to 30 carbon atoms, wherein one or more carbon atoms in such alkyl group can be substituted by O, S, or N and wherein one or more hydrogens can be substituted by hydroxyl, carbonyl, alkyl, sulphydryl or amino groups. In a more preferred embodiment, such atom substitutions create one or more ester groups situated at any position within the R$_1$ alkyl chain. R$_2$ is any functional group that is reactive to primary amino groups, sulphydryl groups or acid groups, such as N-hydroxysuccinimide, or maleimide. First, the linker of structure NH(CH$_3$)—

O—$R_1$—COOH is reacted to synthetic or semisynthetic αGal trisaccharide, such as the one purified from a genetically engineered *Pichia Pastoris* described by Shao et al, or from any commercial source. The resulting αGal-linker molecule is then activated with N-hydroxysuccinimide or maleimide, thereby yielding an activated αGal epitope that can be reacted with any primary amino group present in any lysine or cysteine residue or N-terminal amino group of any protein or peptide. The methods and compositions described here for the synthesis of αGal-$L_1$-$R_2$ activated molecules also apply for any αGal epitope and also to any monosaccharide, disaccharide, trisaccharide, tetrasaccharide and pentasaccharide. Examples of such activated αGal epitopes are compounds of the formula:

(IV)

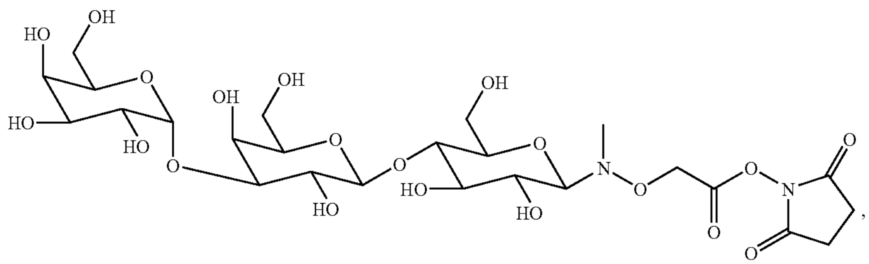

, (V)

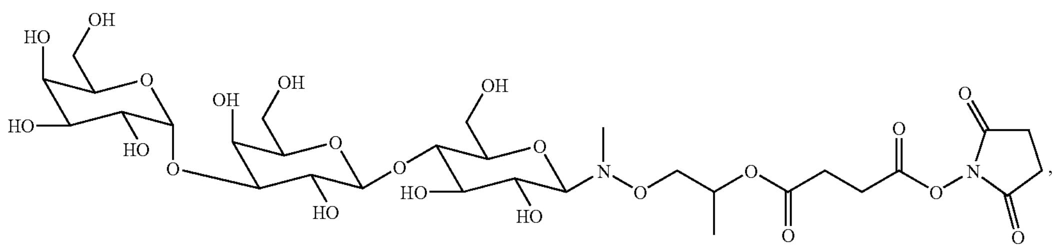

, (VI)

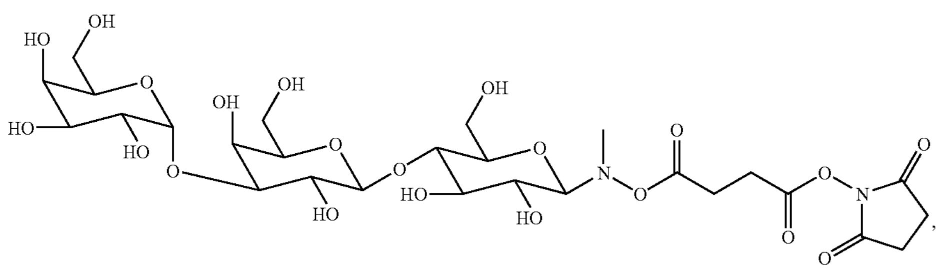

, or (VII)

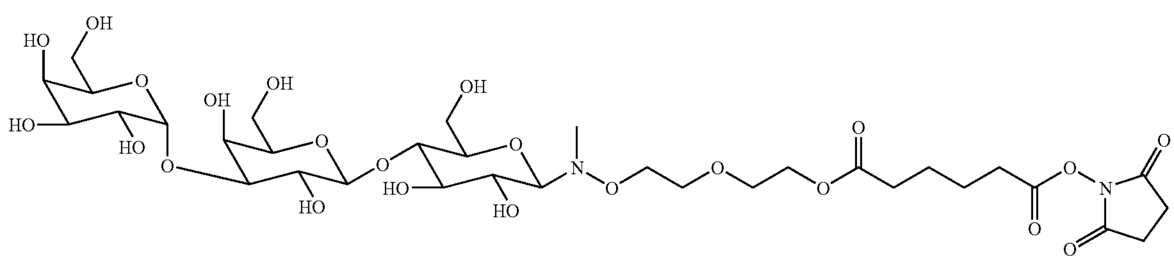

Details of the synthesis schemes and reaction conditions to obtain such compounds are provided in FIGS. 3-6 and Examples 22-32.

The above mentioned αGal epitopes could also be used to modify synthetic peptides that bear amino acids such as Cysteine, Homocysteine, Serine, Threonine or Glutamine, by post-synthesis chemical conjugation of the activated αGal epitope to the pure synthetic peptide in the same way as described for TAA proteins.

It is important to highlight the fact that αGal epitopes added by αGT will be in a different chemical context as the αGal epitopes added by chemical means. Therefore, the $\alpha Gal^{(+)}$-TAA vaccine compositions generated by chemical addition of αGal epitopes will differ from the $\alpha Gal^{(+)}$-TAA vaccine compositions generated by enzymatic addition of αGal epitopes and as such, constitute a novel chemical entity. The different chemical context to which αGal epitopes are added within a protein or peptide might affect the reactivity of different species of anti-αGal antibodies present in human serum towards the different classes of αGal epitopes. However, given the vast polyclonality of antibody species that recognize the αGal epitopes, the overall efficacy of the vaccine will not be affected by the chemical context of the αGal addition site.

In the present invention, the purpose of modification of peptides or proteins with αGal epitopes is to mediate the in vivo formation of immunocomplexes with natural anti-αGal antibodies, thereby facilitating FcγR-mediated uptake of the immunocomplex, which will ultimately lead to enhanced presentation of the deglycosylated immunogenic epitopes, thereby triggering immunity against the native TAA expressed by the tumors which is not modified with αGal. Therefore, some considerations regarding processing and presentation of glycosylated antigens are important to take into account when performing chemical modification of proteins or peptides. Glycoprotein antigens are ingested by APCs by endocytosis and transported from the cell surface toward the lysosomal compartments. During transport, proteolytic enzymes become activated as the pH of the endosome decreases. The enzymes, which include endoproteases and exoproteases with many different substrate specificities, attack and fragment the antigen into peptides (Cresswell 2005; Cresswell et al. 2005; Kloetzel 2001; Kloetzel 2004; Kloetzel and Ossendorp 2004; Kruger et al. 2003; Li et al. 2005; Rock et al. 2004). Glycans in a glycoprotein or glycopeptide can interfere with the proteolytic fragmentation and influence the pattern of T cell epitopes that are presented. Appropriate peptides (8-15 amino acids) are protected against further proteolysis as they bind to empty MHC class II molecules that are accumulating within the acidic compartments. Finally, the MHC-peptide complexes are transported to the cell surface and presented to CD4+ T cells. Due to the fact that many cellular proteins are extensively glycosylated, processing and presentation mechanisms are expected to produce a pool of major MHC-bound protein-derived peptides, part of which retain sugar moieties. It has been demonstrated that T cells are able to recognize partially glycosylated peptides that bind to the MHC molecules if the sugar moiety is small and if it is located in a central position within the peptide being presented (Speir et al. 1999; Werdelin et al. 2002). Sugar moieties present at the ends of the peptide being presented do not elicit and immune response against the glycosylated portion of the peptide. In the present invention, the objective is to elicit an immune response against deglycosylated peptides or against the non-glycosylated portion of the glycopeptides, since the target TAAs expressed by tumors do not bear the same glycosydic modification as the immunizing peptides. Since the chemical addition of αGal epitopes mediated by N-hydroxysuccinimide, Maleimide or other functional groups will not create the natural N-linked chemical bonds of sugar to Asparagine residues, or the natural O-linked sugar moieties to Serine or Threonine residues, complete removal of sugar moieties (that do not contain natural N-linked or O-linked chemical bonds) is anticipated to be impaired during antigen processing.

In a preferred embodiment, removal of the αGal epitope bound to a peptide or protein during antigen processing and presentation can be facilitated by including one or more ester groups in the linker bridging the trissacharide portion of the αGal epitope with the peptide or protein. After endocytosis, intracellular esterases of different specificities cleave the αGal epitope at the ester group present in the linker region, thereby yielding a deglycosylated peptide that can bind to the MHC class I and II and elicit an immune response by engaging with TCR present in CD4+ and CD8+ T cells.

An alternative embodiment to prevent potential difficulties associated with incomplete deglycosylation of immunizing glycopeptides is to separate the region of the peptide known to trigger an immune response against cells expressing the corresponding TAA from the region conjugated to the αGal epitope. This can be done by creating a αGal tag fused to the immunogenic peptide. The αGal tag consists of a stretch of 1 to 20 amino acids that bear the amino acids to which the αGal epitope will be covalently linked to, in addition to known endoprotease amino acid consensus sequences that will facilitate its cleavage by endosomal proteases. In this way, the αGal tag will mediate formation of immunocomplex with anti-αGal antibodies, thereby enhancing DC activation, antigen processing and presentation. The αGal tag will be released from the immunogenic portion of the peptide by proteases and aminopeptidases during antigen processing. The release of the non-glycosylated immunogenic portion of the peptide is expected to bind to the MHC-II complex or the MHC-I complex in case of cross-presentation.

Therefore, in a preferred embodiment, chemical addition of αGal epitopes is performed on amino acid residues corresponding to a "tag" region adjacent to the amino acid sequence derived from the TAA.

In another embodiment, chemical addition of the αGal epitope is performed to the N-terminal and/or C-terminal amino acid of the immunizing peptide.

For the in vivo formation of immunocomplexes between anti-αGal antibodies and αGal$^{(+)}$ TAA capable of complement activation, each C1 molecule must bind to at least two Fc sites for a stable C1 antibody interaction. Circulating IgM exists in a planar configuration and does not expose the C1q binding sites. IgM exposes its C1q binding sites after binding to an antigen on a membrane. For this reason immunocomplexes formed by anti-αGal IgM and soluble αGal$^{(+)}$ TAA will not likely activate the complement cascade. On the contrary, an IgG molecule contains only a single C1q binding site in the CH2 domain of the Fc portion of the immunoglobulin, so that stable C1q binding is achieved only when two IgG molecules are within 30-40 nm of each other in a complex, thereby providing two C1q binding sites. In order to form particulate immunocomplexes containing more than one anti-αGal IgG and one αGal$^{(+)}$ TAA molecule, each TAA molecule has to contain more than a single αGal epitope. This is easily achievable for proteins that have been chemically modified with αGal epitopes at their lysine and/or cysteine residues. However, for the particular case of αGal$^{(+)}$ TAA peptides, it is important to provide amino acids that serve as anchoring points for the chemical addition of αGal epitopes and that do not form part of the immunogenic portion of the peptide.

Therefore, in another embodiment, αGal epitopes are chemically added in vitro to synthetic peptides with a structure comprising: 1) a sequence of 1-20 amino acids at its amino terminus that contains the acceptor amino acids for the αGal epitopes, 2) a central 7-20 amino acid sequence of a TAA epitope known to elicit an immunogenic CD4+ or CD8+ T cell response, and 3) a sequence of 1-20 amino acids at the C-terminus that contains acceptor amino acids for addition of a second αGal epitope. Thus, while it is not intended that the invention be limited by the length of the αGal-modified TAA peptide, it is preferred that peptides that flank the TAA peptide of the present invention are less than twenty amino acids in length. Preferably, the flanking peptides comprises 7, 8, 9, 10, 11, 12, 13, 14, 15, 16, 17, 18, 19 or 20 amino acids, at least one of which comprises an αGal acceptor amino acid for addition of an αGal epitope. In this synthesis method the epitope is directly linked to the amino acid with no other glycosidic residues between the two, and the linkage will depend on the type of cross-linker used suchs as maleimide where the epitope is added to cysteines, or succinimide where it will be bound to lysine and the primary N-terminal amino group, or glutaraldehyde where it will bind to serine or threonine. It is postulated that these different epitope linkages will cause difference in binding capacity of anti-αGal antibodies and their capacity to form immunocomplexes. Some antibodies will bind preferentially to chemical epitope and some will bind preferentially to epitopes added naturally by αGT.

Pharmaceutical Preparations

According to the invention, purified TAA proteins, protein fragments or peptides modified to express αGal epitopes are used as either prophylactic or therapeutic vaccines to treat tumors. Thus the invention also includes pharmaceutical preparations for humans and animals comprising αGal$^{(+)}$ TAA proteins or peptides. Those skilled in the medical arts will readily appreciate that the doses and schedules of pharmaceutical composition will vary depending on the age, health, sex, size and weight of the human and animal. These parameters can be determined for each system by well-established procedures and analysis e.g., in phase I, II and III clinical trials and by review of the examples provided herein.

For administration, the αGal$^{(+)}$ TAA proteins can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like.

Suitable formulations for parenteral, subcutaneous, intradermal, intramuscular, oral or intraperitoneal administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers. Also, αGal$^{(+)}$ TAA proteins or peptides can be mixed with immune adjuvants well known in the art such as Freund's complete adjuvant, inorganic salts such as zinc chloride, calcium phosphate, aluminum hydroxide, aluminum phosphate, saponins, polymers, lipids or lipid-fractions (Lipid A, monophosphoryl lipid A), modified oligonucleotides, etc.

In addition to administration with conventional carriers, active ingredients may be administered by a variety of specialized delivery drug techniques which are known to those of skill in the art.

The invention will now be described with respect to the following examples; however, the scope of the present invention is not intended to be limited thereby. All citations to patents and journal articles are hereby expressly incorporated by reference.

EXAMPLES

Example 1

Production of Retroviral Vector Expressing αGT, pLNCKG

Figure 2:
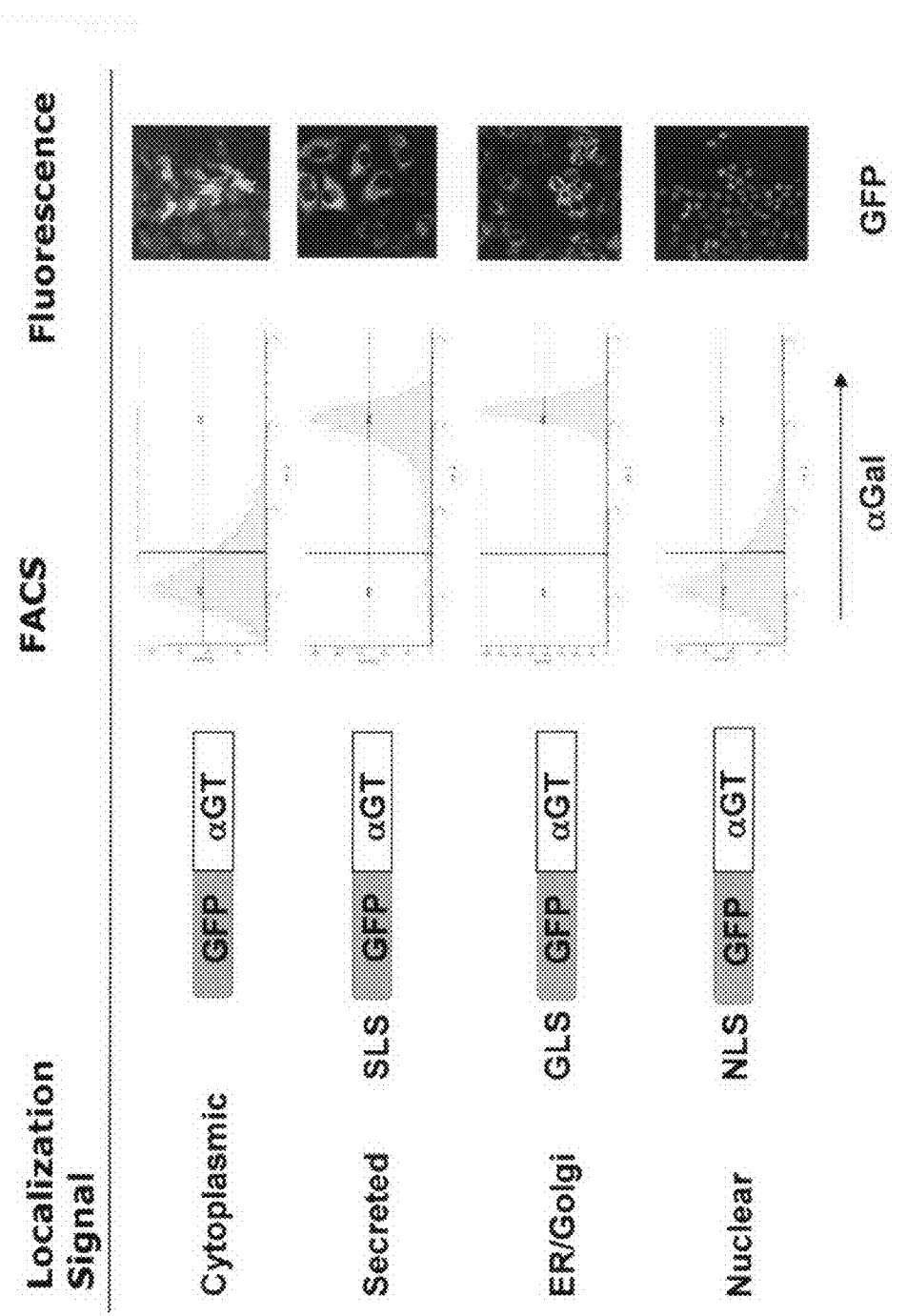
FIGS. 2A-D show the expression of a fusion protein consisting of: a subcellular localization signal, a protein that normally does not traffick through the ER/Golgi, in this case AcGFP was used as a model TAA to allow for easy subcellular localization, and the murine sequence of αGT with a deletion in its own subcellular ER/Golgi localization signal. The fusion proteins are cloned in MoMLV retroviral vectors and transduced into an αGT(−) human cell line A375. Analysis of αGT expression was carried by staining with IB4 lectin and detected by FACS. Analysis of AcGFP expression and its subcellular localization was determined by fluorescence microscopy. See Example 8.
Figure 2A:
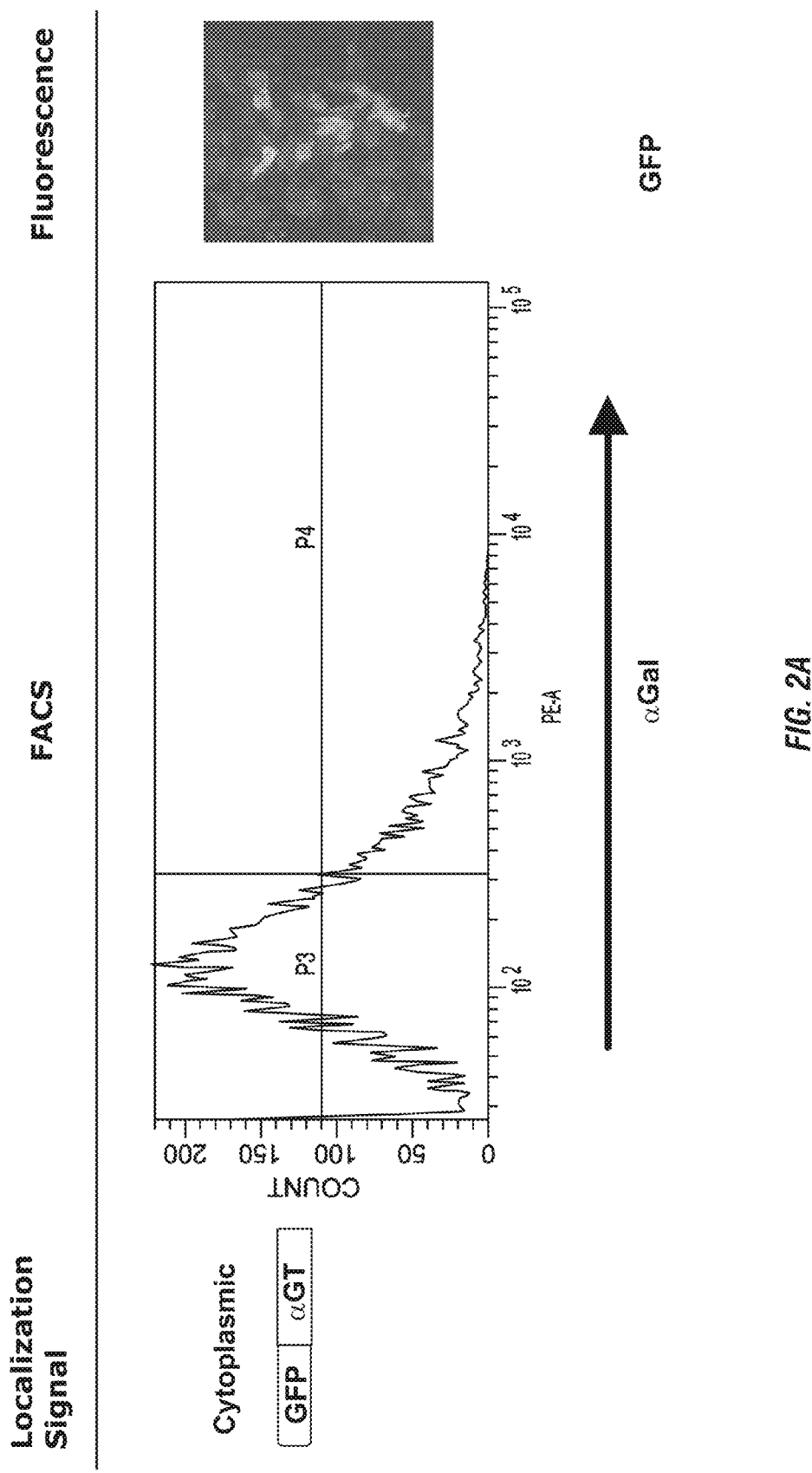
Figure 2B:
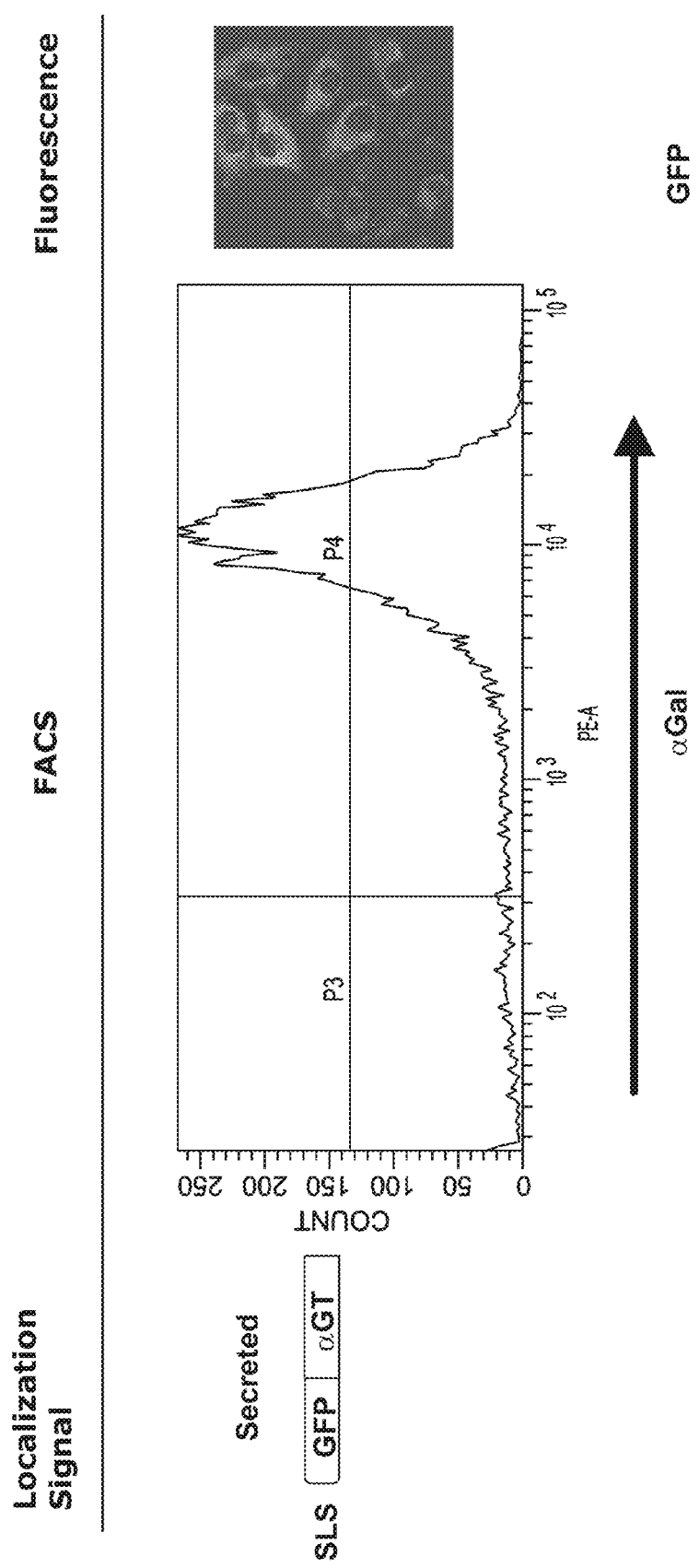
Figure 2C:
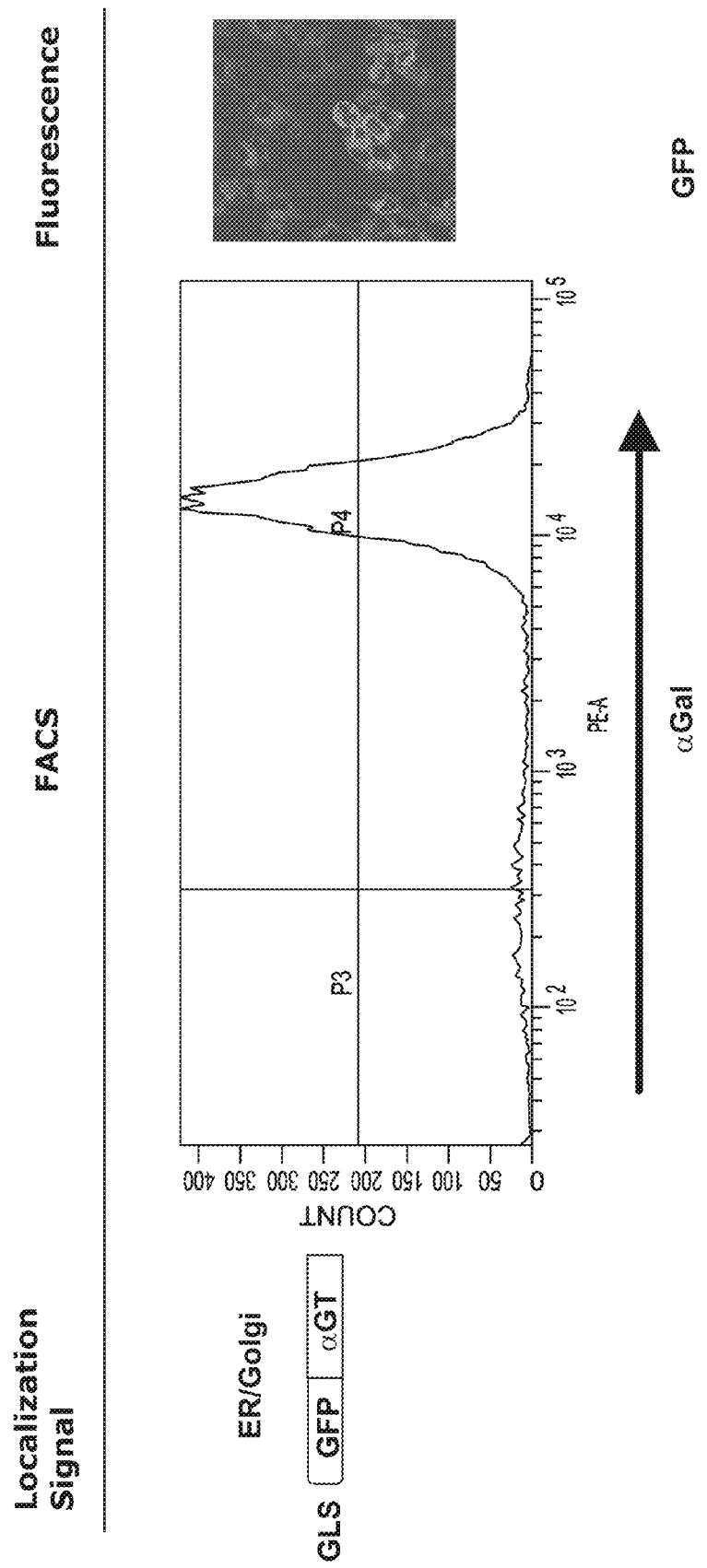
Figure 2D:
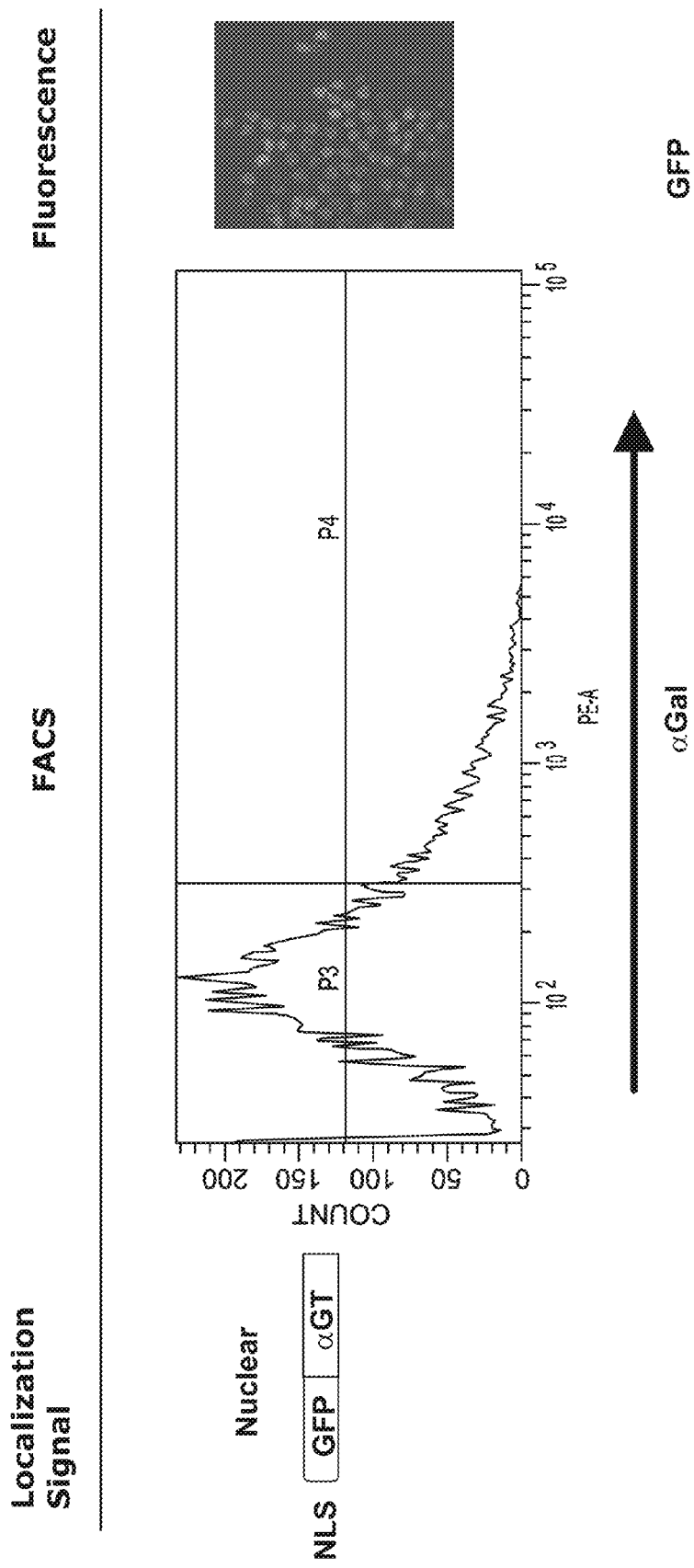

A 1,077 base pair (bp) fragment of murine αGT gene was PCR amplified by a forward primer, 5'-ACAAAAGCTTGA-CATGGATGTCAAGGGAAAAGTAAT-3', (SEQ ID NO: 1) which contains a Kozak sequence to enhance the translation of αGT, and a reverse primer, 5'-AATTATCGATTCAGA-CATTATTTCTAAC-3' (SEQ ID NO: 2), and then cloned into the ClaI and HindIII sites of pLNCX to produce pLNCKG retroviral vector (FIG. 2). This vector was transfected into the packaging cell line 293.AMIZ to generate the vector producer cell line 293.AMIZ/LNCKG (Young and Link 2000). Transfected cells were selected in presence of G418 and ZEO-CIN™ antibiotic for two weeks. Mixed population of selected cells was subcloned by limiting dilutions. Single cell-derived VPC were screened for their ability to effectively transduce human epithelial cancer cell lines established from different tissues. The clone which supernatant consistently yielded highest transduction efficiency and αGT expression on a panel of human epithelial cancer cell lines was identified and designated 293Z.CKG VPC. A master cell bank, working cell bank and production lot was generated for 293Z.CKG VPC was originated from one vial of the seed bank, expanded in flasks at 37° C.±1° C. in 5%±1% CO2. The culture medium was RPMI-1640 supplemented with 10% fetal bovine serum (FBS) and 2 mm L-glutamine. When the 293Z.CKG VPC reached sufficient density, the culture fluids (supernatant) are harvested, filtered, and pooled into a sterile container. The pool is thoroughly mixed and then aseptically filled into labeled, sterile plastic bottles. (Labels contain the product name, lot number and date of filling.) The fill bottles are frozen and stored at or below −60° C. Retrovirus-containing supernatants from 293Z.CKG VPC can be used to transduce αGal$^{(−)}$ cell lines of human, monkey, mouse or hamster (CHO) origin, in order to establish the αGal$^{(+)}$ cells used for expression of recombinant TAA.

Example 2

Production of Lentiviral Vector Expressing αGT, pHSPA

A PCR fragment containing the human phosphoglycerate kinase (PGK) promoter was amplified from pHPEA3 (Mautino and Morgan 2002) using primers 5'-CAGGAAT-TCACGGGGTTGGGG-3' (SEQ ID NO: 3) and 5'-TGACG-TACGATTAGCTT GATCATCCCCCTG-3' (SEQ ID NO: 4), digested with BspEI (completely filled in) and EcoRI and cloned in the EcoRI-EcoRV restriction sites of pLITMUS29 (New England Biolabs) to yield plasmid pLPGK. A PCR fragment of murine αGT gene was PCR amplified by a forward primer, 5'-ACAAAAGCTTGACATGGATGT-CAAGGGA AAAGTAAT-3' (SEQ ID NO: 5), which contains a Kozak sequence to enhance the translation of αGT, and a reverse primer, 5'-ATTGGTACCTCAGACA-TTATTTCTAAC-3' (SEQ ID NO: 6) and cloned in the HindIII-KpnI sites of pLPGK. The PGK-αGT expression cassette was excised from pLPGK with EcoRI-KpnI and cloned in the same restriction sites of pHCPE (Mautino and Morgan 2002). Infectious vector particles were produced by transient cotransfection into 3×10$^6$ 293T cells with 15 μg of vector pHSPA, 10 μg of HIV-1 helper packaging vector pCMVΔR82 and 5 μg of pLTR-G encoding VSV glycoprotein. Supernatant was collected 60 h after transfection and filtered through 0.45 μm mesh.

Example 3

Transduction of CHO Cells with LNCKG Retroviral Vector

CHO cells are extensively used to produce recombinant proteins and antibodies secreted into the culture medium (Werner et al. 1998). Despite being derived from a Chinese hamster which has a functional gene encoding αGT, CHO cells are αGal$^{(−)}$ (Sharma et al. 1996). To generate αGal$^{(+)}$ CHO cells, 2×10$^6$ cells are transduced with 2 mL of supernatant containing the LNCKG retrovirus with an infectious titer of 2×10$^6$ transducing units/mL. Cells are selected for resistance to Neomycin by a two-week selection in medium supplemented with G418 1 mg/mL. After this period of selection, cells are stained for expression of the αGal epitope with a chicken anti-αGal polyclonal antibody and sorted by fluorescence activated cell sorting.

Example 4

Transduction of B16 Melanoma Cells with pHSPA Retroviral Vector

B16 melanoma cells express the melanoma TAA gp75 and gp100 and be used as a source for purification of αGal$^{(+)}$ TAA (Naftzger et al. 1996). Despite being derived from wild type C57B16 mice which have a functional copy of αGT gene these cells are αGal$^{(-)}$ (Rossi et al. 2005a). To generate αGal$^{(+)}$ B16 cells, 2×10$^6$ cells were transduced with 10 mL of supernatant containing the pHSPA lentivirus with an infectious titer of 1×10$^6$ transducing units/mL. Transduction of cells was carried out at a multiplicity of infection of 5 transfection units per cell in the presence of 10 μg/mL polybrene. Cells were stained for expression of the αGal epitope with a chicken anti-αGal polyclonal antibody and sorted by fluorescence activated cell sorting [FIG. 1].

Example 5

Purification of αGal$^{(+)}$ gp75 from αGal$^{(+)}$ B16 Cells

The gp75 antigen can be purified from αGal$^{(+)}$ B16 cells using a protocol described previously (Naftzger et al. 1996; Vijayasaradhi and Houghton 1991). Briefly, cells are grown in DMEM 5% serum and harvested with EDTA 2 mM without trypsin. Cells are washed in PBS and 10$^{10}$ cells (~50 g cell pellet) are resuspended in 400 mL of homogenization buffer (20 mM Tris/HCl pH 7.5, 5 mM MgCl2; and protease inhibitor cocktail). Next, cells are homogenized and pelleted at 1000 g for 5 min, and the supernatant is recentrifuged at 10000 g for 20 min. The membrane pellet is resuspended in 40 mL 50 mM Tris/HCl, 3 M KCl and 5 mM EDTA, rehomogenized and pelleted at 100000 g for 90 min. The pellet is resuspended in 25 mL of 50 mM Tris/HCl and 0.5% Na-deoxycholate and centrifuged at 100000 g for 30 min. The buffer in the supernatant is exchanged by ultrafiltration dialysis to 2 mM CHAPS, 150 mM NaCl and 20 mM Tris/HCl and applied to a Mono Q columns equilibrated in the same buffer. The column is washed with 15 volumes of the equilibration buffer and bound proteins are eluted with a linear gradient of NaCl of 10 mM-1 M. Fractions are assayed by ELISA using the monoclonal Ab TA99. Positive fractions are pooled together, dialyzed against 10 mM Tris/HCl, 1 mM CaCl$_2$, 1 mM MnCl$_2$ and cocktail of protease inhibitors and applied to a Concanavalin A-Sepharose column (10 mL) and washed with 50 ml loading buffer. Bound proteins are eluted with 250 mM methylmannopyranoside and the fractions are assayed for the presence of gp75 by ELISA. Positive fractions are dialyzed against 10 mM Tris, 2 mM CHAPS and a cocktail of protease inhibitors and loaded onto an AFFI-GEL®-Hz (Bio-Rad) immunoaffinity column containing TA99 monoclonal antibody equilibrated in 10 mM Tris/HCl, 150 mM NaCl and 2 mM CHAPS. The cross-linking of TA99 to the AFFI-GEL®-matrix is performed according to the manufacturer's instructions. The column is washed sequentially with: 1) 50 mM HEPES pH 7.5, 150 mM NaCl; 2) 50 mM HEPES 1 M NaCl; 3) 50 mM HEPES, 150 mM NaCl, 2 mM CHAPS. Bound gp75 is eluted with a buffer of 150 mM Glycine, pH 3.5 and 2 mM CHAPS.

A similar process is employed to purify gp75 protein from αGal$^{(-)}$ B16 cells, to be used as negative controls in vaccination experiments.

Example 6

ELISA of αGal$^{(+)}$ gp75

The assay to test for the presence of gp75 in column fractions is performed by ELISA. Briefly, 200 μL of each sample is coated for 2 h on an ELISA plate. Wells are washed 6 times with TBS, and the wells are blocked for 1 h at room temperature with 300 μL 5% BSA in 150 mM NaCl. Plates are washed 6 times with 1×TBS, and TA99 mAb 100 μL (1:1000 dilution) is added to each well and incubated for 30 min. After washing, a secondary biotinylated rabbit anti-mouse IgG2A is added (100 uL, 1:1000 dilution) and incubated for 30 min. After 6× washing, 100 uL of streptavidin-horseradish (1:5000 dilution) peroxidase is added to each well and incubated for 30 min. After 6× washing, TMB—H$_2$O$_2$ is added to each well and the reaction is stopped after 15-30 min with 4N H$_2$SO$_4$.

Example 7

Detection of αGal Epitopes on αGal$^{(+)}$ gp75 by Western Blot

The presence of αGal epitopes on the affinity purified gp75 protein can be tested by Western blot. Purified protein is run under denaturing and reducing conditions on SDS-PAGE, transferred to membranes and tested for binding to either: 1) *Bandeiraea simplicifolia* IB4-HRP lectin (BS-lectin); 2) affinity-purified anti-αGal human antibodies; 3) anti-αGal chicken IgY, obtained by immunization of eggs with BSA-αGal (V Labs); or 4) the anti-αGal mouse monoclonal antibody M86 (IgM). The anti-αGal human IgG polyclonal antibody is purified from normal human sera, by affinity chromatography on columns Sepharose columns crosslinked to HSA-αGal (V Labs). Protein samples are separated on a 3.6% polyacrylamide stacking gel and a 12% resolving gel for 40 min at 200V. Proteins are then transferred to PVDF membranes by electroblotting and blocked overnight in 0.5% Tween-PBS (TPBS) with 1% bovine serum. The membranes are then incubated in either human anti-αGal, anti-αGal chicken IgY (1:1000) or 20 ug ml/horseradish peroxidase (HRP)-conjugated BS-lectin, both diluted in TPBS/1% bovine serum, for 1 h at room temperature followed by four washes for 15 min each in TPBS. The blots are incubated with HRP-conjugated secondary antibodies either against human IgG, chicken IgY or anti-mouse IgM antibody, diluted 1:1000, for 30 min at room temperature and washed as above. Membranes are then embedded in a solution of chemofluorescence substrate and then exposed to x-ray film.

Example 8

Expression of αGal$^{(+)}$ Recombinant Fusion Proteins in αGal$^{(-)}$ Mammalian Cells The following experiment was conducted to demonstrate that addition of secretory or Golgi amino acid sequence localization signals to a TAA that does not normally traffick through the Golgi would result in trafficking and expression of such TAA in the right subcellular compartment and with the proper glycosylation pattern (FIG. 2). Four retroviral vectors based on Moloney murine leukemia virus were constructed with expression cassettes encoding the following fusion proteins:

1] GFP-αGT
2] SLS-GFP-αGT
3] GLS-GFP-αGT
4] NLS-GFP-αGT where SLS is the secretory localization signal from placental alkaline phosphatase (amino acid sequence MDLLLLLLLGLRLQLSLGRIP SEQ ID NO: 12), GLS is the Golgi localization sequence of αGT (MDVKGKVILLM-LIVSTVVVVFWEYVNRIP SEQ ID NO: 13) and NLS is a control nuclear localization signal (amino acid sequence MDPKKKRKVRIADPKKKRKV SEQ ID NO: 14). In these constructs, the endogenous Golgi localization signal has been deleted from αGT. Also, GFP is used instead of a true TAA to monitor the localization of GFP protein by fluorescence microscopy. In this particular case, the antigen is directly fused to αGT to ensure co-expression of αGT and that of the antigen. These constructs were produced in A375.AMIZ retroviral packaging cell line, and the supernatant was used to transduce human A375 melanoma cells. Activity of αGT was monitored by staining cells with IB4 lectin from *G. simplicifolia* conjugated to fluorescein and analyzed by FACS. The results indicate that if no subcellular localization signal is added to the fusion protein, GFP and αGT are coexpressed in the cytoplasm and there is no αGT enzymatic activity as cells are αGal$^{(-)}$ by FACS. Addition of the SLS or the GLS to the N-terminus of GFP results in the proper ER/Golgi localization of the fusion protein, and αGT activity can be measured as the transduced A375 cells are αGal$^{(+)}$ by FACS. Addition of a control NLS results in nuclear distribution of the fusion protein and undetectable αGT activity as cells are αGal$^{(-)}$ by FACS. This example demonstrates that the proper SLS or GLS has to be added to the N-terminus of the putative TAA to be expressed in these cells in order to achieve proper cellular trafficking and expression of αGT to mediate the addition of αGal epitopes to the TAA of interest. Replacement of GFP by the TAA sequence of interest in Construct #2 would allow one to purify the αGal$^{(+)}$ TAA from the culture supernatant. Addition of a sequence affinity tag and protease cleavage site between the TAA and αGT would allow to recover the αGal $^{(+)}$ TAA free form the αGT portion.

Example 9

Expression, Purification and Synthesis of $\alpha Gal^{(+)}$ BORIS Protein Fragment Vaccine Among the different classes of TAA, cancer testis genes are excellent vaccine candidates as they are not normally expressed in any non-malignant tissue of adult females and are only expressed in the testis of adult males. As testes are an immunoprivileged tissue, cancer testis TAA is expected to be similar to non-self antigens and trigger a potent immune response. More than 80 cancer testis genes have been identified so far (Simpson et al. 2005). Cancer testis genes such as NY-ESO1, MAGE-A1 and BORIS are expressed in many cancers cell lines and primary tumors. BORIS encodes a DNA binding protein that shares a central 11-zinc finger domain with the epigenetic regulator of imprinting CTCF (Loukinov et al. 2002). CTCF has a ubiquitous expression profile which does not make it a good candidate for vaccination. CTCF and BORIS differ in their N-terminus and C-terminus amino acid sequence. Moreover, CTCF and BORIS have been shown to reciprocally bind to the promoter of cancer testis genes such as NY-ESO1 in pulmonary carcinomas and expression of BORIS is correlated with the expression of NY-ESO1 (Hong et al. 2005). BORIS expression has been documented in cell lines and primary tumors of diverse histology such as prostate, lung, colon, breast, ovary, stomach, liver, glia, colon and esophagus (Lobanenkov et al. 2005). This makes the N-terminus and C-terminus domain of BORIS modified by addition of αGal epitopes and excellent candidate for antitumor vaccination for diverse types of cancers. In fact, DNA vaccination with a plasmid encoding BORIS lacking the DNA binding domain, in the presence of adjuvant and boosted with adenoviral vectors encoding the same protein domains shows some antitumor effect in Balb/C mice inoculated with 4T1 breast tumor cells, which express BORIS mRNA (Loukinov et al. 2006). However, none of the animals survived more than 60 days which indicates that the vaccination protocol still needs to be further optimized. Modification of the BORISΔ(ZF) by in vitro addition of αGal epitopes is expected to yield a highly immunogenic vaccine that triggers both humoral and cellular antitumor immune response.

The following procedure describes the cloning of the N-terminal portion of human and murine BORIS genes into bacterial expression vectors. Only the portion encoding the N-terminal fragment of BORIS genes that do not encompass the 11-zinc finger domains that show high homology with CTCF is cloned into pTWIN1 expression vector (New England Biolabs).

The human N-terminal fragment of BORIS is obtained by RT-PCR from human A375 cells using the primers hBORIS-F1 5'-GGTGGTCCATGGGTCGGGCAATGGCA GCCACTGAGATCCTCTGTCC-3' (SEQ ID NO:7) and hBORIS-R1 5'-GGTGGTGGA TCCTTAgtggtgGTGGTGGTGGTGGAAGG TTCCTTTTGCTCCCTT T-3' (SEQ ID NO:8). These primers amplify amino acids 1-258 of the human BORIS protein, while adding a C-terminal $(His)_6$ tag to aid protein purification. The PCR fragment is digested with NcoI and BamHI and ligated into pTWIN1 vector (New England Biolabs) digested with NcoI and BamHI to yield plasmid pThBORIS-Nt.

The murine N-terminal fragment of BORIS is obtained by RT-PCR from 4T1 cells using primers mBORIS-F1 5'-GGTGGTCCATGGGTCGGGCAATGGCTGC-CGCTGAG GTCCCTGTCCCTT-3' (SEQ ID NO: 9) and mBORIS-R1 5'-CTTAGTGGTGGTGGT GGTGGTGCT-GAAAGCTCTGAGGCTTTCCCAA-3' (SEQ ID NO: 10). These primers amplify amino acids 1-258 of the murine BORIS protein, while adding a C-terminal $(His)_6$ tag to aid protein purification. The PCR fragment is digested with NcoI and ligated into pTWIN1 vector digested with NcoI and BamHI (completely filled-in with T4 DNA Polymerase), to yield plasmid pTmBORIS-Nt. Cloning of these fragments in the pTWIN1 vector creates an expression cassette which consists in IPTG-inducible T7 RNA polymerase dependent promoter which drives the expression of RNA encoding a fusion protein consisting of three domains: 1) a chitin binding domain, 2) a self cleaving Ssp Intein and 3) the $BORIS_{1-258}$-$His_6$ domains. The vectors pThBORIS-Nt and pTmBORIS-Nt are transformed into *E. coli* BL21 pLysS. An overnight culture in LB-Glucose is diluted 1:10 and grown at 37 C for 4-6 h until $OD_{600}$ is ~0.6. Protein expression is induced with IPTG 250 μM for 1-3 h. Cells are washed in PBS and lysed by sonication in 20 mM Phosphate buffer pH 7, 200 mM NaCl, 1 mM EDTA, 0.1% TritonX100 and 1 mM PMSF. Cell lysate is centrifuged at 18000 g for 30 min and the supernatant is cleared by filtration through 0.45 μM pore. The cleared lysate is loaded onto a chitin column activated according to the manufacturer's instructions. The column is washed with 10 volumes of 20 mM phosphate buffer pH 8.5, 600 mM NaCl, 1 mM EDTA, 0.1% Triton X100 and 1 mM PMSF. Cleavage of the BORIS from the fusion protein is induced by change in pH. Cleavage buffer (20 mM Phosphate buffer pH 6.0, 600 mM NaCl, 1 mM EDTA) is added to the column and incubated 16 h at room temperature. The cleaved BORIS protein is eluted by running 3 volumes of cleavage buffer through the column. Protein is concentrated and dialyzed into 50 mM Phosphate buffer pH 7 and loaded into a $Ni^{+2}$-resin column following the manufacturer's instructions. The column is washed with 50 mM imidazole and eluted in a linear gradient of 100-500 mM imidazole. Protein is concentrated and dialyzed by ultrafiltration into 50 mM Phosphate buffer pH 7.0. Yield and purity of the BORIS protein is performed by ELISA and Western blot using an anti-$HiS_6$ monoclonal antibody following standard procedures.

To obtain the $\alpha Gal^{(+)}$ N-terminal human and murine BORIS protein, a αGal epitope can be obtained from a commercial source (Dextra Labs, Reading, UK), or synthesized according to described Examples 22 to 32 or published protocols (Hanessian, 2001, Tetrahedron). This αGal epitope is crosslinked to the purified protein by adding the αGal-NHS compound dissolved in DMF or DMSO at 10-20 fold molar excess, incubating for 2 h at room temperature and dialyzing the $\alpha Gal^{(+)}$ protein in PBS.

Example 10

Synthesis of $\alpha Gal^{(+)}$ BORIS-Derived Peptides

An alternative embodiment for the generation of $\alpha Gal^{(+)}$ BORIS vaccines is to synthesize $\alpha Gal^{(+)}$ peptides derived from the $NH_2$— or COOH— terminus of murine or human BORIS, excluding the amino acid sequences that are common to CTCF, followed by chemical addition of αGal epitopes. αGal epitopes can be obtained from a commercial source (Dextra Labs, Reading, UK), or synthesized according to described protocols (Hanessian et al. 2001b) or as described in Examples 22 to 32 and FIGS. 3-6. The αGal-NHS epitope is crosslinked to primary amines in the peptides such as Lysines or the free terminal $NH_2$— group. The αGal-Mal epitope is crosslinked to free $SH_2$— groups such as the ones present in Cysteine or Homocysteine. Briefly, peptides are solubilized in DMSO at 10 mM and diluted to 100 μM in 50 mM phosphate buffer pH 7. The αGal-NHS or αGal-Mal compounds are dissolved in DMF or DMSO at 10 mM. 50-100 μL of αGal-NHS or αGal-Mal is added to the peptide solution (10-20 fold molar excess) and the reaction is incubated at room temperature for 2 hours. Excess of unreacted αGal-NHS or αGal-Mal is eliminated by dialysis or ultrafiltration.

The peptides used for vaccination have the structure αGal-Z-$X_{1-20}$-Peptide-$X_{1-20}$-Z-αGal, where Z can be a Cysteine, Homocysteine or Lysine, $X_{1-20}$ refers to any sequence of 1-20 amino acids, and Peptide refers to the sequences of amino acids for the human or murine BORIS indicated in Table 1. This table suggests different peptides that will be better suited to bind to different alleles of MHC or HLA molecules:

TABLE 1

BORIS derived peptides to elicit antitumor response

| HLA Type | Peptide | SEQ ID NO |
|---|---|---|
| Human | | |
| HLA-A201 | VLSEQFTKI | 20 |
| | VLTVSNSN | 21 |
| | ILTLQTVHFT | 22 |
| | SVLEEEVELV | 23 |
| | SVLEEEVEL | 24 |
| | KLAVSLAET | 25 |
| | LLAERTKEQL | 26 |
| HLA-A1 | LAETAGLIK | 27 |
| HLA-A03 | SVLSEQFTK | 28 |
| | SLAETAGLIK | 29 |
| | ILKEATKGQK | 30 |
| | EAANGDEAAA | 31 |
| | LKEATKGQK | 32 |
| | VLAPSEESEK | 33 |
| HLA-A24 | LYSPQEMEVL | 34 |
| HLA-A26 | EQFTKIKEL | 35 |
| | EVDEGVTCE | 36 |
| | EESEKYILTL | 37 |
| HLA-A68.1 | GVCREKDHR | 38 |
| | SVLSEQFTK | 39 |
| | NVMVASEDSK | 40 |
| | FVETMSGDER | 41 |
| HLA-B08 | AERTKEQL | 42 |
| | TRKRKQTI | 43 |
| HLA-B18 | QEMEVLQF | 44 |
| HLA-B2705 | ERTKEQLFF | 45 |
| HLA-B4402 | EESEKYILTL | 46 |
| HLA-DRB1 | VQVVVQQPGPGLLWL | 47 |
| | LLSIQQQEGVQVVVQ | 48 |
| | LLWLEEGPRQSLQQC | 49 |
| | VETMSGDERSDEIVL | 50 |
| | GEMFPVACRETTARV | 51 |
| | SEQFTKIKELELMPE | 52 |
| | KLAVSLAETAGLIKL | 53 |
| | EMEVLQFHALEENVM | 54 |

| MHC | Peptide | SEQ ID NO |
|---|---|---|
| Murine | | |
| H2-$K^d$ | LYPPEELQRI | 55 |
| | SFQDPEHETL | 56 |
| | HFHLLRENVL | 57 |
| | YFTQIKEQKL | 58 |
| | LWLDPEPQL | 59 |
| | HFHLLRENV | 60 |
| | APVESDRRI | 61 |
| | LQLPSVLWL | 62 |
| | VTVSIPEEL | 63 |

Example 11

Synthesis of $\alpha Gal^{(+)}$ bcr-abl Derived Peptides for Vaccination Against Chronic Myelogenous Leukemia Chronic myelogenous leukemia is generated by a translocation t(9;22) that results in the chimeric bcr-abl gene encoding a 210 kDa fusion protein. There are two possible fusions that result in a functional in-frame Bcr-Abl fusion protein, characterized by the fusion of the second or third exon of Bcr and the second exon of Abl. These two fusions are designated b3a2 and b2a2. The junction of these two protein domains generates a new amino acid sequence against which the patient is not supposed to have been immunologically tolerized. Therefore, this junction sequence constitutes a novel TAA and a good candidate for vaccination approaches to eliminate residual disease in patients that respond to Imatinib or to treat patients that are resistant to Imatinib (Gleevec). Several studies have identified different peptides derived from the Bcr-Abl fusion that bind to different alleles of class I and II HLAs (Bocchia et al. 1996; Bocchia et al. 1995). Clinical trials have been conducted by vaccination with synthetic peptide vaccines (Cathcart et al. 2004; Pinilla-Ibarz et al. 2000). bcr-abl-derived peptide vaccine can be safely administered to patients with CML and can elicit a reliable specific CD4 immune response. However, no cytotoxic T lymphocytes have been identified in these trials. A way to circumvent the poor immunogenicity of these peptides in order to elicit a more potent CD8+ immune response would be by the methods of the present invention, consisting in the chemical modification of such peptides with αGal epitopes. The peptides described in the following Table could be used for vaccination against CML:

| HLAType | Peptide | (SEQ ID NO:) |
|---|---|---|
| HLA-A201 | SSKALQRPVC-αGal | 64 |
|  | αGal-CSSKALQRPVGSS KALQRPVGSSKALQRPV C-αGal | 65 |
| HLA-A3 | KQSSKALQRC-αGal | 66 |
|  | αGal-CKQSSKALQRGSK QSSKALQRGSKQSSKALQ RC-αGal | 67 |
| HLA-A11 | ATGFKQSSKC-αGal | 68 |
|  | αGal-ATGFKQSSKCG-SATGF KQSSKCGSATGFKQSSK C-αGal | 69 |
| HLA-A3/11 | HSATGFKQSSK-αGal | 70 |
|  | αGal-CHSATGFKQSSK GSHSATGFKQSSKGSHS ATGFKQSSKC-αGal | 71 |
| HLA-B8 | GFKQSSKALC-αGal | 72 |
|  | αGal-CGFKQSSKALCG SCGFKQSSKALCGSCGF KQSSKALC-αGal | 73 |
| Class II | αGal-CIVHSATGFKQS SKALQRPVASDFEP C-αGal | 74 |

Example 12

Synthesis of αGal(+) gp75-Derived Peptides

The following peptides, chemically synthesized by solid phase synthesis, can be used to test the immunogenicity of αGal(+) peptides derived from the mouse TAA gp75 (TRP-1) in an αGT knockout mouse.

1] TWHRYHLL (SEQ ID NO: 75) is the natural sequence corresponding to amino acids 222-229 of murine gp75
2] TAYRYHLL (SEQ ID NO: 76) is a heteroclitic variant of peptide #1 that has better binding affinity to MHC-I H2-K$^b$ (Dyall et al. 1998)
3] KTAYRYHLL (SEQ ID NO: 77) is peptide #2 with an N-terminal Lysine
4] KTAYRYHLLGSTAYRYHLL (SEQ ID NO:80) is derived from peptide #2 with an N-terminal tag containing an N-terminal Lysine
5] KTAYRYHLLGSTAYRYHLLGSTAYRYHLLK (SEQ ID NO: 78) is derived from peptide #2 with an N-ter and C-ter tag consisting of the sequence of peptide #2 flanked by N-ter and C-ter Lysines that serve as anchoring points for chemically synthesized αGal epitopes with NHS linkers.

If the N-ter of each peptide is not blocked by N-formylation, then the N-terminal Lys can be omitted from the sequence of the peptides.

Chemically activated αGal epitopes (of generic formula αGal-L$_1$-NHS, wherein L$_1$ is a linker) can be obtained from a commercial source (Dextra Labs, Reading, UK), or synthesized according to described protocols (Hanessian et al. 2001b) or as described in Examples 22 to 32 and FIGS. 3-6.

This αGal-L$_1$-NHS epitope is crosslinked to peptides #3, #4 and #5 using the following method. Briefly, peptides are solubilized in DMSO at 10 mM and diluted to 100 μM in 50 mM phosphate buffer pH 7. The αGal-NHS compound is dissolved in DMF or DMSO at 10 mM. 50-100 μL of αGal-NHS is added to the peptide solution (10-20 fold molar excess) and the reaction is incubated at room temperature for 2 hours. Excess of unreacted αGal-NHS is eliminated by dialysis.

Example 13

Induction of Anti-αGal Antibodies in αGT KO Mice by Immunization with Rabbit Red Blood Cells Females and males 8 to 14 weeks old αGT knockout mice were used in this study. Mice were initially of mixed haplotype (H-2 b/d) and by breeding and selection the current colony of αGT KO mice was obtained consisting in F4 inbreeding generation of H-2 b/b haplotype. These animals produce low titers of natural antibodies against αGal epitopes. To increase the titer of anti-αGal Ab mice are immunized intraperitoneally (i.p.) with 1×10$^8$ rabbit red blood cells twice, two weeks apart. The titers of anti-αGal Ab are checked one week after the last RRBC injection to corroborate that all mice in the study have high titers of anti-αGal Ab. In this manner, this model mimics the high titer of natural anti-αGal antibodies present in humans. All mice used in this study have high anti-αGal Ab titers greater than 1:500 dilution, measured by ELISA.

Example 14

Immunization with αGal(+) gp75 Purified from αGal(+) B16 Cells

The following animal experiment is performed to induce antitumor immunity against B16 melanoma cells with αGal(+) gp75 protein purified from αGal(+) B16 melanoma cells. αGT KO mice (of C57B1/6 genetic background, H-2 Kb/b) are immunized with rabbit red blood cells (RRBC) as described previously to induce the presence of anti-αGal antibodies. Additionally, wild type C57B16 mice, which do not develop anti-αGal antibodies, are used as control groups. Each animal is immunized with 2 to 3 doses of 1 to 100 μg of purified αGal(+) or αGal(−) gp75, resuspended in saline solution, without adjuvant. Examples of possible treatment and control groups and doses are:

| Group | Strain | Vaccine | Dose |
|---|---|---|---|
| 1 | αGT KO | saline | — |
| 2 | αGT KO | αGal$^{(-)}$ gp75 | 1 ug |
| 3 | αGT KO | αGal$^{(-)}$ gp75 | 10 ug |
| 4 | αGT KO | αGal$^{(-)}$ gp75 | 100 ug |
| 5 | αGT KO | αGal$^{(+)}$ gp75 | 1 ug |
| 6 | αGT KO | αGal$^{(+)}$ gp75 | 10 ug |
| 7 | αGT KO | αGal$^{(+)}$ gp75 | 100 ug |
| 8 | C57Bl6 | αGal$^{(+)}$ gp75 | 100 ug |
| 9 | C57Bl6 | αGal$^{(-)}$ gp75 | 100 ug |

The vaccines are administered by subcutaneous injection, and each dose is administered 7-10 days apart. Immunologic tests are conducted one week after the last immunization as described below.

Example 15

Immunization with αGal$^{(+)}$ gp75-Derived Peptides

The following immunizations are performed to induce antitumor immunity against B16 melanoma cells with αGal$^{(+)}$ gp75-derived peptides. αGT KO mice (of C57B1/6 genetic background, H-2 K$^{b/b}$) are immunized with rabbit red blood cells (RRBC) as described previously to induce the presence of natural anti-αGal antibodies. Additionally, wild type C57Bl6 mice, which do not develop anti-αGal antibodies are used as control groups. Each animal is immunized with 2 to 3 doses of 1 to 10 μg of purified αGal$^{(+)}$ or αGal$^{(-)}$ gp75-derived peptide, resuspended in saline solution, with or without adjuvant. Examples of possible treatment and control groups and doses are:

| G # | Strain | Peptide Vaccine (SEQ ID NO:) | Dose |
|---|---|---|---|
| 1 | αGT KO | none | — |
| 2 | αGT KO | αGal$^{(-)}$-KTAYRYHLL(79) | 1 μg |
| 3 | αGT KO | αGal$^{(-)}$-KTAYRYHLL(79) | 10 μg |
| 4 | αGT KO | αGal$^{(+)}$-KTAYRYHLL(79) | 1 μg |
| 5 | αGT KO | αGal$^{(+)}$-KTAYRYHLL(79) | 10 μg |
| 6 | αGT KO | αGal$^{(-)}$-KTAYRYHLLGSTAYRYHLL(80) | 1 μg |
| 7 | αGT KO | αGal$^{(-)}$-KTAYRYHLLGSTAYRYHLL(80) | 10 μg |
| 8 | αGT KO | αGal$^{(+)}$ KTAYRYHLLGSTAYRYHLL(80) | 1 μg |
| 9 | αGT KO | αGal$^{(+)}$-KTAYRYHLLGSTAYRYHLL(80) | 10 μg |
| 10 | αGT KO | αGal$^{(-)}$-KTAYRYHLLGSTAYRYHLLK(81) | 1 μg |
| 11 | αGT KO | αGal$^{(-)}$-KTAYRYHLLGSTAYRYHLLK(81) | 10 μg |
| 12 | αGT KO | αGal$^{(+)}$-KTAYRYHLLGSTAYRYHLLK(81) | 1 μg |
| 13 | αGT KO | αGal$^{(+)}$-KTAYRYHLLGSTAYRYHLLK(81) | 10 μg |
| 14 | C57Bl6 | αGal$^{(-)}$-KTAYRYHLL(79) | 10 μg |
| 15 | C57Bl6 | αGal$^{(+)}$-KTAYRYHLL(79) | 10 μg |
| 16 | C57Bl6 | αGal$^{(-)}$-KTAYRYHLLGSTAYRYHLL(80) | 10 μg |
| 17 | C57Bl6 | αGal$^{(+)}$-KTAYRYHLLGSTAYRYHLL(80) | 10 μg |
| 18 | C57Bl6 | αGal$^{(-)}$-KTAYRYHLLGSTAYRYHLLK(81) | 10 μg |
| 19 | C57Bl6 | αGal$^{(+)}$-KTAYRYHLLGSTAYRYHLLK(81) | 10 μg |

The vaccines are administered by subcutaneous or intradermal injection, and each dose is administered 7-10 days apart. Immunologic tests are conducted one week after the last immunization as described below.

It has been previously described that in the presence of adjuvant, the heteroclitic peptide TAYRYHL (SEQ ID NO:76) induces protective immunity against B16 melanoma in C57B1/6 mice (H-2K$^b$), as this tumor cell line expresses gp75 and the peptide TWHRYHLL (SEQ ID NO:75) in the context of their MHC-I molecules (Dyall et al. 1998). However, in the absence of adjuvant this peptide is not immunogenic. The presence of αGal epitopes elicits the formation of immunocomplexes, which are able to elicit an immune response even in the absence of adjuvant. Analysis of the immune response parameters obtained after the immunization treatments described above will give information regarding the effect of the αGal epitope on the immunogenicity of the peptide, the effects of the αGal epitope on the potency or dose necessary to achieve certain levels of immune response and the effect of the presence of anti-αGal antibodies on the final immune response. Additionally, it will evaluate the effects of having none, one or two αGal epitopes per molecule and the effects of having the αGal epitope immediately linked to the immunizing peptide or separated from the αGal epitope by a tag of 8-11 amino acids.

Example 16

Evaluation of Immune Response in Mice After Vaccination with αGal$^{(+)}$ gp75 or αGal$^{(+)}$ gp75-Derived Peptides It is expected that after immunization with gp75 protein or peptides T cells will show a higher response in the ability to recognize αGal$^{(-)}$ B16 cells that express gp75 when the immunizing antigen is αGal$^{(+)}$ than when the immunizing antigen is αGal$^{(-)}$. To test this hypothesis, splenocytes from mice vaccinated with αGal$^{(+)}$ or αGal$^{(-)}$ gp75 or peptide vaccines are harvested and cultured for 6 h in presence or absence of stimulation. The control for maximum stimulation is the ionophore PMA/Ca$^{++}$. $10^6$ splenocytes are cultured with $10^5$ irradiated B16 cells to measure specific recognition or with CA320M intestinal sarcoma, a non-specific αGal$^{(-)}$ cell line with identical H-2$^{b/b}$ haplotype. This cell line was obtained by intraperitoneal injection of 2 mg 9,10-dimethyl-1,2-benz-anthracene (DMBA) and 1 mg 3-methylcholan-threne (3-MC) dissolved in 250 μl of olive oil at two week intervals into αGT KO mice. Alternatively, as control for specificity of immunity mediated against this peptide, the B16-derived radiation induced gp75$^{(-)}$ cell B78H.1 can be used as a negative control (Mintz and Silvers 1967). After incubation cells are harvested and stained for intracellular IFNγ and/or TNFα. Detection is performed by FACS gating for lymphocytes in the forward scatter plot. The percentage of lymphocytes activated by PMA/Ca++ ionophore is considered the maximum activation detectable in this experiment. Resting (unstimulated) T cells and T cells stimulated with CA320M or B78H.1 are expected to have undetectable intracellular IFNγ or TNF-α, indicating that no T cells precursors that are able to recognize antigens in CA320M or other antigens on B16 that are not derived from gp75 are induced after vaccination. On the contrary, vaccination with αGal$^{(+)}$ gp75 or αGal$^{(+)}$ gp75-derived peptides is expected to induce T cell precursors that specifically recognize αGal$^{(-)}$ B16 in vitro. Additionally, the number of precursors in spleens from mice vaccinated with αGal$^{(+)}$ TAA is expected to be superior than the number of precursors observed in spleens of mice vaccinated with αGal$^{(-)}$ TAA. This result would suggest that these T cells induced after vaccination with αGal$^{(+)}$ TAA maybe responsible for tumor prevention in mice challenged with B16 tumor cells.

In a different set of experiments, cell-surface activation markers can be used to measure specific T cell recognition of the αGal$^{(-)}$ B16 melanoma cell line induced by vaccination. It is well described that upon engagement of the T cell receptor (TCR), T cells up-regulate several cell surface molecules that indicate an activated state of the lymphocyte. One of those molecules is the L-2 receptor α chain or CD25. Upon TCR engagement, CD25 is up-regulated and can be detected by FACS at 1 day after activation. Similarly, CD69 (or very early activation antigen (VEA)) is up-regulated upon T cell activation. CD69 functions as a signal-transmitting receptor in different cells, it is involved in early events of lymphocyte activation and contributes to T cell activation by inducing synthesis of different cytokines, and their receptors. Both activation markers (CD25 and CD69) are expressed at very low level in resting T cells. To demonstrate that vaccination with αGal$^{(+)}$ TAA proteins or peptides induced T cell precursors able to recognize specifically B16, the up-regulation of activation markers can be used as parameters to measure recognition and activation. Cells are harvested from the spleens of mice vaccinated with αGal$^{(-)}$ or αGal$^{(+)}$ gp75 or gp75-derived peptides. These cells are cultured without stimulation or stimulated with a negative control cell line (CA320M) or with αGal$^{(-)}$ B16. After 24 hours of culture, cell are harvested and stained to detect CD25 or CD69 by FACS. It is expected that resting T cells (no stimulation) and cells stimulated with the syngeneic non-melanoma cell line CA320M expressed very low levels of activation markers. On the other hand, increased numbers of activated (CD25$^{(+)}$ and CD69$^{(+)}$) lymphocytes from mice vaccinated with αGal$^{(+)}$ TAA is expected when T cells are cultured with αGal$^{(-)}$ B16.

Example 17

Prevention of Subcutaneous Melanoma Tumor Growth by Vaccination with αGal$^{(+)}$ TAA or αGal$^{(+)}$ TAA-Derived Peptides In order to test whether vaccination with αGal$^{(+)}$ TAA or TAA-derived peptides induces protective antitumor immunity, different αGal$^{(+)}$ or αGal$^{(-)}$ peptides derived from gp75 are used to vaccinate αGT KO mice that have been primed to have anti-αGal antibodies by vaccination with RRBC. Peptides #1 to #5 are synthesized in their αGal$^{(+)}$ or αGal$^{(-)}$ forms and different groups of 15 αGT KO mice each receive three weekly doses of 5 µg of a peptide vaccine, injected subcutaneously without adjuvant. One week after the last dose of vaccination mice are challenged by subcutaneous (s.c.) injection of 10$^5$ B16 cells. Tumor growth is monitored 3 times a week with a Vernier caliper by measuring three perpendicular diameters, which are multiplied to obtain the minimum cube that will contain the tumor. When tumors reach a volume higher than 1000 mm$^3$, animals are sacrificed. Differences in the potency of each vaccine is evaluated by statistical comparisons of the survival curves (Kaplan-Meier) by the Logrank test, and also by statistical evaluation of differences in the parameters that describe tumor growth kinetics such as time of tumor onset (defined as the time it takes for a tumor to achieve an irreversible volume higher than a predetermined threshold (such as 65 mm 3) and tumor growth rate (assuming exponential growth kinetics).

Example 18

Prevention of Metastatic Melanoma Tumor Growth by Vaccination with αGal$^{(+)}$ TAA or αGal$^{(+)}$ TAA-Derived Peptides In order to test whether vaccination with αGal$^{(+)}$ TAA or TAA-derived peptides induces protective antitumor immunity that will restrain the growth of metastatic tumor nodules, different αGal$^{(+)}$ or a Gal$^{(-)}$-peptides derived from gp75 are used to vaccinate αGT KO mice that have been primed to have anti-αGal antibodies by vaccination with RRBC. Peptides #1 to #5 were synthesized in their αGal$^{(+)}$ or αGal$^{(-)}$ forms and different groups of 15 αGT KO mice each receive three weekly doses of 5 µg of a peptide vaccine, injected subcutaneously without adjuvant. One week after the last dose of vaccination mice are challenged by i.v. injection (in the tail vein) of 5×10$^4$ B16 cells in 0.1 mL of saline solution. Metastatic tumor burden is measured 3-4 weeks after tumor challenge by sacrificing the animals and measuring lung weight, whole weight of metastatic tumor nodules outside the lung (intestine, liver, lymph nodes), and by measuring the ratio of melanin/total protein in homogenates of tissue containing tumor nodules. Melanin is measured by homogenizing tissue in NaOH 1N (5 g of unfixed tissue per 5 mL of NaOH 1N), in a grinder followed by sonication. The homogenate is centrifuged at 1000 g for 10 min and the supernatant is filtered through 0.45 µm filters. Pure melanin (Sigma) is used to prepare a standard curve, and absorbance of the filtered supernatant is determined at 405 nm. Total protein is also determined in the supernatant by a regular BCA assay. The ratio of melanin to total protein is a measure of the tumor burden within the tissue bearing metastatic nodules.

Example 19

Treatment of Pre-Established Metastatic Melanoma Tumors by Vaccination with αGal$^{(+)}$ TAA or αGal$^{(+)}$ TAA-Derived Peptides In order to test whether vaccination with αGal$^{(+)}$ TAA or TAA-derived peptides is potent and fast enough to induce antitumor immunity able to treat 4-5 day old pre-established B16 tumors, different αGal$^{(+)}$ or αGal$^{(-)}$ peptides derived from gp75 are used for vaccination of αGT KO mice that have been primed to have anti-αGal antibodies by vaccination with RRBC. One week after the last RRBC immunization, αGT KO mice are injected subcutaneously with 10$^5$ B16 live cells. Four to five days after tumor challenge mice receive three weekly doses of vaccination with either peptide #1 to #5 in their αGal$^{(+)}$ or αGal$^{(-)}$ forms. Tumor growth is monitored 3 times a week with a Vernier caliper by measuring three perpendicular diameters, which are multiplied to obtain the minimum cube that will contain the tumor. When tumors reach a volume higher than 1000 mm³, animals are sacrificed. Differences in the potency of each vaccine is evaluated by statistical comparisons of the survival curves (Kaplan-Meier) by the Logrank test, and also by statistical evaluation of differences in the parameters that describe tumor growth kinetics such as time of tumor onset (defined as the time it takes for a tumor to achieve an irreversible volume) and tumor growth rate (assuming exponential growth kinetics).

Example 20

Treatment of Pre-Established Melanoma Tumors by Adoptive T Cell Transfer from Mice Vaccinated with αGal$^{(+)}$ TAA or αGal$^{(+)}$ TAA-Derived Peptides The in vitro experiments shown above indicate that more quantity and quality of melanoma specific T cells are induced in mice vaccinated with αGal$^{(+)}$ TAA than in mice receiving αGal$^{(-)}$ TAA vaccination. These melanoma specific T cells are expected to be increased in numbers (more T cells found in spleens) and to produce more TNFα. Also, more splenocytes are expected to be activated when co-cultured with B16 (up-regulation of CD25 and CD69). It is expected that mice bearing both subcutaneous and lung pulmonary metastases receiving αGal$^{(+)}$ TAA vaccines show prolonged survival and increased clearance of the lung tumors than mice receiving αGal$^{(-)}$ TAA vaccines. These two groups of data would indicate that T cells induced by αGal$^{(+)}$ TAA vaccination are responsible for the treatment of pre-established melanoma tumors. However, it is not obvious that this is the case since it has been shown that large amount of melanoma-specific T cells are insufficient to treat pre-established subcutaneous melanoma tumors, since they are in a tolerant state (Overwijk et al. 2003). We hypothesized that vaccination with αGal$^{(+)}$ TAA would induced a strong T cell mediated immunity that can be rapidly activated upon recall to mediate tumor clearance in mice bearing pre-established disease. To demonstrate this hypothesis adoptive cell transfer experiments have to be conducted. Donor mice are vaccinated with three doses of αGal$^{(+)}$ or αGal$^{(-)}$ TAA. Recipient mice are injected i.v with 10⁵ live αGal$^{(-)}$ B16 to establish the lung melanoma metastases and randomized. Four days after i.v injection of non-irradiated B16, mice receive, or not T cells from donors vaccinated with αGal$^{(+)}$ or αGal$^{(-)}$ TAAs. Four weeks later, the lung melanoma metastasis burden is measured by enumerating lung tumors, by weighting lungs obtained in block and by quantification of melanin/protein ratios in homogenates of lung tissue. Melanin is measured by $A_{405}$ nm. A similar experiment was performed previously using irradiated αGal$^{(+)}$ or αGal$^{(-)}$ B16 whole cell vaccines and enhanced antitumor response was observed by vaccination with αGal$^{(+)}$ whole cell vaccines (Rossi et al. 2005a). Similarly, the same outcome is expected by vaccination with αGal$^{(+)}$ TAA protein or peptides.

Example 21

Antitumor Vaccination with αGal$^{(+)}$ BORIS-Derived Peptides

In order to test the effect of immunization of mice with αGal$^{(+)}$ BORIS-derived peptides the following αGal$^{(+)}$ peptide is synthesized:

KLYPPEELQRIGSLYPPEELQRIGSLYPPEELQRIK (SEQ ID NO: 11)

This peptide is modified by the chemical addition of any αGal epitope Galα1-3Galβ1-4GlcNAc-R₁—NHS as described below in Examples 22 to 32.

αGT KO mice bred in the C57B1/6 genetic background are primed by 2 or 3 intraperitoneal injections of 10⁸ RRBC to induce the production of anti-αGal antibodies. On week after the last RRBC immunization, animals receive three weekly subcutaneous immunizations of 5 µg of αGal$^{(+)}$ BORIS peptide without adjuvant. One week after immunization animals receive a subcutaneous injection of 10⁵ B16 cells in 100 µL saline and tumor growth is monitored over time. Animals are sacrificed when tumor volume is higher than 1000 mm³.

Example 22

Synthesis of αGal Epitope Galα1-3Galα1-4Glc-L₁-N-hydroxysuccinimide ester (NLG-αGal-001)

All commercial reagents and solvents were used as received without further purification. The reactions were monitored using thin layer chromatography using 0.25 mm EM Science silica gel plates (60F-254). The developed TLC plates were visualized by immersion in potassium permanganate solution followed by heating on a hot plate. Flash column chromatography was performed with Fisher Scientific silica gel grade 60, 230-400 mesh. ¹H NMR spectra were obtained with a Bruker DRX400 and Varian VXR300 respectively. ¹H NMR spectra were reported in parts per million (ppm) relative to CDCl3 (7.27 ppm) and CD3OD (4.80 ppm) as an internal reference.

Figure 3:
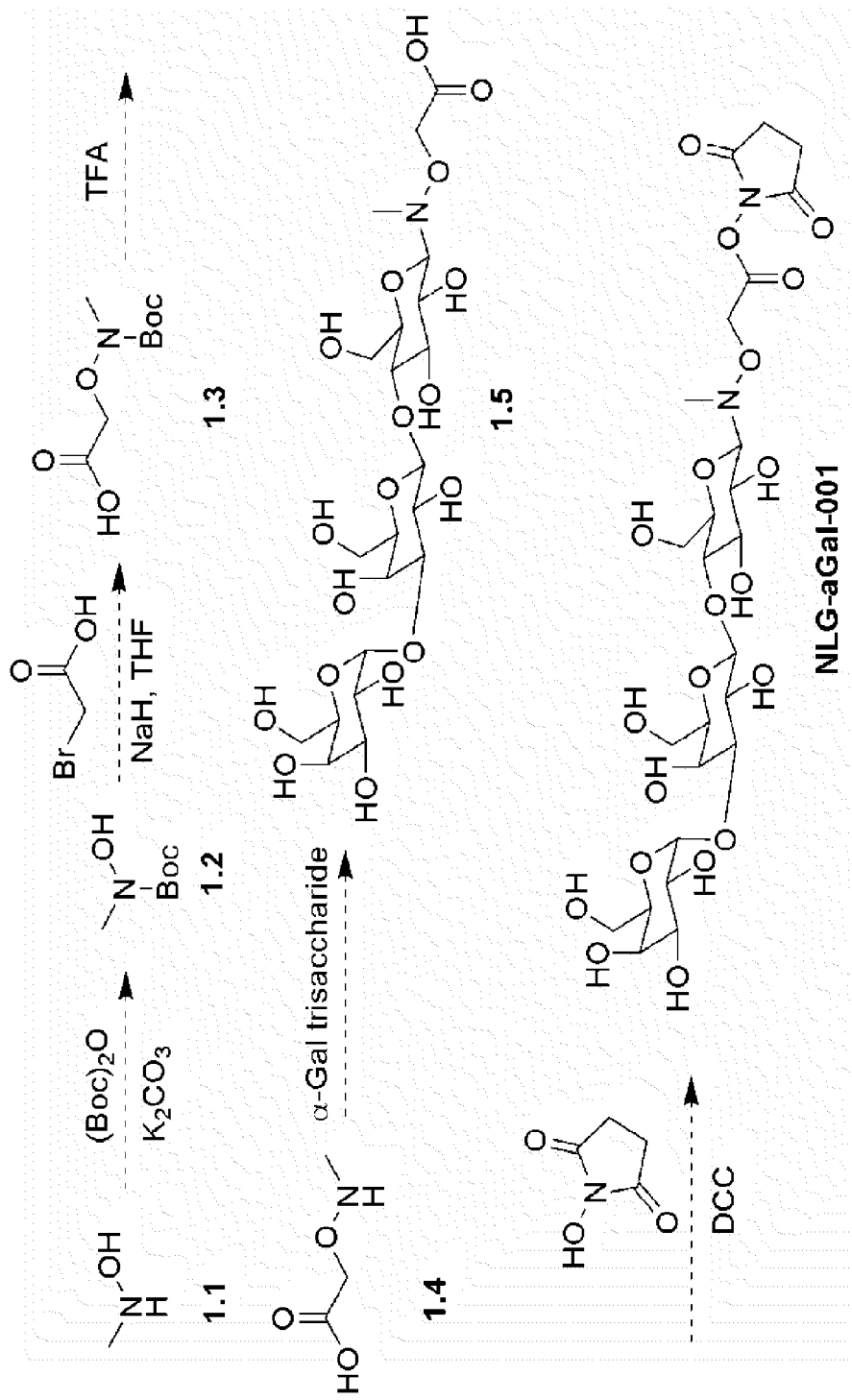
FIG. 3 is a schematic description of synthesis of αGal epitope NLG-αGal-001. See Example 22 for details.

A bifunctional linker was designed such that there is a secondary aminooxy group on one end and a carboxylic acid on the other end conformed by the structure COOH—R₁—O—NH—CH₃ wherein R₁ is any linear or branched alkyl group of 1 to 30 carbon atoms, wherein one or more carbon atoms in such alkyl group can be substituted by O, S, or N and wherein one or more hydrogens can be substituted by hydroxyl, carbonyl, alkyl, sulphydryl or amino groups. As shown in FIG. 3, the amine linker 1.4 was chosen for initial studies. The linker was synthesized in 2 steps from known compound N-boc-N-methylhydroxylamine. The aminooxy linker is treated with α-Gal in DMF:AcOH (1:1) to produce glycosylated product 1.5. Activation of carboxylic acid with NHS (N-hydroxysuccinimide) results in the formation of activated α-Gal epitope NLG-αGal-001.

Example 23

Synthesis of αGal Epitope Galα1-3Galα1-4Glc-L₁-N-hydroxysuccinimide ester (NLG-αGal-002)

Figure 4:
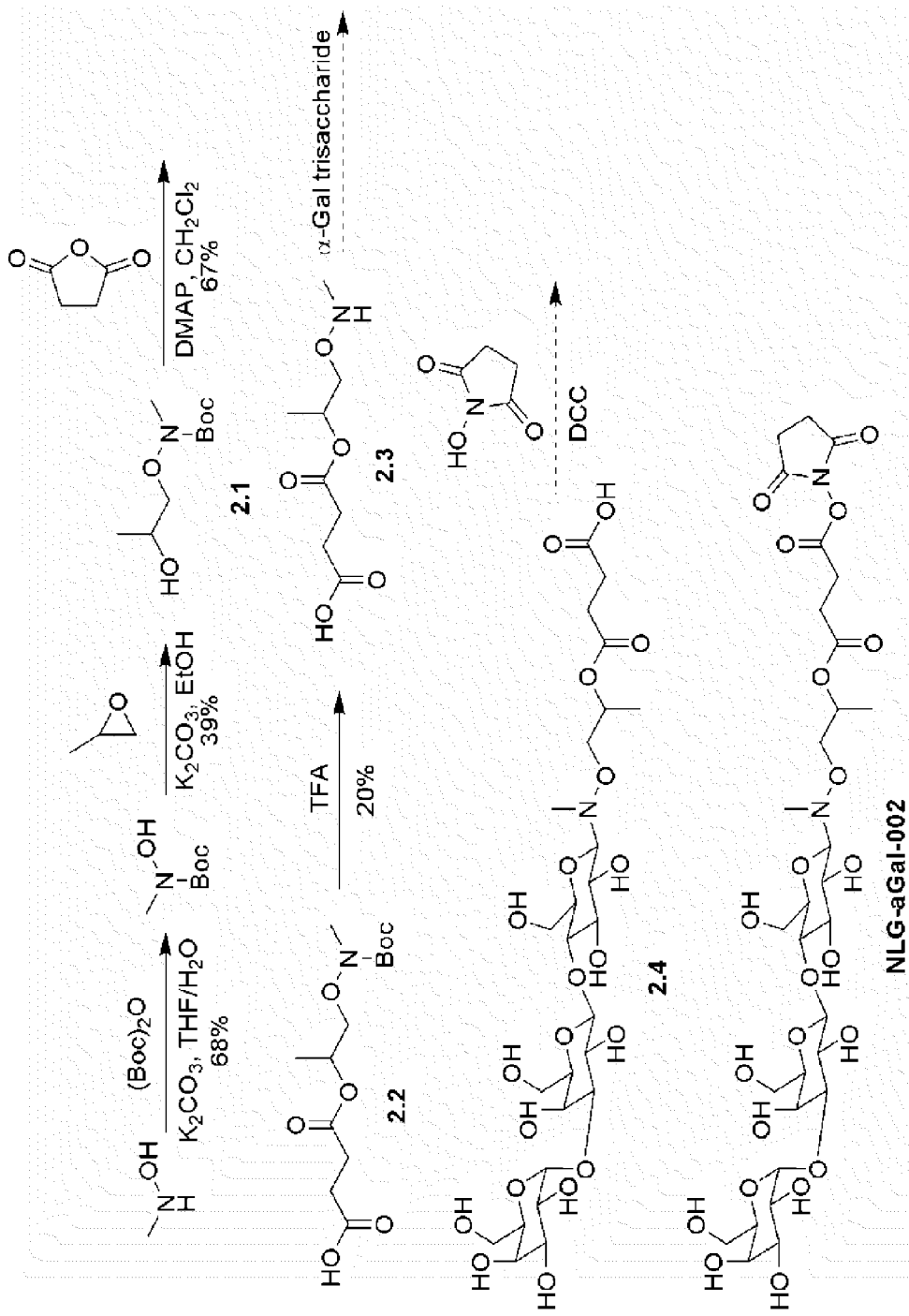
FIG. 4 is a schematic description of synthesis of αGal epitope NLG-αGal-002. See Examples 22-26 for details.
Figure 5:
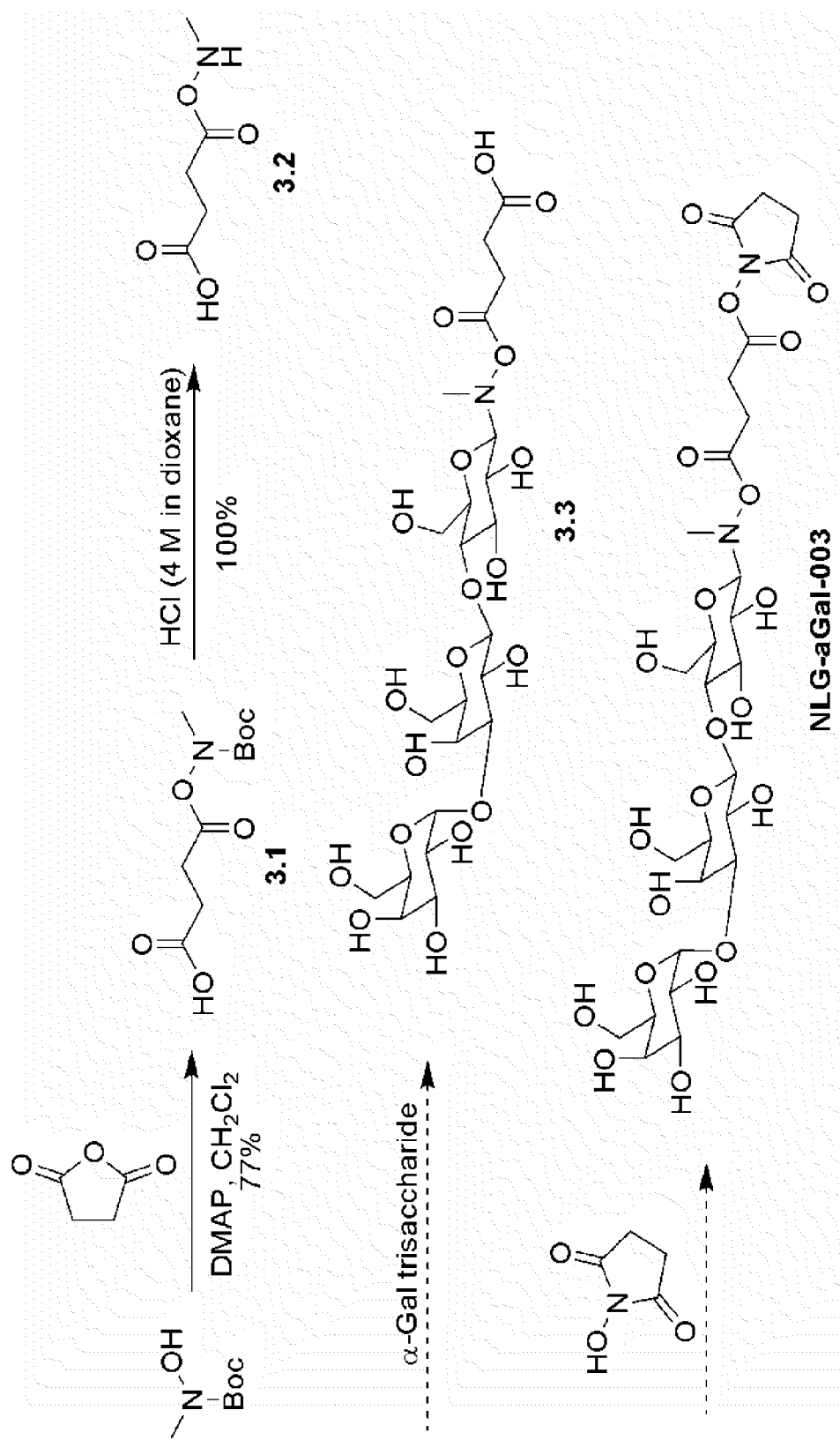
FIG. 5 is a schematic description of synthesis of αGal epitope NLG-αGal-003. See Examples 27-29 for details.
Figure 6:
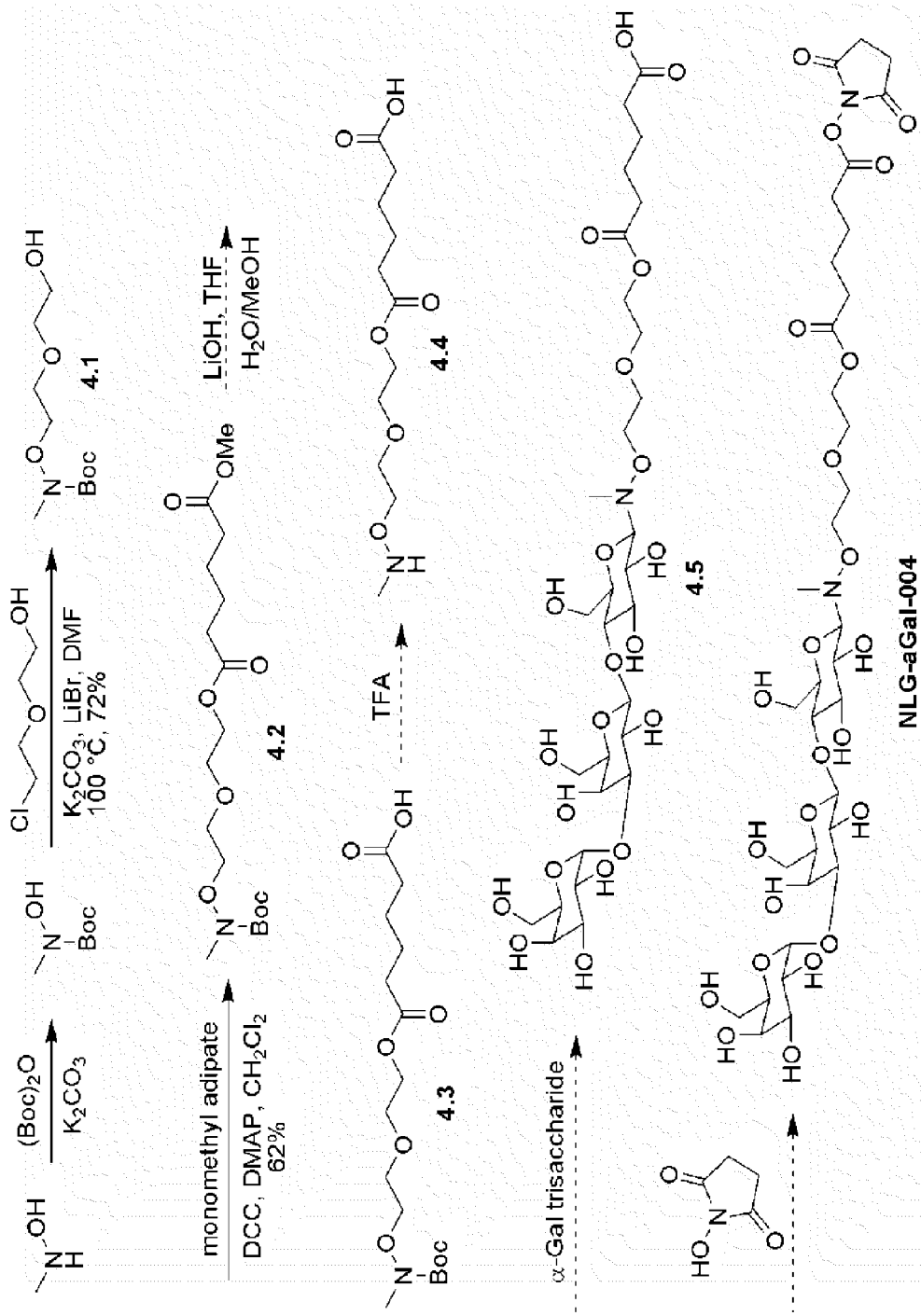
FIG. 6 is a schematic description of synthesis of αGal epitope NLG-αGal-004. See Examples 30-32 for details.
Figure 7:
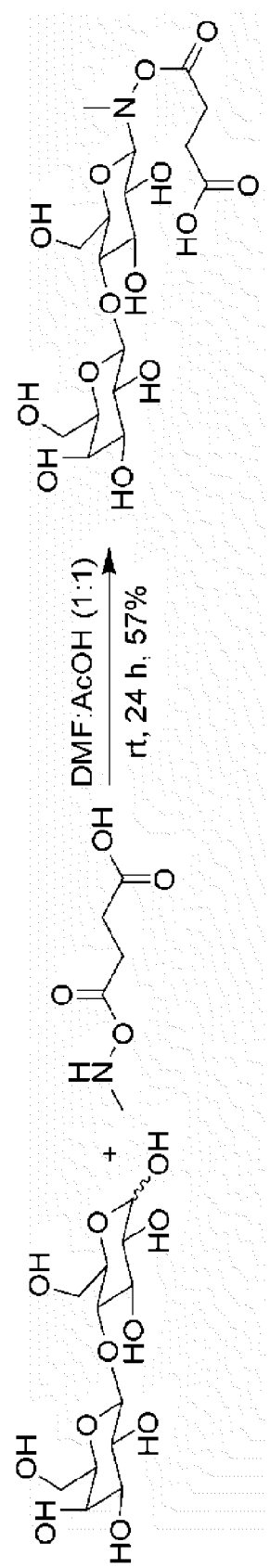
FIG. 7 is a schematic description of synthesis of 4-[(β-D-lactopyranosyl)(methyl)aminooxy]-4-oxobutanoic acid. See Examples 33 for details.

The αGal epitope NLG-αGal-002 was designed with an ester group within the linker region in order to facilitate the removal of this αGal trisacharide by intracellular esterases, following the synthesis scheme described in FIG. 4. The bifunctional linker 2.3 was synthesized in 4 steps from N-methylhydroxylamine. Glycosylation of α-Gal with the aminoxy linker 2.3 followed by activation of the terminal carboxylic acid with NHS would produce the desired α-Gal epitope.

Example 24

Synthesis of N-methyl-N-boc-(2-hydroxypropyl)hydroxylamine (Compound 2.1)

To a solution of N-methyl-N-Boc hydroxylamine (Beshara et. al. Org. Lett. 2005, 7, 5729 (444 mg, 3.02 mmol) and propylene oxide (0.25 mL, 3.62 mmol) in EtOH (8 mL) at room temperature was added K2CO3 (458 mg, 3.32 mmol). The reaction mixture was further stirred at room temperature for 16 h. The solvent was removed in vacuo and the crude product was purified by silica gel flash column chromatography using 25% EtOAc/hexane as eluent to yield the corresponding secondary alcohol as colorless oil (241 mg, 1.18 mmol, 39%). $^1$H NMR (CDCl$_3$, 400 MHz): δ (ppm) 1.08 (d, 3H, J=6.4 Hz), 1.45 (s, 9H), 3.05 (s, 3H), 3.45 (dd, 1H, J=9.6, 11.6 Hz), 3.78 (dd, 1H, J=2.4, 11.2 Hz), 3.90-3.96 (m, 1H), 4.17 (br s, 1H).

Example 25

Synthesis of 2,2,5,8-tetramethyl-4,10-dioxo-3,6,9-trioxa-5-azamidecan-13-oic acid (Compound 2.2)

To a solution of N-methyl-N-boc-(2-hydroxypropyl)hydroxylamine (227 mg, 1.11 mmol) in dichloromethane (4 mL) were added DMAP (41 mg, 0.333 mmol) and succinic anhydride (167 mg, 1.67 mmol). The resulting mixture was stirred for 20 h at room temperature. The reaction mixture was poured into a saturated solution of ammonium chloride (15 mL) and extracted with DCM (3×40 mL). The combined organic layer was washed with water and dried over sodium sulfate. The solvent was removed in vacuo and the crude product was purified by silica flash column chromatography using 40% EtOAc/hexane as eluent to give the product as a white solid (227 mg, 0.744 mmol, 67%). $^1$H NMR (CDCl$_3$, 400 MHz): δ (ppm) 1.14 (d, 3H, J=6.4 Hz), 1.45 (s, 9H), 2.51-2.57 (m, 4H), 2.91 (s, 3H), 3.77-3.79 (m, 2H), 5.04-5.11 (m, 1H).

Example 26

Synthesis of 4-(1-(methylaminooxy)propan-2-yloxy)-4-oxobutanoic acid (Compound 2.3)

2,2,5,8-Tetramethyl-4,10-dioxo-3,6,9-trioxa-5-azamidecan-13-oic acid (227 mg, 0.744 mmol) was dissolved in 4 mL TFA. The reaction mixture was stirred at room temperature for 4 h and concentrated. The crude product was purified by silica gel flash column chromatography using 12% MeOH/dichloromethane as eluent. The desired product was obtained as a colorless gel (30 mg, 0.146 mmol, 20%). $^1$H NMR (CD$_3$OD, 300 MHz): δ (ppm) 1.17 (d, 3H, J=6.6 Hz), 2.58 (s, 3H), 2.61 (s, 3H), 3.66 (d, 2H, J=5.4 Hz), 5.10-5.16 (m, 1H).

Example 27

Synthesis of αGal Epitope Galα1-3Galα1-4Glc-L$_1$-N-hydroxysuccinimide ester (NLG-αGal-003)

A different linker bearing an ester functionality in a different position of the linker can be formed by reacting hydroxylamine directly with succinic anhydride. As described in FIG. 5, treatment of N-methyl-N-boc hydroxylamine with succinic anhydride and DMAP resulted in carboxylic acid 3.1. Deprotection of Boc gave amine 3.2 in 100% yield. Conjugation of the linker with the αGal trisacharide was performed as described above for the synthesis of NLG-αGal-001 and NLG-αGal-002.

Example 28

Synthesis of 4-(tert-butoxycarbonyl(methyl)aminooxy)-4-oxobutanoic acid (Compound 3.1)

To a solution of N-methyl-N-boc hydroxylamine 3 (536 mg, 3.65 mmol) in ichloromethane (8 mL) were added DMAP (134 mg, 1.10 mmol) and succinic anhydride (548 mg, 5.48 mmol). The resulting mixture was stirred for 16 h at room temperature. The reaction mixture was poured into a saturated solution of ammonium chloride (10 mL) and extracted with ethyl acetate (2×40 mL). The combined organic layer was washed with water (20 mL) and dried over sodium sulfate. The solvent was removed in vacuo and the crude product was purified by silica flash column chromatography using 45% EtOAc/hexane as eluent to give the corresponding acid as a white solid (693 mg, 2.81 mmol, 77%). $^1$H NMR (CDCl$_3$, 400 MHz): δ (ppm) 1.42 (s, 9H), 2.65-2.70 (m, 4H), 3.17 (s, 3H).

Example 29

Synthesis of 4-(methylaminooxy)-4-oxobutanoic acid (Compound 3.2)

To a solution of 4-(tert-butoxycarbonyl(methyl)aminooxy)-4-oxobutanoic acid (96 mg, 0.389) in dioxane (3 mL) was added 4 M HCl solution in dioxane (2 mL). The reaction mixture was stirred at room temperature for 20 h and concentrated. The desired product was obtained as a white solid (72 mg, 0.389 mmol, 100%). $^1$H NMR (CD$_3$OD, 400 MHz): δ (ppm) 2.53-2.57 (m, 2H), 2.68-2.77 (m, 2H), 2.94 (s, 3H).

Example 30

Synthesis of αGal Epitope Galα1-3Galα1-4Glc-L$_1$-N-hydroxysuccinimide ester (NLG-αGal-004)

All the linkers proposed so far are short linker where the sugar moiety and peptide are separated by 4-8 carbon/oxygen atoms. To facilitate ester cleavage by intracellular esterases and solubility of the linker fragment we increased the spacing to 12 carbon/oxygen atoms. The new linker 4.4 would be synthesized according to Scheme 4 shown in FIG. 6. Treatment of N-methyl-N-boc hydroxylamine with 2-(2-chloroethoxy)ethanol gave primary alcohol 4.1 in 72% yield. The alcohol was coupled with monomethyl adipate in presence of DCC to produce ester 4.2 in 62% yield. Hydrolysis of methyl ester followed by deprotection of boc would result in linker 4.4. This linker would be coupled with αGal trisaccharide and then activated with N-hydroxy succinimide (NHS) to yield NLG-αGal-004.

Example 31

Synthesis of tert-butyl 2-(3-hydroxypropoxy)ethoxy(methyl)carbamate (Compound 4.1)

A mixture of N-Boc-N-methyl hydroxylamine (132 mg, 0.898 mmol), 2-(2-chloroethoxy)ethanol (168 mg, 1.35 mmol), K$_2$CO$_3$ (372 mg, 2.69 mmol) and LiBr (2 mg, 0.018 mmol) in DMF (3 mL) was heated at 100° C. and stirred for 16 h. The resulting mixture was cooled down to room temperature and filtered. The filtrate was concentrated and the residue was purified by silica gel flash column chromatography using 50% EtOAc/hexanes as eluent to afford the desired product as colorless oil (152 mg, 0.647 mmol, 72%). $^1$H NMR (CDCl$_3$, 400 MHz): δ (ppm) 1.45 (s, 9H), 2.68 (br s, 1H), 3.08 (s, 3H), 3.57-3.60 (m, 2H), 3.66-3.72 (m, 4H), 3.96-3.99 (m, 2H).

Example 32

Synthesis of methyl 2,2,5-trimethyl-4-oxo-3,6,9-trioxa-5-azaundecan-11-yl adipate (Compound 4.2)

To a solution of tert-butyl 2-(3-hydroxypropoxy)ethoxy (methyl)carbamate (152 mg, 0.646 mmol) and monomethyl adipate (104 mg, 0.646 mmol) in $CH_2Cl_2$ (4 mL) were added DCC (146 mg, 0.711 mmol) and DMAP (16 mg, 0.129 mmol). The reaction mixture was stirred at room temperature for 16 h and filtered. The solvent was removed under reduced pressure. The crude product was purified by silica gel flash column chromatography using 27% EtOAc/hexanes as eluent. The desired product was obtained as colorless oil (152 mg, 0.403 mmol, 62%). $^1$H NMR (CDCl$_3$, 400 MHz): δ (ppm) 1.41 (s, 9H), 1.56-1.60 (m, 4H), 2.25-2.27 (m, 4H), 3.03 (s, 3H), 3.58 (s, 3H), 3.59-3.63 (m, 4H), 3.91-3.94 (m, 2H), 4.14-4.16 (m, 2H).

Example 33

Synthesis of 4-[(β-D-lactopyranosyl)(methyl)aminooxy]-4-oxobutanoic acid

The methods described for the synthesis of activated αGal epitopes are generally applicable to any saccharide. As an additional example, the activation of lactose with linker of formula (II) was performed by the following procedure. A solution of Lactose (140 mg, 0.408 mmol) and 4-(methylaminooxy)-4-oxobutanoic acid (30 mg, 0.204) in DMF/AcOH (1:1) was stirred at room temperature for 24 h. After removal of the solvent under reduced pressure, the crude product was purified by silica flash column chromatography using 35% MeOH/EtOAc as eluent. The desired product was obtained as a white solid (54 mg, 0.121 mmol, 57%). $^1$H NMR (CD$_3$OD, 300 MHz): δ (ppm) 2.66 (s, 3H), 2.77-2.86 (m, 4H), 3.40-3.58 (m, 12H), 3.70-3.90 (m, 12H), 4.35 (d, 2H, J=7.5 Hz), 4.49 (d, 1H, J=7.8 Hz), 5.09 (d, 1H, J=3.6 Hz).

REFERENCES

Abdel-Motal, U., S. Wang, et al. (2006). "Increased immunogenicity of human immunodeficiency virus gp120 engineered to express Galα1-3Galbeta1-4GlcNAc-R epitopes." *J Virol* 80(14): 6943-51.

Ackerman, A. L., C. Kyritsis, R. Tampe and P. Cresswell (2005). "Access of soluble antigens to the endoplasmic reticulum can explain cross-presentation by dendritic cells." *Nat Immunol* 6(1): 107-13.

Antonia, S., J. J. Mule and J. S. Weber (2004). "Current developments of immunotherapy in the clinic." *Curr Opin Immunol* 16(2): 130-6.

Baumann, B. C., P. Forte, et al. (2004). "Lack of galactose-α-1,3-galactose expression on porcine endothelial cells prevents complement-induced lysis but not direct xenogeneic NK cytotoxicity." *J Immunol* 172(10): 6460-7.

Benatuil, L., J. Kaye, et al. (2005). "The influence of natural antibody specificity on antigen immunogenicity." *Eur J Immunol* 35(9): 2638-47.

Berzofsky, J. A. (1993). "Epitope selection and design of synthetic vaccines. Molecular approaches to enhancing immunogenicity and cross-reactivity of engineered vaccines." *Ann N Y Acad Sci* 690: 256-64.

Berzofsky, J. A., J. D. Ahlers and I. M. Belyakov (2001). "Strategies for designing and optimizing new generation vaccines." *Nat Rev Immunol* 1(3): 209-19.

Berzofsky, J. A., M. Terabe, et al. (2004). "Progress on new vaccine strategies for the immunotherapy and prevention of cancer." *J Clin Invest* 113(11): 1515-25.

Beshara et. al. (2005) Org. Lett. 7, 5729.

Bocchia, M., P. A. Wentworth, et al. (1995). "Specific binding of leukemia oncogene fusion protein peptides to HLA class I molecules." *Blood* 85(10): 2680-4.

Bocchia, M., T. Korontsvit, et al. (1996). "Specific human cellular immunity to bcr-abl oncogene-derived peptides." *Blood* 87(9): 3587-92.

Brinckerhoff, L. H., V. V. Kalashnikov, et al. (1999). "Terminal modifications inhibit proteolytic degradation of an immunogenic MART-1(27-35) peptide: implications for peptide vaccines." *Int J Cancer* 83(3): 326-34.

Brunner, C., J. Seiderer, et al. (2000). "Enhanced dendritic cell maturation by TNF-α or cytidine-phosphate-guanosine DNA drives T cell activation in vitro and therapeutic anti-tumor immune responses in vivo." *J Immunol* 165 (11): 6278-86.

Cathcart, K., J. Pinilla-Ibarz, et al. (2004). "A multivalent bcr-abl fusion peptide vaccination trial in patients with chronic myeloid leukemia." *Blood* 103(3): 1037-42.

Chen, J. L., P. R. Dunbar, et al. (2000). "Identification of NY-ESO-1 peptide analogues capable of improved stimulation of tumor-reactive CTL." *J Immunol* 165(2): 948-55.

Chen, Z. C., M. Tanemura and U. Galili (2001). "Synthesis of α-gal epitopes αGalα1-3Galbeta1-4GlcNAc-R) on human tumor cells by recombinant α1,3galactosyltransferase produced in *Pichia pastoris*." *Glycobiology* 11(7): 577-86.

Chianese-Bullock, K. A., E. M. Woodson, et al. (2005). "Autoimmune toxicities associated with the administration of antitumor vaccines and low-dose interleukin-2." *J Immunother* 28(4): 412-9.

Clynes, R., Y. Takechi, et al. (1998). "Fc receptors are required in passive and active immunity to melanoma." *Proc Natl Acad Sci USA* 95(2): 652-6.

Cole, D. J., M. C. Wilson, et al. (1996). "Phase I study of recombinant CEA vaccinia virus vaccine with post vaccination CEA peptide challenge." *Hum Gene Ther* 7(11): 1381-94.

Cormier, J. N., M. L. Salgaller, et al. (1997). "Enhancement of cellular immunity in melanoma patients immunized with a peptide from MART-1/Melan A." *Cancer J Sci Am* 3(1): 37-44.

Cresswell, P. (2005). "Antigen processing and presentation." *Immunol Rev* 207: 5-7.

Cresswell, P., A. L. Ackerman, et al. (2005). "Mechanisms of MHC class I-restricted antigen processing and cross-presentation." *Immunol Rev* 207: 145-57.

Davin, J. C., M. Malaise, J. Foidart and P. Mahieu (1987). "Anti-α-galactosyl antibodies and immune complexes in children with Henoch-Schonlein purpura or IgA nephropathy." *Kidney Int* 31(5): 1132-9.

Disis, M. L., T. A. Gooley, et al. (2002). "Generation of T-cell immunity to the HER-2/neu protein after active immunization with HER-2/neu peptide-based vaccines." *J Clin Oncol* 20(11): 2624-32.

Dranoff, G. (2002). "GM-CSF-based cancer vaccines." *Immunol Rev* 188: 147-54.

Dyall, R., W. B. Bowne, et al. (1998). "Heteroclitic immunization induces tumor immunity." *J Exp Med* 188(9): 1553-61.

Fang, J., J. Li, et al. (1998). "Highly efficient chemoenzymatic synthesis of α-galactosyl epitopes with a recombinant a(1-3)-galactosyltransferase." *J. Am. Chem. Soc.* 120 (27): 6635.

Fong, L., Y. Hou, et al. (2001). "Altered peptide ligand vaccination with Flt3 ligand expanded dendritic cells for tumor immunotherapy." *Proc Natl Acad Sci USA* 98(15): 8809-14.

Galili, U., E. A. Rachmilewitz, A. Peleg and I. Flechner (1984). "A unique natural human IgG antibody with anti-α-galactosyl specificity." *J Exp Med* 160(5): 1519-31.

Galili, U., B. A. Macher, J. Buehler and S. B. Shohet (1985). "Human natural anti-α-galactosyl IgG. II. The specific recognition of α(1----3)-linked galactose residues." *J Exp Med* 162(2): 573-82.

Galili, U., J. Buehler, S. B. Shohet and B. A. Macher (1987). "The human natural anti-αGal IgG. III. The subtlety of immune tolerance in man as demonstrated by crossreactivity between natural anti-Gal and anti-B antibodies." *J Exp Med* 165(3): 693-704.

Galili, U., S. B. Shohet, et al. (1988). "Man, apes, and Old World monkeys differ from other mammals in the expression of α-galactosyl epitopes on nucleated cells." *J Biol Chem* 263(33): 17755-62.

Galili, U., F. Anaraki, et al. (1993). "One percent of human circulating B lymphocytes are capable of producing the natural anti-Gal antibody." *Blood* 82(8): 2485-93.

Galili, U., P. M. Repik, et al. (1996). "Enhancement of antigen presentation of influenza virus hemagglutinin by the natural human anti-Gal antibody." *Vaccine* 14(4): 321-8.

Galili, U. and D. C. LaTemple (1997). "Natural anti-Gal antibody as a universal augmenter of autologous tumor vaccine immunogenicity." *Immunol Today* 18(6): 281-5.

Galili, U., Z. C. Chen, et al. (2001). "Preparation of autologous leukemia and lymphoma vaccines expressing α-gal epitopes." *J Hematother Stem Cell Res* 10(4): 501-11.

Galili, U. (2004). "Autologous tumor vaccines processed to express α-gal epitopes: a practical approach to immunotherapy in cancer." *Cancer Immunol Immunother.*

Gattinoni, L., D. J. Powell, Jr., S. A. Rosenberg and N. P. Restifo (2006). "Adoptive immunotherapy for cancer: building on success." *Nat Rev Immunol* 6(5): 383-93.

Hanessian, S., H. K. Huynh, et al. (2001a). "Synthesis of Gal determinant epitopes, their glycomimetic variants, and trimeric clusters—relevance to tumor associated antigens and discordant xenografts." *Tetrahedron* 57: 3281-3290.

Hanessian, S., O. Saavedra, et al. (2001b). "Practical syntheses of B disaccharide and linear B type 2 trisaccharide—non-primate epitope markers recognized by human anti-a-Gal antibodies causing hyperacute rejection of xenotransplants." *Tetrahedron* 57: 3267-3280.

Heath, W. R. and F. R. Carbone (2001). "Cross-presentation, dendritic cells, tolerance and immunity." *Annu Rev Immunol* 19: 47-64.

Heath, W. R., G. T. Belz, et al. (2004). "Cross-presentation, dendritic cell subsets, and the generation of immunity to cellular antigens." *Immunol Rev* 199: 9-26.

Henion, T. R., B. A. Macher, F. Anaraki and U. Galili (1994). "Defining the minimal size of catalytically active primate α1,3 galactosyltransferase: structure-function studies on the recombinant truncated enzyme." *Glycobiology* 4(2): 193-201.

Henion, T. R., W. Gerhard, F. Anaraki and U. Galili (1997). "Synthesis of α-gal epitopes on influenza virus vaccines, by recombinant α1,3 galactosyltransferase, enables the formation of immune complexes with the natural anti-Gal antibody." *Vaccine* 15(11): 1174-82.

Hong, J. A., Y. Kang, et al. (2005). "Reciprocal binding of CTCF and BORIS to the NY-ESO-1 promoter coincides with derepression of this cancer-testis gene in lung cancer cells." *Cancer Res* 65(17): 7763-74.

Janczuk, A. J., W. Zhang, et al. (2002). "The synthesis of deoxy-α-Gal epitope derivatives for the evaluation of an anti-α-Gal antibody binding." *Carbohydr Res* 337(14): 1247-59.

Joziasse, D. H., J. H. Shaper, et al. (1989). "Bovine α1----3-galactosyltransferase: isolation and characterization of a cDNA clone. Identification of homologous sequences in human genomic DNA." *J Biol Chem* 264(24): 14290-7.

Joziasse, D. H., N. L. Shaper, et al. (1992). "Murine α1,3-galactosyltransferase. A single gene locus specifies four isoforms of the enzyme by alternative splicing." *J Biol Chem* 267(8): 5534-41.

Joziasse, D. H. and R. Oriol (1999). "Xenotransplantation: the importance of the Galα1,3Gal epitope in hyperacute vascular rejection." *Biochim Biophys Acta* 1455(2-3): 403-18.

Kloetzel, P. M. (2001). "Antigen processing by the proteasome." *Nat Rev Mol Cell Biol* 2(3): 179-87.

Kloetzel, P. M. (2004). "The proteasome and MHC class I antigen processing." *Biochim Biophys Acta* 1695(1-3): 225-33.

Kloetzel, P. M. and F. Ossendorp (2004). "Proteasome and peptidase function in MHC-class-1-mediated antigen presentation." *Curr Opin Immunol* 16(1): 76-81.

Koike, C., J. J. Fung, et al. (2002). "Molecular basis of evolutionary loss of the α1,3-galactosyltransferase gene in higher primates." *J Biol Chem* 277(12): 10114-20.

Kruger, E., U. Kuckelkorn, A. Sijts and P. M. Kloetzel (2003). "The components of the proteasome system and their role in MHC class I antigen processing." *Rev Physiol Biochem Pharmacol* 148: 81-104.

Lanzavecchia, A. (1993). "Identifying strategies for immune intervention." *Science* 260(5110): 937-44.

Larsen, R. D., C. A. Rivera-Marrero, et al. (1990). "Frameshift and nonsense mutations in a human genomic sequence homologous to a murine UDP-Gal:beta-D-Gal (1,4)-D-GlcNAc α-(1,3)-galactosyltransferase cDNA." *J Biol Chem* 265(12): 7055-61.

LaTemple, D. C., T. R. Henion, F. Anaraki and U. Galili (1996). "Synthesis of αgalactosyl epitopes by recombinant α1,3galactosyl transferase for opsonization of human tumor cell vaccines by anti-galactose." *Cancer Res* 56(13): 3069-74.

LaTemple, D. C., J. T. Abrams, S. Y. Zhang and U. Galili (1999). "Increased immunogenicity of tumor vaccines complexed with anti-Gal: studies in knockout mice for α1,3galactosyltransferase." *Cancer Res* 59(14): 3417-23.

LaTemple, D. C. and U. Galili (1999). "Enhancement of autologous tumor vaccine immunogenicity by anti-Gal." *Subcell Biochem* 32: 361-79.

Li, P., J. L. Gregg, et al. (2005). "Compartmentalization of class II antigen presentation: contribution of cytoplasmic and endosomal processing." *Immunol Rev* 207: 206-17.

Link, C. J., Jr., T. Seregina, et al. (1998). "Eliciting hyperacute xenograft response to treat human cancer: α-(1,3) galactosyltransferase gene therapy." *Anticancer Res* 18(4A): 2301-8.

Lobanenkov, V. V., D. Loukinov and H. C. Morse, 3rd (2005). Brother of the regulator of imprinted sites (BORIS). US, The Government of USA.

Loukinov, D., A. Ghochikyan, et al. (2006). "Antitumor efficacy of DNA vaccination to the epigenetically acting tumor promoting transcription factor BORIS and CD80 molecular adjuvant." *J Cell Biochem* 98(5): 1037-43.

Loukinov, D. I., E. Pugacheva, et al. (2002). "BORIS, a novel male germ-line-specific protein associated with epigenetic reprogramming events, shares the same 11-zinc-finger domain with CTCF, the insulator protein involved in reading imprinting marks in the soma." *Proc Natl Acad Sci USA* 99(10): 6806-11.

Marchand, M., N. van Baren, et al. (1999). "Tumor regressions observed in patients with metastatic melanoma treated with an antigenic peptide encoded by gene MAGE-3 and presented by HLA-A1." *Int J Cancer* 80(2): 219-30.

Maruyama, S., E. Cantu, 3rd, et al. (1999). "Interaction of baboon anti-α-galactosyl antibody with pig tissues." *Am J Pathol* 155(5): 1635-49.

Matzinger, P. (2002). "The danger model: a renewed sense of self." *Science* 296(5566): 301-5.

Mautino, M. R. and R. A. Morgan (2002). "Enhanced inhibition of human immunodeficiency virus type 1 replication by novel lentiviral vectors expressing human immunodeficiency virus type 1 envelope antisense RNA." *Hum Gene Ther* 13(9): 1027-37.

Mintz, B. and W. K. Silvers (1967). ""Intrinsic" immunological tolerance in allophenic mice." *Science* 158(807): 1484-6.

Morisaki, T., K. Matsumoto, et al. (2003). "Dendritic cell-based combined immunotherapy with autologous tumor-pulsed dendritic cell vaccine and activated T cells for cancer patients: rationale, current progress, and perspectives." *Hum Cell* 16(4): 175-82.

Naftzger, C., Y. Takechi, et al. (1996). "Immune response to a differentiation antigen induced by altered antigen: a study of tumor rejection and autoimmunity." *Proc Natl Acad Sci USA* 93(25): 14809-14.

Naicker, K. P., H. Li, et al. (2004). "Design and synthesis of (X Gal-conjugated peptide T20 as novel antiviral agent for HIV-immunotargeting." *Org Biomol Chem* 2(5): 660-4.

Nilsson, K. G. I. (1997). "Glycosidase-catalysed synthesis of di- and trisaccharide derivatives related to antigens involved in the hyperacute rejection of xenotransplants." *Tetrahedron Letters* 38(1): 133-136.

Novellino, L., C. Castelli and G. Parmiani (2005). "A listing of human tumor antigens recognized by T cells: March 2004 update." *Cancer Immunol Immunother* 54(3): 187-207.

Overwijk, W. W., M. R. Theoret, et al. (2003). "Tumor regression and autoimmunity after reversal of a functionally tolerant state of self-reactive CD8+ T cells." *J Exp Med* 198(4): 569-80.

Palliser, D., E. Guillen, M. Ju and H. N. Eisen (2005). "Multiple intracellular routes in the cross-presentation of a soluble protein by murine dendritic cells." *J Immunol* 174(4): 1879-87.

Pardoll, D. M. (1993). "Cancer vaccines." *Immunol Today* 14(6): 310-6.

Parkhurst, M. R., M. L. Salgaller, et al. (1996). "Improved induction of melanoma-reactive CTL with peptides from the melanoma antigen gp100 modified at HLA-A*0201-binding residues." *J Immunol* 157(6): 2539-48.

Parmiani, G., C. Castelli, et al. (2002). "Cancer immunotherapy with peptide-based vaccines: what have we achieved? Where are we going?" *J Natl Cancer Inst* 94(11): 805-18.

Perez-Diez, A., P. J. Spiess, et al. (2002). "Intensity of the vaccine-elicited immune response determines tumor clearance." *J Immunol* 168(1): 338-47.

Phan, G. Q., C. E. Touloukian, et al. (2003). "Immunization of patients with metastatic melanoma using both class I- and class II-restricted peptides from melanoma-associated antigens." *J Immunother* 26(4): 349-56.

Phillips, M. I. (2002). Gene therapy methods, Academic Press.

Pinilla-Ibarz, J., K. Cathcart, et al. (2000). "Vaccination of patients with chronic myelogenous leukemia with bcr-abl oncogene breakpoint fusion peptides generates specific immune responses." *Blood* 95(5): 1781-7.

Posekany, K. J., H. K. Pittman, et al. (2004). "Suppression of Lewis lung tumor development in α1,3 galactosyltransferase knock-out mice." *Anticancer Res* 24(2B): 605-12.

Rafiq, K., A. Bergtold and R. Clynes (2002). "Immune complex-mediated antigen presentation induces tumor immunity." *J Clin Invest* 110(1): 71-9.

Ramos, D., P. Rollin and W. Klaffke (2001). "Chemoenzymatic synthesis of neoglycopeptides: application to an α-Gal-terminated neoglycopeptide." *J Org Chem* 66(9): 2948-56.

Reddy, G. V., R. K. Jain, B. S. Bhatti and K. L. Matta (1994). "Synthesis of α-D-galactopyranosyl-linked oligosaccharides containing the α-Gal-->beta-Gal-->GlcNAc sequence employing methyl-2,3,4,6-tetra-O-(4-methoxybenzyl)-1-thio-beta-D-galactopyranoside as an efficient glycosyl donor." *Carbohydr Res* 263(1): 67-77.

Renkvist, N., C. Castelli, P. F. Robbins and G. Parmiani (2001). "A listing of human tumor antigens recognized by T cells." *Cancer Immunol Immunother* 50(1): 3-15.

Rivoltini, L., Y. Kawakami, et al. (1995). "Induction of tumor-reactive CTL from peripheral blood and tumor-infiltrating lymphocytes of melanoma patients by in vitro stimulation with an immunodominant peptide of the human melanoma antigen MART-1." *J Immunol* 154(5): 2257-65.

Rivoltini, L., P. Squarcina, et al. (1999). "A superagonist variant of peptide MART1/Melan A27-35 elicits anti-melanoma CD8+ T cells with enhanced functional characteristics: implication for more effective immunotherapy." *Cancer Res* 59(2): 301-6.

Rock, K. L., I. A. York and A. L. Goldberg (2004). "Post-proteasomal antigen processing for major histocompatibility complex class I presentation." *Nat Immunol* 5(7): 670-7.

Rosenberg, S. A., J. C. Yang, et al. (1998a). "Immunologic and therapeutic evaluation of a synthetic peptide vaccine for the treatment of patients with metastatic melanoma." *Nat Med* 4(3): 321-7.

Rosenberg, S. A., Y. Zhai, et al. (1998b). "Immunizing patients with metastatic melanoma using recombinant adenoviruses encoding MART-1 or gp100 melanoma antigens." *Natl Cancer Inst* 90(24): 1894-900.

Rosenberg, S. A., J. C. Yang and N. P. Restifo (2004). "Cancer immunotherapy: moving beyond current vaccines." *Nat Med* 10(9): 909-15.

Rossi, G. R., M. R. Mautino, et al. (2005a). "Effective treatment of preexisting melanoma with whole cell vaccines expressing α(1,3)-galactosyl epitopes." *Cancer Res* 65(22): 10555-61.

Rossi, G. R., R. C. Unfer, T. Seregina and C. J. Link (2005b). "Complete protection against melanoma in absence of autoimmune depigmentation after rejection of melanoma cells expressing α(1,3)galactosyl epitopes." *Cancer Immunol Immunother* 54: 999-1009.

Sandrin, M. S., H. A. Vaughan, P. L. Dabkowski and I. F. McKenzie (1993). "Anti-pig IgM antibodies in human serum react predominantly with Gal(α1-3αGal epitopes." *Proc Natl Acad Sci USA* 90(23): 11391-5.

Scanlan, M. J., A. O. Gure, et al. (2002). "Cancer/testis antigens: an expanding family of targets for cancer immunotherapy." *Immunol Rev* 188: 22-32.

Schaapherder, A. F., M. R. Daha, et al. (1994). "Antibody-dependent cell-mediated cytotoxicity against porcine endothelium induced by a majority of human sera." *Transplantation* 57(9): 1376-82.

Schlom, J., J. Kantor, et al. (1996). "Strategies for the development of recombinant vaccines for the immunotherapy of breast cancer." *Breast Cancer Res Treat* 38(1): 27-39.

Schmidt, F. R. (2004). "Recombinant expression systems in the pharmaceutical industry." *Appl Microbiol Biotechnol* 65(4): 363-72.

Schnurr, M., Q. Chen, et al. (2005). "Tumor antigen processing and presentation depend critically on dendritic cell type and the mode of antigen delivery." *Blood* 105(6): 2465-72.

Shao, J., T. Hayashi and P. G. Wang (2003). "Enhanced production of α-galactosyl epitopes by metabolically engineered *Pichia pastoris*." *Appl Environ Microbiol* 69(9): 5238-42.

Sharma, A., J. Okabe, et al. (1996). "Reduction in the level of Gal(α1,3)Gal in transgenic mice and pigs by the expression of an α(1,2)fucosyltransferase." *Proc Natl Acad Sci USA* 93(14): 7190-5.

Simpson, A. J., O. L. Caballero, et al. (2005). "Cancer/testis antigens, gametogenesis and cancer." *Nat Rev Cancer* 5(8): 615-25.

Soares, M. M., V. Mehta and O. J. Finn (2001). "Three different vaccines based on the 140-amino acid MUC1 peptide with seven tandemly repeated tumor-specific epitopes elicit distinct immune effector mechanisms in wild-type versus MUC1-transgenic mice with different potential for tumor rejection." *J Immunol* 166(11): 6555-63.

Sparwasser, T., E. S. Koch, et al. (1998). "Bacterial DNA and immunostimulatory CpG oligonucleotides trigger maturation and activation of murine dendritic cells." *Eur J Immunol* 28(6): 2045-54.

Speir, J. A., U. M. Abdel-Motal, M. Jondal and I. A. Wilson (1999). "Crystal structure of an MHC class I presented glycopeptide that generates carbohydrate-specific CTL." *Immunity* 10(1): 51-61.

Strahan, K. M., F. Gu, L. Andersson and K. Gustafsson (1995a). "Pig α1,3galactosyltransferase: sequence of a full-length cDNA clone, chromosomal localisation of the corresponding gene, and inhibition of expression in cultured pig endothelial cells." *Transplant Proc* 27(1): 245-6.

Strahan, K. M., F. Gu, et al. (1995b). "cDNA sequence and chromosome localization of pig α1,3 galactosyltransferase." *Immunogenetics* 41(2-3): 101-5.

Taylor, S. G., I. F. McKenzie and M. S. Sandrin (2003). "Characterization of the rat α(1,3)galactosyltransferase: evidence for two independent genes encoding glycosyltransferases that synthesize Galα(1,3)Gal by two separate glycosylation pathways." *Glycobiology* 13(5): 327-37.

Thall, A. D., P. Maly and J. B. Lowe (1995). "Oocyte Galα1, 3Gal epitopes implicated in sperm adhesion to the zona pellucida glycoprotein ZP3 are not required for fertilization in the mouse." *J Biol Chem* 270(37): 21437-40.

Tourdot, S., A. Scardino, et al. (2000). "A general strategy to enhance immunogenicity of low-affinity HLA-A2. 1-associated peptides: implication in the identification of cryptic tumor epitopes." *Eur J Immunol* 30(12): 3411-21.

Unfer, R. C., D. Hellrung and C. J. Link, Jr. (2003). "Immunity to the α(1,3)galactosyl epitope provides protection in mice challenged with colon cancer cells expressing α(1,3) galactosyl-transferase: a novel suicide gene for cancer gene therapy." *Cancer Res* 63(5): 987-93.

Vic, G., C. H. Tran, M. Scigelove and D. H. G. Crout (1997). "Glycosidase-catalysed synthesis of oligosaccharides: a one step synthesis of lactosamine and of the linear B type 2 trisaccharide α-D-Gal-(1->3)-b-D-Gal-(1->4)-b-D-GlcNAcSEt involved in the hyperacute rejection response in xenotransplantation from pigs to man and as the specific receptor for toxin A from *Clostridium difficile*." *Chemical Communications* 1997(2): 169-170.

Vijayasaradhi, S. and A. N. Houghton (1991). "Purification of an autoantigenic 75-kDa human melanosomal glycoprotein." *Int J Cancer* 47(2): 298-303.

Wang, J.-Q., X. Chen, et al. (1999). "Enhanced inhibition of human anti-Gal antibody binding to mammalian cells by synthetic a-Gal epitope polymers." *J. Am. Chem. Soc.* 121 (36): 8174-8181.

Watier, H., J. M. Guillaumin, et al. (1996a). "Removal of terminal α-galactosyl residues from xenogeneic porcine endothelial cells. Decrease in complement-mediated cytotoxicity but persistence of IgG1-mediated antibody-dependent cell-mediated cytotoxicity." *Transplantation* 62(1): 105-13.

Watier, H., J. M. Guillaumin, et al. (1996b). "Human NK cell-mediated direct and IgG-dependent cytotoxicity against xenogeneic porcine endothelial cells." *Transpl Immunol* 4(4): 293-9.

Weber, J. S., F. L. Hua, et al. (1999). "A phase I trial of an HLA-A1 restricted MAGE-3 epitope peptide with incomplete Freund's adjuvant in patients with resected high-risk melanoma." *J Immunother* 22(5): 431-40.

Werdelin, O., M. Meldal and T. Jensen (2002). "Processing of glycans on glycoprotein and glycopeptide antigens in antigen-presenting cells." *Proc Natl Acad Sci USA* 99(15): 9611-3.

Werner, R. G., W. Noe, K. Kopp and M. Schluter (1998). "Appropriate mammalian expression systems for biopharmaceuticals." *Arzneimittelforschung* 48(8): 870-80.

Young, W. B. and C. J. Link, Jr. (2000). "Chimeric retroviral helper virus and picornavirus IRES sequence to eliminate DNA methylation for improved retroviral packaging cells." *J Virol* 74(11): 5242-9.

Zaremba, S., E. Barzaga, et al. (1997). "Identification of an enhancer agonist cytotoxic T lymphocyte peptide from human carcinoembryonic antigen." *Cancer Res* 57(20): 4570-7.

What is claimed is:

1. A method for inducing an antitumor immune response in a patient comprising administering to the patient an effective amount of an synthetic immunogen comprising a tumor associated antigen or an immunogenic fragment thereof known to be capable of eliciting tumor associated antigen specific CD4+ and/or CD8+ immune responses, which has been conjugated to at least one synthetic peptide of 1-20 amino acids in length chemically modified in vitro to include one or more αGal epitopes.

2. The method of claim 1, wherein the tumor associated antigen or immunogenic fragment thereof is conjugated to said at least one peptide at its amino-terminus or carboxy-terminus.

3. The method of claim 1, wherein the tumor associated antigen or immunogenic fragment thereof is conjugated to at least two of said peptides at both its amino-terminus and its carboxy-terminus.

4. The method of claim 1, wherein said at least one peptide is conjugated to the tumor associated antigen or immunogenic fragment thereof by direct linkage to an amino acid selected from the group consisting of cysteine, lysine, serine, and threonine.

5. The method of claim 1, wherein said at least one peptide is conjugated to the tumor associated antigen or immunogenic fragment thereof by direct linkage to the primary amino group at its amino-terminus.

6. The method of claim 1, wherein said at least one peptide comprises an endopeptidase amino acid consensus sequence.

7. The method of claim 1, wherein said at least one peptide comprises at least one acceptor amino acid of an αGal epitope selected from the group consisting of lysine, cysteine, homocysteine, serine, threonine and glutamine, at least one of which has been chemically modified in vitro to be linked to an αGal epitope.

8. The method of claim 1, wherein said immunogenic fragment comprises 7-20 contiguous amino acids of the amino acid sequence of the tumor associated antigen.

9. The method of claim 1, wherein the structure of said one or more αGal epitopes as conjugated to the tumor associated antigen or immunogenic fragment thereof is Galα(1-3)Galβ(1,4)GlcNAc-R; wherein R is the tumor associated antigen or immunogenic fragment thereof.

* * * * *

SEQUENCE LISTING

<160> NUMBER OF SEQ ID NOS: 83

<210> SEQ ID NO 1
<211> LENGTH: 36
<212> TYPE: DNA
<213> ORGANISM: Artificial Sequence
<220> FEATURE:
<223> OTHER INFORMATION: Description of artificial sequence: forward primer for amplifying alpha GT

```
<400> SEQUENCE: 1
acaaaagctt gacatggatg tcaagggaaa agtaat                              36

<210> SEQ ID NO 2
<211> LENGTH: 28
<212> TYPE: DNA
<213> ORGANISM: Artificial Sequence
<220> FEATURE:
<223> OTHER INFORMATION: Description of artificial sequence: reverse
      primer for amplifying GT

<400> SEQUENCE: 2
aattatcgat tcagacatta tttctaac                                       28

<210> SEQ ID NO 3
<211> LENGTH: 21
<212> TYPE: DNA
<213> ORGANISM: Artificial Sequence
<220> FEATURE:
<223> OTHER INFORMATION: Description of artificial sequence: forward
      primer for amplifying human phosphoglycerate kinase (PGK) promoter

<400> SEQUENCE: 3
caggaattca cggggttggg g                                              21

<210> SEQ ID NO 4
<211> LENGTH: 30
<212> TYPE: DNA
<213> ORGANISM: Artificial Sequence
<220> FEATURE:
<223> OTHER INFORMATION: Description of artificial sequence: reverse
      primer for amplifying human phosphoglycerate kinase (PGK) promoter

<400> SEQUENCE: 4
tgacgtacga ttagcttgat catccccctg                                     30

<210> SEQ ID NO 5
<211> LENGTH: 36
<212> TYPE: DNA
<213> ORGANISM: Artificial Sequence
<220> FEATURE:
<223> OTHER INFORMATION: Description of artificial sequence: forward
      primer for amplifying murine alpha GT

<400> SEQUENCE: 5
acaaaagctt gacatggatg tcaagggaaa agtaat                              36

<210> SEQ ID NO 6
<211> LENGTH: 27
<212> TYPE: DNA
<213> ORGANISM: Artificial Sequence
<220> FEATURE:
<223> OTHER INFORMATION: Description of artificial sequence: reverse
      primer for amplifying murine alpha GT

<400> SEQUENCE: 6
attggtacct cagacattat ttctaac                                        27

<210> SEQ ID NO 7
<211> LENGTH: 46
<212> TYPE: DNA
<213> ORGANISM: Artificial Sequence
<220> FEATURE:
<223> OTHER INFORMATION: Description of artificial sequence: forward
      primer for amplifying human N-terminal fragment of BORIS

<400> SEQUENCE: 7
```

```
ggtggtccat gggtcgggca atggcagcca ctgagatcct ctgtcc                    46
```

<210> SEQ ID NO 8
<211> LENGTH: 55
<212> TYPE: DNA
<213> ORGANISM: Artificial Sequence
<220> FEATURE:
<223> OTHER INFORMATION: Description of artificial sequence: reverse
      primer for amplifying human N-terminal fragment of BORIS

<400> SEQUENCE: 8

```
ggtggtggat ccttagtggt ggtggtggtg gtggaaggtt ccttttgctc ccttt          55
```

<210> SEQ ID NO 9
<211> LENGTH: 48
<212> TYPE: DNA
<213> ORGANISM: Artificial Sequence
<220> FEATURE:
<223> OTHER INFORMATION: Description of artificial sequence: forward
      primer for amplifying murine N-terminal fragment of BORIS

<400> SEQUENCE: 9

```
ggtggtccat gggtcgggca atggctgccg ctgaggtccc tgtcccctt                 48
```

<210> SEQ ID NO 10
<211> LENGTH: 46
<212> TYPE: DNA
<213> ORGANISM: Artificial Sequence
<220> FEATURE:
<223> OTHER INFORMATION: Description of artificial sequence: reverse
      primer for amplifying murine N-terminal fragment of BORIS

<400> SEQUENCE: 10

```
cttagtggtg gtggtggtgg tgctgaaagc tctgaggctt tcccaa                    46
```

<210> SEQ ID NO 11
<211> LENGTH: 36
<212> TYPE: PRT
<213> ORGANISM: Artificial Sequence
<220> FEATURE:
<223> OTHER INFORMATION: Description of artificial sequence: alphaGal
      BORIS derived peptide

<400> SEQUENCE: 11

```
Lys Leu Tyr Pro Pro Glu Glu Leu Gln Arg Ile Gly Ser Leu Tyr Pro
1               5                   10                  15

Pro Glu Glu Leu Gln Arg Ile Gly Ser Leu Tyr Pro Pro Glu Glu Leu
            20                  25                  30

Gln Arg Ile Lys
        35
```

<210> SEQ ID NO 12
<211> LENGTH: 21
<212> TYPE: PRT
<213> ORGANISM: Artificial Sequence
<220> FEATURE:
<223> OTHER INFORMATION: Description of artificial sequence: secretory
      localization signal

<400> SEQUENCE: 12

```
Met Asp Leu Leu Leu Leu Leu Leu Leu Gly Leu Arg Leu Gln Leu Ser
1               5                   10                  15

Leu Gly Arg Ile Pro
            20
```

```
<210> SEQ ID NO 13
<211> LENGTH: 29
<212> TYPE: PRT
<213> ORGANISM: Artificial Sequence
<220> FEATURE:
<223> OTHER INFORMATION: Description of artificial sequence:
      Golgi-localization sequence from alpha GT

<400> SEQUENCE: 13

Met Asp Val Lys Gly Lys Val Ile Leu Leu Met Leu Ile Val Ser Thr
1               5                   10                  15

Val Val Val Val Phe Trp Glu Tyr Val Asn Arg Ile Pro
            20                  25

<210> SEQ ID NO 14
<211> LENGTH: 20
<212> TYPE: PRT
<213> ORGANISM: Artificial Sequence
<220> FEATURE:
<223> OTHER INFORMATION: Description of artificial sequence: nuclear
      localization signal

<400> SEQUENCE: 14

Met Asp Pro Lys Lys Lys Arg Lys Val Arg Ile Ala Asp Pro Lys Lys
1               5                   10                  15

Lys Arg Lys Val
            20

<210> SEQ ID NO 15
<211> LENGTH: 21
<212> TYPE: PRT
<213> ORGANISM: Artificial Sequence
<220> FEATURE:
<223> OTHER INFORMATION: Description of artificial sequence: secretory
      signal from U.S. Patent No. 6,733,997

<400> SEQUENCE: 15

Met Arg Val Leu Val Leu Ala Leu Ala Val Ala Leu Ala Val Gly Asp
1               5                   10                  15

Gln Ser Asn Leu Gly
            20

<210> SEQ ID NO 16
<211> LENGTH: 19
<212> TYPE: PRT
<213> ORGANISM: Artificial Sequence
<220> FEATURE:
<223> OTHER INFORMATION: Description of artificial sequence:
      ER/Golgi-localization or secretory signal from Preproalbumin

<400> SEQUENCE: 16

Met Lys Trp Val Thr Phe Leu Leu Leu Leu Phe Ile Ser Gly Ser Ala
1               5                   10                  15

Phe Ser Arg

<210> SEQ ID NO 17
<211> LENGTH: 23
<212> TYPE: PRT
<213> ORGANISM: Artificial Sequence
<220> FEATURE:
<223> OTHER INFORMATION: Description of artificial sequence:
      ER/Golgi-localization or secretory signal from Pre-IgG light chain

<400> SEQUENCE: 17

Met Asp Met Arg Ala Pro Ala Gln Ile Phe Gly Phe Leu Leu Leu Leu
1               5                   10                  15
```

```
Phe Pro Gly Thr Arg Cys Asp
            20

<210> SEQ ID NO 18
<211> LENGTH: 19
<212> TYPE: PRT
<213> ORGANISM: Artificial Sequence
<220> FEATURE:
<223> OTHER INFORMATION: Description of artificial sequence:
      ER/Golgi-localization or secretory signal from Prelysozyme

<400> SEQUENCE: 18

Met Arg Ser Leu Leu Ile Leu Val Leu Cys Phe Leu Pro Leu Ala Ala
1               5                   10                  15

Leu Gly Lys

<210> SEQ ID NO 19
<211> LENGTH: 29
<212> TYPE: PRT
<213> ORGANISM: Artificial Sequence
<220> FEATURE:
<223> OTHER INFORMATION: Description of artificial sequence:
      ER/Golgi-localization or secretory signal

<400> SEQUENCE: 19

Met Met Ser Phe Val Ser Leu Leu Leu Val Gly Ile Leu Phe Trp Ala
1               5                   10                  15

Thr Asp Ala Asp Asn Leu Thr Lys Cys Asp Val Phe Asn
            20                  25

<210> SEQ ID NO 20
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 20

Val Leu Ser Glu Gln Phe Thr Lys Ile
1               5

<210> SEQ ID NO 21
<211> LENGTH: 8
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 21

Val Leu Thr Val Ser Asn Ser Asn
1               5

<210> SEQ ID NO 22
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 22

Ile Leu Thr Leu Gln Thr Val His Phe Thr
1               5                   10

<210> SEQ ID NO 23
```

```
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 23

Ser Val Leu Glu Glu Glu Val Glu Leu Val
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 24

Ser Val Leu Glu Glu Glu Val Glu Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 25

Lys Leu Ala Val Ser Leu Ala Glu Thr
1               5

<210> SEQ ID NO 26
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 26

Leu Leu Ala Glu Arg Thr Lys Glu Gln Leu
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 27

Leu Ala Glu Thr Ala Gly Leu Ile Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 28

Ser Val Leu Ser Glu Gln Phe Thr Lys
```

-continued

<210> SEQ ID NO 29
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 29

Ser Leu Ala Glu Thr Ala Gly Leu Ile Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 30

Ile Leu Lys Glu Ala Thr Lys Gly Gln Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 31

Glu Ala Ala Asn Gly Asp Glu Ala Ala Ala
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 32

Leu Lys Glu Ala Thr Lys Gly Gln Lys
1               5

<210> SEQ ID NO 33
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 33

Val Leu Ala Pro Ser Glu Glu Ser Glu Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of artificial sequence: human BORIS
      derived peptide

```
<400> SEQUENCE: 34

Leu Tyr Ser Pro Gln Glu Met Glu Val Leu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 35

Glu Gln Phe Thr Lys Ile Lys Glu Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 36

Glu Val Asp Glu Gly Val Thr Cys Glu
1               5

<210> SEQ ID NO 37
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 37

Glu Glu Ser Glu Lys Tyr Ile Leu Thr Leu
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 38

Gly Val Cys Arg Glu Lys Asp His Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 39

Ser Val Leu Ser Glu Gln Phe Thr Lys
1               5

<210> SEQ ID NO 40
<211> LENGTH: 10
<212> TYPE: PRT
```

```
<213> ORGANISM: Artificial Sequence
<220> FEATURE:
<223> OTHER INFORMATION: Description of artificial sequence: Human BORIS
      derived peptide

<400> SEQUENCE: 40

Asn Val Met Val Ala Ser Glu Asp Ser Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 41

Phe Val Glu Thr Met Ser Gly Asp Glu Arg
1               5                   10

<210> SEQ ID NO 42
<211> LENGTH: 8
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 42

Ala Glu Arg Thr Lys Glu Gln Leu
1               5

<210> SEQ ID NO 43
<211> LENGTH: 8
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 43

Thr Arg Lys Arg Lys Gln Thr Ile
1               5

<210> SEQ ID NO 44
<211> LENGTH: 8
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 44

Gln Glu Met Glu Val Leu Gln Phe
1               5

<210> SEQ ID NO 45
<211> LENGTH: 9
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 45

Glu Arg Thr Lys Glu Gln Leu Phe Phe
1               5
```

```
<210> SEQ ID NO 46
<211> LENGTH: 10
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 46

Glu Glu Ser Glu Lys Tyr Ile Leu Thr Leu
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 47

Val Gln Val Val Val Gln Gln Pro Gly Pro Gly Leu Leu Trp Leu
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 48

Leu Leu Ser Ile Gln Gln Gln Glu Gly Val Gln Val Val Val Gln
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 49

Leu Leu Trp Leu Glu Glu Gly Pro Arg Gln Ser Leu Gln Gln Cys
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 50

Val Glu Thr Met Ser Gly Asp Glu Arg Ser Asp Glu Ile Val Leu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 51
```

```
Gly Glu Met Phe Pro Val Ala Cys Arg Glu Thr Thr Ala Arg Val
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 52

Ser Glu Gln Phe Thr Lys Ile Lys Glu Leu Glu Leu Met Pro Glu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 53

Lys Leu Ala Val Ser Leu Ala Glu Thr Ala Gly Leu Ile Lys Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of artificial sequence: Human BORIS
      derived peptide

<400> SEQUENCE: 54

Glu Met Glu Val Leu Gln Phe His Ala Leu Glu Glu Asn Val Met
1               5                   10                  15

<210> SEQ ID NO 55
<211> LENGTH: 10
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 55

Leu Tyr Pro Pro Glu Glu Leu Gln Arg Ile
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 56

Ser Phe Gln Asp Pro Glu His Glu Thr Leu
1               5                   10

<210> SEQ ID NO 57
<211> LENGTH: 10
<212> TYPE: PRT
<213> ORGANISM: Artificial Sequence
<220> FEATURE:
```

<223> OTHER INFORMATION: Description of artificial sequence: Murine
      BORIS derived peptide

<400> SEQUENCE: 57

His Phe His Leu Leu Arg Glu Asn Val Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 58

Tyr Phe Thr Gln Ile Lys Glu Gln Lys Leu
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 59

Leu Trp Leu Asp Pro Glu Pro Gln Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 60

His Phe His Leu Leu Arg Glu Asn Val
1               5

<210> SEQ ID NO 61
<211> LENGTH: 9
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 61

Ala Pro Val Glu Ser Asp Arg Arg Ile
1               5

<210> SEQ ID NO 62
<211> LENGTH: 9
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 62

Leu Gln Leu Pro Ser Val Leu Trp Leu
1               5

<210> SEQ ID NO 63

```
<211> LENGTH: 9
<212> TYPE: PRT
<213> ORGANISM: Artificial Sequence
<220> FEATURE:
<223> OTHER INFORMATION: Description of artificial sequence: Murine
      BORIS derived peptide

<400> SEQUENCE: 63

Val Thr Val Ser Ile Pro Glu Glu Leu
1               5

<210> SEQ ID NO 64
<211> LENGTH: 10
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 64

Ser Ser Lys Ala Leu Gln Arg Pro Val Cys
1               5                   10

<210> SEQ ID NO 65
<211> LENGTH: 31
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 65

Cys Ser Ser Lys Ala Leu Gln Arg Pro Val Gly Ser Ser Lys Ala Leu
1               5                   10                  15

Gln Arg Pro Val Gly Ser Ser Lys Ala Leu Gln Arg Pro Val Cys
            20                  25                  30

<210> SEQ ID NO 66
<211> LENGTH: 10
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 66

Lys Gln Ser Ser Lys Ala Leu Gln Arg Cys
1               5                   10

<210> SEQ ID NO 67
<211> LENGTH: 33
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 67

Cys Lys Gln Ser Ser Lys Ala Leu Gln Arg Gly Ser Lys Gln Ser Ser
1               5                   10                  15

Lys Ala Leu Gln Arg Gly Ser Lys Gln Ser Ser Lys Ala Leu Gln Arg
            20                  25                  30

Cys

<210> SEQ ID NO 68
<211> LENGTH: 10
<212> TYPE: PRT
```

<213> ORGANISM: Artificial Sequence
<220> FEATURE:
<223> OTHER INFORMATION: Description of artificial sequence: Peptide for
      vaccination against CML

<400> SEQUENCE: 68

Ala Thr Gly Phe Lys Gln Ser Ser Lys Cys
1               5                   10

<210> SEQ ID NO 69
<211> LENGTH: 34
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 69

Ala Thr Gly Phe Lys Gln Ser Ser Lys Cys Gly Ser Ala Thr Gly Phe
1               5                   10                  15

Lys Gln Ser Ser Lys Cys Gly Ser Ala Thr Gly Phe Lys Gln Ser Ser
            20                  25                  30

Lys Cys

<210> SEQ ID NO 70
<211> LENGTH: 11
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 70

His Ser Ala Thr Gly Phe Lys Gln Ser Ser Lys
1               5                   10

<210> SEQ ID NO 71
<211> LENGTH: 39
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 71

Cys His Ser Ala Thr Gly Phe Lys Gln Ser Ser Lys Gly Ser His Ser
1               5                   10                  15

Ala Thr Gly Phe Lys Gln Ser Ser Lys Gly Ser His Ser Ala Thr Gly
            20                  25                  30

Phe Lys Gln Ser Ser Lys Cys
        35

<210> SEQ ID NO 72
<211> LENGTH: 10
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 72

Gly Phe Lys Gln Ser Ser Lys Ala Leu Cys
1               5                   10

<210> SEQ ID NO 73
<211> LENGTH: 37

```
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 73

Cys Gly Phe Lys Gln Ser Ser Lys Ala Leu Cys Gly Ser Cys Gly Phe
1               5                   10                  15

Lys Gln Ser Ser Lys Ala Leu Cys Gly Ser Cys Gly Phe Lys Gln Ser
            20                  25                  30

Ser Lys Ala Leu Cys
        35

<210> SEQ ID NO 74
<211> LENGTH: 27
<212> TYPE: PRT
<213> ORGANISM: Artificial Sequence
<220> FEATURE:
<223> OTHER INFORMATION: Description of artificial sequence: Peptide for
      vaccination against CML

<400> SEQUENCE: 74

Cys Ile Val His Ser Ala Thr Gly Phe Lys Gln Ser Ser Lys Ala Leu
1               5                   10                  15

Gln Arg Pro Val Ala Ser Asp Phe Glu Pro Cys
            20                  25

<210> SEQ ID NO 75
<211> LENGTH: 8
<212> TYPE: PRT
<213> ORGANISM: Artificial Sequence
<220> FEATURE:
<223> OTHER INFORMATION: Description of artificial sequence: Peptide
      derived from murine TAA gp75 (TRP-1)

<400> SEQUENCE: 75

Thr Trp His Arg Tyr His Leu Leu
1               5

<210> SEQ ID NO 76
<211> LENGTH: 8
<212> TYPE: PRT
<213> ORGANISM: Artificial Sequence
<220> FEATURE:
<223> OTHER INFORMATION: Description of artificial sequence: Peptide
      derived from murine TAA gp75 (TRP-1)

<400> SEQUENCE: 76

Thr Ala Tyr Arg Tyr His Leu Leu
1               5

<210> SEQ ID NO 77
<211> LENGTH: 9
<212> TYPE: PRT
<213> ORGANISM: Artificial Sequence
<220> FEATURE:
<223> OTHER INFORMATION: Description of artificial sequence: Peptide
      derived from murine TAA gp75 (TRP-1)

<400> SEQUENCE: 77

Lys Thr Ala Tyr Arg Tyr His Leu Leu
1               5

<210> SEQ ID NO 78
<211> LENGTH: 30
<212> TYPE: PRT
```

-continued

```
<213> ORGANISM: Artificial Sequence
<220> FEATURE:
<223> OTHER INFORMATION: Description of artificial sequence: Peptide
      derived from murine TAA gp75 (TRP-1)

<400> SEQUENCE: 78

Lys Thr Ala Tyr Arg Tyr His Leu Leu Gly Ser Thr Ala Tyr Arg Tyr
1               5                   10                  15

His Leu Leu Gly Ser Thr Ala Tyr Arg Tyr His Leu Leu Lys
            20                  25                  30

<210> SEQ ID NO 79
<211> LENGTH: 9
<212> TYPE: PRT
<213> ORGANISM: Artificial Sequence
<220> FEATURE:
<223> OTHER INFORMATION: Description of artificial sequence: gp75
      derived peptide

<400> SEQUENCE: 79

Lys Thr Ala Tyr Arg Tyr His Leu Leu
1               5

<210> SEQ ID NO 80
<211> LENGTH: 19
<212> TYPE: PRT
<213> ORGANISM: Artificial Sequence
<220> FEATURE:
<223> OTHER INFORMATION: Description of artificial sequence: gp75
      derived peptide

<400> SEQUENCE: 80

Lys Thr Ala Tyr Arg Tyr His Leu Leu Gly Ser Thr Ala Tyr Arg Tyr
1               5                   10                  15

His Leu Leu

<210> SEQ ID NO 81
<211> LENGTH: 30
<212> TYPE: PRT
<213> ORGANISM: Artificial Sequence
<220> FEATURE:
<223> OTHER INFORMATION: Description of artificial sequence: gp75
      derived peptide

<400> SEQUENCE: 81

Lys Thr Ala Tyr Arg Tyr His Leu Leu Gly Ser Thr Ala Tyr Arg Tyr
1               5                   10                  15

His Leu Leu Gly Ser Thr Ala Tyr Arg Tyr His Leu Leu Lys
            20                  25                  30

<210> SEQ ID NO 82
<211> LENGTH: 6
<212> TYPE: PRT
<213> ORGANISM: Artificial Sequence
<220> FEATURE:
<223> OTHER INFORMATION: Description of artificial sequence: Golgi
      localization signal consensus sequence
<220> FEATURE:
<221> NAME/KEY: MISC_FEATURE
<222> LOCATION: (1)..(1)
<223> OTHER INFORMATION: X = aromatic or bulky hydrophobic residue
<220> FEATURE:
<221> NAME/KEY: MISC_FEATURE
<222> LOCATION: (2)..(2)
<223> OTHER INFORMATION: X = aromatic or bulky hydrophobic residue
<220> FEATURE:
<221> NAME/KEY: X
<222> LOCATION: (5)..(5)
<223> OTHER INFORMATION: X = any amino acid residue
```

```
<400> SEQUENCE: 82

Xaa Xaa Arg Arg Xaa Arg
1               5

<210> SEQ ID NO 83
<211> LENGTH: 5
<212> TYPE: PRT
<213> ORGANISM: Artificial Sequence
<220> FEATURE:
<223> OTHER INFORMATION: Description of artificial sequence: C-terminal
      Golgi localization signal
<220> FEATURE:
<221> NAME/KEY: X
<222> LOCATION: (2)..(2)
<223> OTHER INFORMATION: X = any amino acid residue
<220> FEATURE:
<221> NAME/KEY: X
<222> LOCATION: (4)..(4)
<223> OTHER INFORMATION: X = any amino acid residue
<220> FEATURE:
<221> NAME/KEY: X
<222> LOCATION: (5)..(5)
<223> OTHER INFORMATION: X = any amino acid residue

<400> SEQUENCE: 83

Lys Xaa Lys Xaa Xaa
1               5
```